(12) United States Patent
Davis et al.

(10) Patent No.: US 7,176,215 B2
(45) Date of Patent: Feb. 13, 2007

(54) BICYCLIC OXOPYRIDINE AND OXOPYRIMIDINE DERIVATIVES

(75) Inventors: Jeremy Martin Davis, Workingham (GB); Daniel Christopher Brookings, Reading (GB); Barry John Langham, Reading (GB)

(73) Assignee: Celltech R&D Limited, Berkshire (GB)

( * ) Notice: Subject to any disclaimer, the term of this patent is extended or adjusted under 35 U.S.C. 154(b) by 0 days.

(21) Appl. No.: 10/492,466

(22) PCT Filed: Oct. 16, 2002

(86) PCT No.: PCT/GB02/04680

§ 371 (c)(1),
(2), (4) Date: Jul. 20, 2004

(87) PCT Pub. No.: WO03/033502

PCT Pub. Date: Apr. 24, 2003

(65) Prior Publication Data

US 2004/0254200 A1     Dec. 16, 2004

(30) Foreign Application Priority Data

Oct. 16, 2001   (GB)   ................. 0124848.3

(51) Int. Cl.
 A01N 43/42   (2006.01)
 A61K 31/44   (2006.01)
 C07D 471/02  (2006.01)
 C07D 491/02  (2006.01)
 C07D 498/02  (2006.01)

(52) U.S. Cl. .............. 514/300; 514/301; 546/114; 546/113; 544/278; 544/255

(58) Field of Classification Search ................ 546/114, 546/113; 544/278, 255; 514/301, 300
See application file for complete search history.

(56) References Cited

FOREIGN PATENT DOCUMENTS

| EP | 0 090 275 B1 | 10/1987 |
|---|---|---|
| EP | 0 623 598 A1 | 11/1994 |
| JP | 07076586 | * 3/1995 |
| JP | 09059276 | 4/1997 |
| WO | WO 99/64400 A1 | 12/1999 |
| WO | WO 01/37837 A1 | 5/2001 |
| WO | WO 01/64679 A1 | 9/2001 |

OTHER PUBLICATIONS

Henry et al., "Potent Inhibitors of the Map Kinase p. 38", CA 130:177125.*
Jae Youl Cho et al., "In vitro Inhibitory Efect of Protopanaxadiol Ginsenosides on Tumor Necrosis Factor (TNF)-α Production and its Modulation by known TNF-α Antagonists", Planta Med, pp. 213-218.*
Kui Liu et al., "Sle 1 ab Mediates the Aberrant Activation of STAT3 and Ras-ERK Signaling Pathways in B Lymphocytes", The Journal of Immunology, pp. 1630-1637.*
Valerie Duplan et al., "LF 15-0195 Treatment Protects against Central Nervous System Autoimmunity by Favoring the Development of Foxp3-Expressing Regulatory CD4 T Cells", The journal of Immunology, pp. 839-847.*
Andreas Pascher et al., "Biologics in the Treatment of Transplant Rejection and Ischemia/Reperfusion Injury", Biodrugs, pp. 211-231.*

(Continued)

Primary Examiner—Thomas McKenzie
Assistant Examiner—Niloofar Rahmani
(74) Attorney, Agent, or Firm—Woodcock Washburn LLP

(57) ABSTRACT

Compounds of formulae (1a) and (1b) are described: in which the dashed line represents an optional bond; A is a —N= atom or a —N($R^b$)—, —C($R^b$)= or —C($R^b$)($R^c$)— group; $R^a$, $R^b$ and $R^c$ is each independently a hydrogen atom or an optionally substituted $C^{1-6}$alkyl group; X is an —O— or —S— atom or —NH— group or substituted N atom; each Y is independently a N atom or CH group or substituted C atom; n is zero or the integer 1; $Alk^1$ is an optionally substituted aliphatic or heteroaliphatic chain $L^1$ is a covalent bond or a linker atom or group; $Cy^1$ is a hydrogen atom or an optionally substituted cycloaliphatic, polycycloaliphatic, heterocycloaliphatic, polyheterocycloaliphatic, aromatic or heteroaromatic group; Ar is an optionally substituted aromatic or heteroaromatic group; and the salts, solvates, hydrates and N-oxides thereof; The compounds are potent inhibitors of p38 kinase and are use in the prophylaxis or treatment of p38 kinase mediated diseases or disorders, such as rheumatoid arthritis

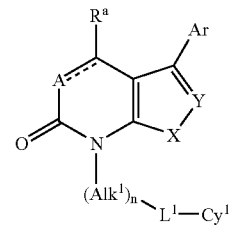
(1a)

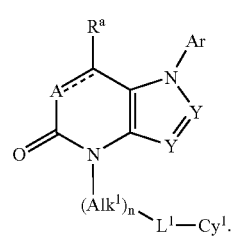

(1b)

15 Claims, No Drawings

OTHER PUBLICATIONS

Tochiro Tatee et al., "Isoxazole derivatives as Centrally Acting Muscle Relaxants. III. Synthesis and Activity of Conformationally Restricted Analogs", Chemical & Pharmaceutical Buletin, pp. 3676-3690.*

Adams, J.L., et al., "p38 MAP kinase: molecular target for the inhibition of pro-inflammatory cytokines," Progress in Medicinal Chemistry, Elsevier Science, King, F.D., et al. (Eds.), 2001, 38, 1-60.

Allen, M., et al., "Deficiency of the stress kinase p38α results in embryonic lethality: characterization of the kinase dependence of stress responses of enzyme-deficient embryonic stem cells," J. Exp. Med., 2000, 191, 859-869.

Badger, A.M., et al., "Pharmacological profile of SB 203580, a selective inhibitor of cytokine suppressive binding protein/p38 kinase, in animal models of arthritis, bone resorption, endotoxin shock and immune function," J. Pharm. & Exp. Ther., 1996, 279, 1453-1461.

Chan, D.T., et al., "New N- and O-arylations with phenylboronic acids and cupric acetate," Tetrahedron Letts., 1998, 2933-2936.

Cohen, P., "The search for physiological substrates of MAP and SAP kinases in mammalian cells," Trends Cell Biol., 1997, 7, 353-361.

Dinarello, C.A., "An update on human interleukin-1: from molecular biology to clinical relevance," J. of Clinical Immunology, 1985, 5(5), 287-297.

Doza, Y.N., et al., "Activation of the MAP kinase homologue RK requires the phosphorylation of Thr-180 and Tyr-182 and both residues are phosphorylated in chemically stressed KB cells," FEBS Lett., 1995, 364, 223-228.

Enslen, H., et al., "Selective activation of p38 mitogen-activated protein (MAP) kinase isoforms by the MAP kinase kinases MKK3 and MKK6," J. of Biol. Chem., 1998, 273(3), 1741-1748.

Glamkowski, E.J., et al., "3-(1-indolinyl)benzylamines: a new class of analgesic agents," J. Med. Chem., 1985, 28, 66-73.

Griswold, D.E., et al., "Pharmacology of cytokine suppressive anti-inflammatory drug binding protein (CSBP), a novel stress-induced kinase," Pharmacol. Comm., 1996, 7, 323-329.

Grunberg, K., et al., "Effect of rhinovirus 16 (RV16) cold on airway responsiveness to indirect stimuli in asthmatics," Am. J. Crit. Care Med., 1997, 155, p. A743 (abstract).

Hale, K.K., et al., "Differential expression and activation of p38 mitogen-activated protein kinase α, β, γ, and δ in inflammatory cell lineages," Am. J. of Immun., 1999, 162, 4246-4252.

Hunter, T., "Protein kinase classification," Methods in Enzymology, Academic Press, 1991, 200, 3-37.

Ishii, H., et al., "Fischer indolisation and related compounds. Part 21. Direction on the cyclisation in the Fischer indolisation of ethyl pyruvate 2-)p- or m-substituted phenyl)phenylhydrazones," J. Chem. Soc. Perkin Trans. 1, 1989, 2407-2414.

Kotlyarov, A., et al., "MAPKAP kinase 2 is essential for LPS-induced TNF-α biosynthesis," Nature Cell Biol., 1999, 1, 94-97.

Kundu, N.G., et al., "A highly convenient procedure for the synthesis of 5-(2-acylvinyl)uracils, a group of novel 5-substituted uracils," J. Chem. Soc. Perkin Trans. 1, 1990, 1822-1824.

Lam, P.Y.S., et al., "Copper-catalyzed general C-N and C-O bond cross-coupling with arylboronic acid," Tetrahedron Letts., 2001, 3415-3418.

Lee, J.C., et al., "Bicyclic imidazoles as a novel class of cytokine biosynthesis inhibitors," Annals N.Y. Acad. Sci., 1993, 696, 149-170.

Lee, J.C., et al., "Inhibition of monocyte IL-1 production by the anti-inflammatory compound, SK&F 86002," Int. J. Immunopharm., 1988, 10(7), 835-843.

Lee, J.C., et al., "A protein kinase involved in the regulation of inflammatory cytokine biosynthesis," Nature, 1994, 372, 739-746.

Mahadevan, I., et al., "synthesis of pyrrolopyridines (azaindoles)," J. Heterocyclic Chem., 1992, 29, 359-367.

Mann, G., et al., "Palladium-catalyzed C-N9sp$^2$) bond formation: N-arylation of aromatic and unsaturated nitrogen and the reductive elimination chemistry of palladium azolyl and methyleneamido complexes," J. Am. Chem. Soc., 1998, 120, 827-828.

Mattson, R.J., et al., "Ortho-directed lithiation in π-deficient diazinyl heterocycles," J. Org. Chem., 1990, 55, 3410-3412.

McDonnell, P.C., et al., "Localization of the human stress responsive MAP kinase-like CSAIDs binding protein (CSBP) gene to chromosome 6p21.3/21.2," Genomics, 1995, 28, 301-302.

Subauste, M.C., et al., "Infection of a human respiratory epithelial cell line with rhinovirus, Induction of cytokine release and modulation of susceptibility to infection by cytokine exposure," J. Clin. Invest., 1995, 96, 549-557.

Stabler, S., et al., "Preparation of N-arylated heterocycles by nucleophilic aromatic substitution," Synth. Commun., 1994, 24(1), 123-129.

Takekawa, M., et al., "A family of stress-inducible GADD45-like proteins mediate activation of the stress-responsive MTK1/MEKK4 MAPKKK," Cell, 1998, 95, 521-530.

Turck, A., et al., "Metallation of diazines II. First metallation of pyridazine, metallation of 2,4-dichloropyrimidine," J. Het. Chem., 1990, 27, 1377-1381.

Turner, R.B., et al., "Association between interleukin-8 concentration in nasal secretions and severity of symptoms of experimental rhinovirus colds," Clin. Infec. Dis., 1998, 26, 840-846.

Zhu, Z., et al., "Rhinovirus stimulation of interleukin-6 in vivo and in vitro, evicence for nuclear factor κB-dependent transcriptional activation," J. of Clin. Invest., 1996, 97(2), 421-430.

* cited by examiner

BICYCLIC OXOPYRIDINE AND OXOPYRIMIDINE DERIVATIVES

This invention relates to a series of 5–6 fused ring bicyclic heteroaromatic derivatives, to compositions containing them, to processes for their preparation and to their use in medicine.

Immune and inflammatory responses involve a variety of cell types with control and co-ordination of the various interactions occurring via both cell-cell contacts (e.g integrin interactions with their receptors) and by way of intercellular signalling molecules. A large number of different signalling molecules are involved including cytokines, lymphocytes, chemokines and growth factors.

Cells respond to such intercellular signalling molecules by means of intracellular signalling mechanisms that include protein kinases, phosphatases and phospholipases. There are five classes of protein kinase of which the major ones are the tyrosine kinases and the serine/threonine kinases [Hunter, T., Methods in Enzymology (Protein Kinase Classification) p. 3, Hunter, T. and Sefton, B. M.; eds. Vol. 200, Academic Press; San Diego, 1991].

One sub-class of serine/threonine kinases is the mitogen activating protein (MAP) kinases of which there are at least three families which differ in the sequence and size of the activation loop [Adams, J. L. et al, Progress in Medicinal Chemistry p. 1–60, King, F. D. and Oxford, A. W.; eds. vol 38, Elsevier Science, 2001]: the extracellular regulated kinases (ERKs), the c-Jun $NH_2$ terminal kinases or stress activated kinases (JNKs or SAP kinases) and the p38 kinases which have a threonine-glycine-tyrosine (TGY) activation motif. Both the JNKs and p38 MAP kinases are primarily activated by stress stimuli including, but not limited to, proinflammatory cytokines e.g. tumour necrosis factor (TNF) and interleukin-1 (IL-1), ultraviolet light, endotoxin and chemical or osmotic shock.

Four isoforms of p38 have been described (p38α/β/γ/δ). The human p38α enzyme was initially identified as a target of cytokine-suppressive anti-inflammatory drugs (CSAIDs) and the two isoenzymes found were initially termed CSAID binding protein-1 (CSBP-1) and CSBP-2 [Lee, J. C. et al, Nature (London) 1994, 372, 739–46]. CSBP-2 is now widely referred to as p38α and differs from CSBP-1 in an internal sequence of 25 amino acids as a result of differential splicing of two exons that are conserved in both mouse and human [McDonnell, P. C. et al, Genomics 1995, 29, 301–2]. CSBP-1 and p38α are expressed ubiquitously and there is no difference between the two isoforms with respect to tissue distribution, activation profile, substrate preference or CSAID binding. A second isoform is p38β which has 70% identity with p38α. A second form of p38β termed p38β2 is also known and of the two this is believed to be the major form. p38α and p38β2 are expressed in many different tissues. However in monocytes and macrophages p38α is the predominant kinase activity [Lee, J. C., ibid; Jing, Y. et al, J. Biol. Chem. 1996, 271, 10531–34; Hale, K. K. et al, J. Immun. 1999, 162, 4246–52]. p38γ and p38δ (also termed SAP kinase-3 and SAP kinase-4 respectively) have ~63% and ~61% homology to p38α respectively. p38δ is predominantly expressed in skeletal muscle whilst p38δ is found in testes, pancreas, prostate, small intestine and in certain endocrine tissues.

All p38 homologues and splice variants contain a 12 amino acid activation loop that includes a Thr-Gly-Tyr motif. Dual phosphorylation of both Thr-180 and Tyr-182 in the TGY motif by a dual specificity upstream kinase is essential for the activation of p38 and results in a >1000-fold increase in specific activity of these enzymes [Doza, Y. N. et al FEBS Lett., 1995, 364, 7095–8012]. This dual phosphorylation is effected by MKK6 and under certain conditions the related enzyme MKK3 (see FIG. 1) [Enslen, H. et al J. Biol. Chem., 1998, 273,1741–48]. MKK3 and MKK6 belong to a family of enzymes termed MAPKK (mitogen activating protein kinase kinase) which are in turn activated by MAPKKK (mitogen activating kinase kinase kinase) otherwise known as MAP3K.

Several MAP3Ks have been identified that are activated by a wide variety of stimuli including environmental stress, inflammatory cytokines and other factors. MEKK4/MTK1 (MAP or ERK kinase kinase/MAP three kinase-1), ASK1 (apoptosis stimulated kinase) and TAK1 (TGF-β-activated kinase) are some of the enzymes identified as upstream activators of for MAPKKs. MEKK4/MTK1 is thought to be activated by several GADD-45-like genes that are induced in response to environmental stimuli and which eventually lead to p38 activation [Takekawa, M. and Saito, H. Cell, 1998, 95, 521–30]. TAK1 has been shown to activate MKK6 in response to transforming growth factor-β (TGF-β). TNF-stimulated activation of p38 is believed to be mediated by the recruitment of TRAF2 [TNF receptor associated factor] and the Fas adaptor protein, Daxx, which results in the activation of ASK1 and subsequently p38.

Several substrates of p38 have been identified including other kinases [e.g. MAPK activated protein kinase 2/3/5 (MAPKAP 2/3/5), p38 regulated/activated protein kinase (PRAK), MAP kinase-interacting kinase 1/2 (MNK1/2), mitogen- and stress-activated protein kinase 1 (MSK1/RLPK) and ribosomal S6 kinase-B (RSK-B)], transcription factors [e.g. activating transcription factor 2/6 (ATF2/6), monocyte-enhancer factor-2A/C (MEF2A/C), C/EBP homologous protein (CHOP), Elk1 and Sap-1a1] and others substrates [e.g. cPLA2, p47phox].

MAPKAP K2 is activated by p38 in response to environmental stress. Mice engineered to lack MAPKAP K2 do not produce TNF in response to lipopolysaccharide (LPS). Production of several other cytokines such as IL-1, IL-6, IFN-g and IL-10 is also partially inhibited [Kotlyarov, A. et al Nature Cell Biol. 1999, 1, 94–7]. Further, MAPKAP K2 from embryonic stem cells from p38α null mice was not activated in response to stress and these cells did not produce IL-6 in response to IL-1 [Allen, M. et al, J. Exp. Med. 2000, 191, 859–69]. These results indicate that MAPKAP K2 is not only essential for TNF and IL-1 production but also for signalling induced by cytokines. In addition MAPKAP K2/3 phosphorylate and thus regulate heat shock proteins HSP 25 and HSP 27 which are involved in cytoskeletal reorganization.

Several small molecule inhibitors of p38 have been reported which inhibit IL-1 and TNF synthesis in human monocytes at concentrations in the low μM range [Lee, J. C. et al, Int. J. Immunopharm. 1988, 10, 835] and exhibit activity in animal models which are refractory to cyclooxygenase inhibitors [Lee, J. C. et al, Annals N. Y. Acad. Sci. 1993, 696, 149]. In addition these small molecule inhibitors are known to also decrease the synthesis of a wide variety of pro-inflammatory proteins including IL-6, IL-8, granulocyte/macrophage colony-stimulating factor (GM-CSF) and cyclooxygenase-2 (COX-2). TNF-induced phosphorylation and activation of cytosolic PLA2, TNF-induced expression of VCAM-1 on endothelial cells and IL-1 stimulated synthesis of collagenase and stromelysin are also inhibited by such small molecule inhibitors of p38 [Cohen, P. Trends Cell Biol. 1997, 7, 353–61].

A variety of cells including monocytes and macrophages produce TNF and IL-1. Excessive or unregulated TNF production is implicated in a number of disease states including Crohn's disease, ulcerative colitis, pyresis, rheumatoid arthritis, rheumatoid spondylitis, osteoarthritis, gouty arthritis and other arthritic conditions, toxic shock syndrome, endotoxic shock, sepsis, septic shock, gram negative sepsis, bone resporption diseases, reperfusion injury, graft vs. host reaction, allograft rejection, adult respiratory distress syndrome, chronic pulmonary inflammatory disease, silicosis, pulmonary sarcoisosis, cerebral malaria, scar tissue formation, keloid formation, fever and myalgias due to infection, such as influenza, cachexia secondary to acquired immune deficiency syndrome (AIDS), cachexia secondary to infection or malignancy, AIDS or AIDS related complex.

Excessive or unregulated IL-1 production has been implicated in rheumatoid arthritis, osteoarthritis, traumatic arthritis, rubella arthritis, acute synovitis, psoriatic arthritis, cachexia, Reiter's syndrome, endotoxemia, toxic shock syndrome, tuberculosis, atherosclerosis, muscle degeneration, and other acute or chronic inflammatory diseases such as the inflammatory reaction induced by endotoxin or inflammatory bowel disease. In addition IL-1 has been linked to diabetes and pancreatic β cells [Dinarello, C. A. J. Clinical Immunology, 1985, 5, 287–97].

IL-8 is a chemotactic factor produced by various cell types including endothelial cells, mononuclear cells, fibroblasts and keratinocytes. IL-1, TNF and LPS all induce the production of IL-8 by endothelial cells. In vitro IL-8 has been shown to have a number of functions including being a chemoattractant for neutrophils, T-lymphocytes and basophils. IL-8 has also been shown to increase the surface expression of Mac-1 (CD11b/CD18) on neutrophils without de novo protein synthesis which may contribute to increased adhesion of neutrophils to vascular endothelial cells. Many diseases are characterised by massive neutrophil infiltration. Histamine release from basophils (in both atopic and normal individuals) is induced by IL-8 as is lysozomal enzyme release and respiratory burst from neutrophils.

The central role of IL-1 and TNF together with other leukocyte derived cytokines as important and critical inflammatory mediators is well documented. The inhibition of these cytokines has been shown or would be expected to be of benefit in controlling, alleviating or reducing many of these disease states.

The central position that p38 occupies within the cascade of signalling molecules mediating extracellular to intracellular signalling and its influence over not only IL-1, TNF and IL-8 production but also the synthesis and/or action of other pro-inflammatory proteins (e.g. IL-6, GM-CSF, COX-2, collagenase and stromelysin) make it an attractive target for inhibition by small molecule inhibitors with the expectation that such inhibition would be a highly effective mechanism for regulating the excessive and destructive activation of the immune system. Such an expectation is supported by the potent and diverse anti-inflammatory activities described for p38 kinase inhibitors [Adams, ibid; Badger, et al, J. Pharm. Exp. Ther. 1996, 279, 1453–61; Griswold, et al, Pharmacol. Comm., 1996, 7, 323–29].

Japanese patent application No. JP09059276 describes a series of pyrazalopyridinones and analogs with utility as herbicides.

We have now found a group of compounds which are potent and selective inhibitors of p38 kinase (p38α, β, δ and γ) and the isoforms and splice variants thereof, especially p38α, p38β and p38β2. The compounds are thus of use in medicine, for example in the prophylaxis and treatment of immune or inflammatory disorders as described herein.

Thus according to one aspect of the invention we provide a compound of formula (1a) or (1b):

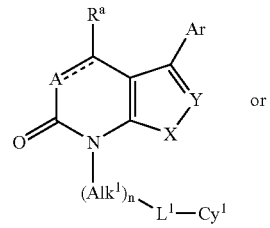

(1a)

or

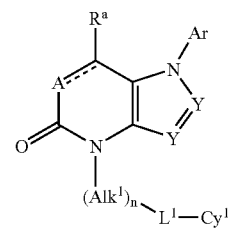

(1b)

wherein:

the dashed line represents an optional bond;

A is a —N= atom or a —N($R^b$)—, —C($R^b$)= or —C($R^b$)($R^c$)— group;

$R^a$, $R^b$ and $R^c$ is each independently a hydrogen atom or an optionally substituted $C_{1-6}$alkyl group;

X is an —O— or —S— atom or —NH— group or substituted N atom;

each Y is independently a N atom or CH group or substituted C atom;

n is zero or the integer 1;

$Alk^1$ is an optionally substituted aliphatic or heteroaliphatic chain $L^1$ is a covalent bond or a linker atom or group;

$Cy^1$ is a hydrogen atom or an optionally substituted cycloaliphatic, polycycloaliphatic, heterocycloaliphatic, polyheterocycloaliphatic, aromatic or heteroaromatic group;

Ar is an optionally substituted aromatic or heteroaromatic group;

and the salts, solvates, hydrates and N-oxides thereof;

for the manufacture of a medicament for the prophylaxis or treatment of a p38 kinase mediated disease or disorder.

This invention also relates to a compound of formula (1a) or (1b) for use in the prophylaxis or treatment of a p38 kinase mediated disease or disorder in a mammal in need thereof.

This invention also relates to a compound of formula (1a) or (1b) for use in the prophylaxis or treatment of a cytokine mediated disease or disorder in a mammal in need thereof.

This invention more specifically relates to a method of inhibiting the production of IL-1 in a mammal in need thereof.

This invention more specifically relates to a method of inhibiting the production of IL-6 in a mammal in need thereof.

This invention more specifically relates to a method of inhibiting the production of IL-8 in a mammal in need thereof.

This invention more specifically relates to a method of inhibiting the production of TNF in a mammal in need thereof.

This invention more specifically relates to the administration to a mammal of an effective amount of a p38 kinase or cytokine, specifically IL-1, IL-6, IL-8 or TNF, inhibitor of formula (1a) or (1b).

Compounds according to the invention are potent and selective inhibitors of p38 kinases, including all isoforms and splice variants thereof. More specifically the compounds of the invention are inhibitors of p38α, p38β and p38β2. The ability of the compounds to act in this way may be simply determined by employing tests such as those described in the Examples hereinafter.

The compounds of formula (1) are of use in modulating the activity of p38 kinases and in particular are of use in the prophylaxis and treatment of any p38 kinase mediated diseases or disorders in a human, or other mammal. The invention extends to such a use and to the use of the compounds for the manufacture of a medicament for treating such diseases or disorders. Further the invention extends to the administration to a human an effective amount of a p38 inhibitor for treating any such disease or disorder.

The invention also extends to the prophylaxis or treatment of any disease or disorder in which p38 kinase plays a role including conditions caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further the invention extends to the administration to a human an effective amount of a p38 inhibitor for treating any such disease or disorder.

Diseases or disorders in which p38 kinase plays a role either directly or via pro-inflammatory cytokines including the cytokines TNF, IL-1, IL-6 and IL-8 include without limitation autoimmune diseases, inflammatory diseases, destructive-bone disorders, proliferative disorders, neurodegenerative disorders, viral diseases, allergies, infectious diseases, heart attacks, angiogenic disorders, reperfusion/ischemia in stroke, vascular hyperplasia, organ hypoxia, cardiac hypertrophy, thrombin-induced platelet aggregation and conditions associated with prostaglandin endoperoxidase synthetase-2 (COX-2).

Autoimmune diseases which may be prevented or treated include but are not limited to rheumatoid arthritis, inflammatory bowel disease, ulcerative colitis, Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, chronic active hepatitis, myasthenia gravis, atopic dermatitis, graft vs. host disease or psoriasis.

The invention further extends to the particular autoimmune disease rheumatoid arthritis.

Inflammatory diseases which may be prevented or treated include but are not limited to asthma, allergies, respiratory distress syndrome or acute or chronic pancreatitis.

Destructive bone disorders which may be prevented or treated include but are not limited to osteoporosis, osteoarthritis and multiple myeloma-related bone disorder.

Proliferative diseases which may be prevented or treated include but are not limited to acute or chronic myelogenous leukemia, Kaposi's sarcoma, metastic melanoma and multiple myeloma.

Neurodegenerative diseases which may be prevented or treated include but are not limited to Parkinson's disease, Alzheimer's disease, cerebral ischemias or neurodegenerative disease caused by traumatic injury.

Viral diseases which may be prevented or treated include but are not limited to acute hepatitis infection (including hepatitis A, hepatitis B and hepatitis C), HIV infection and CMV retinitis.

Infectious diseases which may be prevented or treated include but are not limited to septic shock, sepsis and Shigellosis.

In addition, p38 inhibitors of this invention also exhibit inhibition of expression of inducible pro-inflammatory proteins such as prostaglandin endoperoxidase synthetase-2, otherwise known as cyclooxygenase-2 (COX-2) and are therefore of use in therapy. Pro-inflammatory mediators of the cyclooxygenase pathway derived from arachidonic acid are produced by inducible COX-2 enzyme. Regulation of COX-2 would regulate these pro-inflammatory mediators such as prostaglandins, which affect a wide variety of cells and are important and critical inflammatory mediators of a wide variety of disease states and conditions. In particular these inflammatory mediators have been implicated in pain, such as in the sensitization of pain receptors, or edema. Accordingly additional p38 mediated conditions which may be prevented or treated include edema, analgesia, fever and pain such as neuromuscular pain, headache, dental pain, arthritis pain and pain caused by cancer.

As a result of their p38 inhibitory activity, compounds of the invention have utility in the prevention and treatment of diseases associated with cytokine production including but not limited to those diseases associated with TNF, IL-1, IL-6 and IL-8 production.

Thus TNF mediated diseases or conditions include for example rheumatoid arthritis, rheumatoid spondylitis, osteoarthritis, gouty arthritis and other arthritic conditions, sepsis, septic shock syndrome, adult respiratory distress syndrome, cerebral malaria, chronic pulmonary inflammatory disease, silicosis, pulmonary sarcoiosis, bone resportion disease, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis, pyresis, viral infections such as HIV, CMV, influenza and herpes; and vetinary viral infections, such as lentivirus infections, including but not limited to equine infectious anemia virus, caprine arthritis virus, visna virus or maedi virus; or retrovirus infections, including feline immunodeficiency virus, bovine immunodeficiency virus or canine immunodeficiency virus.

Compounds of the invention may also be used in the treatment of viral infections, where such viruses elicit TNF production in vivo or are sensitive to upregulation by TNF. Such viruses include those that produce TNF as a result of infection and those that are sensitive to inhibition, for instance as a result of decreased replication, directly or indirectly by the TNF inhibiting compounds of the invention. Such viruses include, but are not limited to, HIV-1, HIV-2 and HIV-3, Cytomegalovirus (CMV), Influenza, adenovirus and the Herpes group of viruses such as Herpes Zoster and Herpes Simplex.

IL-1 mediated diseases or conditions include for example rheumatoid arthritis, osteoarthritis, psoriatic arthritis, traumatic arthritis, rubella arthritis, inflammatory bowel disease, stroke, endotoxemia and/or toxic shock syndrome, inflammatory reaction induced by endotoxin, diabetes, pancreatic β-cell disease, Alzheimer's disease, tuberculosis, atherosclerosis, muscle degeneration and cachexia.

IL-8 mediated diseases and conditions include for example those characterized by massive neutrophil infiltration such as psoriasis, inflammatory bowel disease, asthma, cardiac, brain and renal reperfusion injury, adult respiratory distress syndrome, thrombosis and glomerulonephritis. The increased IL-8 production associated with each of these diseases is responsible for the chemotaxis of neutrophils into inflammatory sites. This is due to the unique property of IL-8 (in comparison to TNF, IL-1 and IL-6) of promoting neutrophil chemotaxis and activation. Therefore, inhibition of IL-8 production would lead to a direct reduction in neutrophil infiltration.

It is also known that both IL-6 and IL-8 are produced during rhinovirus (HRV) infections and contribute to the pathogenesis of the common cold and exacerbation of asthma associated with HRV infection [Turner et al, Clin. Infec. Dis., 1997, 26, 840; Grunberg et al, Am. J. Crit. Care Med. 1997, 155, 1362; Zhu et al, J. Clin. Invest. 1996, 97, 421]. It has also been demonstrated in vitro that infection of pulmonary epithelial cells (which represent the primary site of infection by HRV) with HRV results in production of IL-6 and IL-8 [Sabauste et al, J. Clin. Invest. 1995, 96, 549]. Therefore, p38 inhibitors of the invention may be used for the treatment or prophylaxis of the common cold or respiratory viral infection caused by human rhinovirus infection (HRV), other enteroviruses, coronavirus, influenza virus, parainfluenza virus, respiratory syncytial virus or adenovirus infection.

For the prophylaxis or treatment of a p38 or pro-inflammatory cytokine mediated disease the compounds according to the invention may be administered to a human or mammal as pharmaceutical compositions, and according to a further aspect of the invention we provide a pharmaceutical composition which comprises a compound of formula (1a) or (1b) together with one or more pharmaceutically acceptable carriers, excipients or diluents.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1a) or (1b) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1a) or (1b) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds for use according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively the compounds for use according to the present invention may be formulated in a suitable lotion containing the active component suspended or dissolved in one or more pharmaceutically acceptable carriers. Particular carriers include, for example mineral oil, sorbitan monostearate, polysorbate 60, cetyl esters wax, cetearyl alcohol, benzyl alcohol, 2-octyldodecanol and water.

For ophthalmic administration the compounds for use according to the present invention may be conveniently formulated as microionized suspensions in isotonic, pH adjusted sterile saline, either with or without a preservative such as bactericidal or fungicidal agent, for example phenylmercuric nitrate, benzylalkonium chloride or chlorhexidine acetate. Alternatively for ophthalmic administration compounds may be formulated in an ointment such as petrolatum.

For rectal administration the compounds for use according to the present invention may be conveniently formulated as suppositories. These can be prepared by mixing the active component with a suitable non-irritating excipient which is solid at room temperature but liquid at rectal temperature and so will melt in the rectum to release the active component. Such materials include for example cocoa butter, beeswax and polyethylene glycols.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

Particular compounds of formula (1a) and formula (1b) form a further aspect of the invention. Thus we provide a compound of formula (1a):

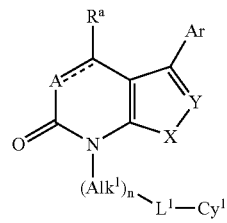

(1a)

wherein:
the dashed line represents an optional bond;
A is a —N= atom or a —N($R^b$)—, —C($R^b$)= or —C($R^b$)($R^c$)— group;
$R^a$, $R^b$ and $R^c$ is each independently a hydrogen atom or an optionally substituted $C_{1-6}$alkyl group;
X is an —O— or —S— atom or —NH— group or substituted N atom;
Y is a N atom or CH group or substituted C atom;
n is zero or the integer 1;
$Alk^1$ is an optionally substituted aliphatic or heteroaliphatic chain $L^1$ is a covalent bond or a linker atom or group;
$Cy^1$ is a hydrogen atom or an optionally substituted cycloaliphatic, polycycloaliphatic, heterocycloaliphatic, polyheterocycloaliphatic, aromatic or heteroaromatic group;
Ar is an optionally substituted aromatic or heteroaromatic group;
and the salts, solvates, hydrates and N-oxides thereof;

Particular compounds of formula (1a) in which $Cy^1$ is an optionally substituted cycloaliphatic, polycycloaliphatic, heterocycloaliphatic, polyheterocycloaliphatic, aromatic or heteroaromatic group form a further aspect of the invention.

In another particular aspect of the invention and we provide a compound of formula (1b):

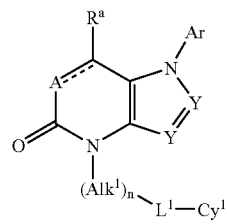

(1b)

wherein:
the dashed line represents an optional bond;
A is a —N= atom or a —N($R^b$)—, —C($R^b$)= or —C($R^b$)($R^c$)— group;
$R^a$, $R^b$ and $R^c$ is each independently a hydrogen atom or an optionally substituted $C_{1-6}$alkyl group;
each Y is independently a N atom or CH group or substituted C atom;
n is zero or the integer 1;

$Alk^1$ is an optionally substituted aliphatic or heteroaliphatic chain $L^1$ is a covalent bond or a linker atom or group;
$Cy^1$ is a hydrogen atom or an optionally substituted cycloaliphatic, polycycloaliphatic, heterocycloaliphatic, polyheterocycloaliphatic, aromatic or heteroaromatic group;
Ar is an optionally substituted aromatic or heteroaromatic group;
and the salts, solvates, hydrates and N-oxides thereof;
with the proviso that when the compound of formula (1b) is a compound of formula (1c):

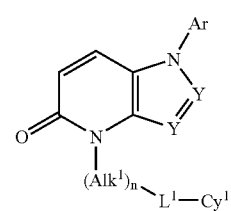

(1c)

in which
each Y is a N atom or a CH group, Ar is a 2,6-dichloro-4-trifluoromethylphenyl or 2-chloro-6-fluoro-4-trifluoromethylphenyl group, $L^1$ is a covalent bond, n is the integer 1 and $Alk^1$ is a —$CH_2$—, —$CH_2CH_2$—, —$CH_2CH_2CH_2$—, —$CH(CH_3)CH_2$—, —$CH_2CH=CH$—, —$CH_2CH=CCl$—, —$CH_2CC$— or —$CF_2$— chain then $Cy^1$ is other than a hydrogen atom; or in which
each Y is a N atom or a CH group, Ar is a 3-chloro-5-trifluoromethylpyridin-2-yl group, $L^1$ is a covalent bond, n is the integer 1 and $Alk^1$ is a —$CH_2$—, —$CH_2CH_2$— or —$CH_2CH_2CH_2$— chain then $Cy^1$ is other than a hydrogen atom; or in which
each Y is a N atom or a CH group, Ar is a 2,6-dichloro-4-trifluoromethylphenyl or 2-chloro-6-fluoro-4-trifluoromethylphenyl group, $L^1$ is a covalent bond and n is zero then $Cy^1$ is other than a cyclopropyl group; or in which
each Y is a N atom or a CH group, Ar is a 2,6-dichloro-4-trifluoromethylphenyl, 2-chloro-6-fluoro-4-trifluoromethylphenyl or 3-chloro-5-trifluoromethylpyridin-2-yl group, $L^1$ is a covalent bond and n is zero then $Cy^1$ is other than a hydrogen atom;
and with the further proviso that when the compound of formula (1b) is a compound of formula (1d):

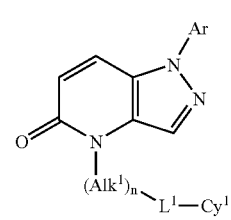

(1d)

in which:
$L^1$ is a covalent bond, n is the integer 1 and $Alk^1$ is a —$CH_2$— chain then Ar is other than a 3-methyl-5-trifluoromethylpyridin-2-yl, 5-trifluoromethylpyridin-2-yl, 3-trifluoromethylpyridin-2-yl, 3,5-difluoropyridin-2- yl, 3,5-dichloropyridin-2-yl or 2-chloro-4-trifluoromethylphenyl group.

Particular compounds of formula (1b) form a further aspect of the invention and we therefore provide a compound of formula and (1b'):

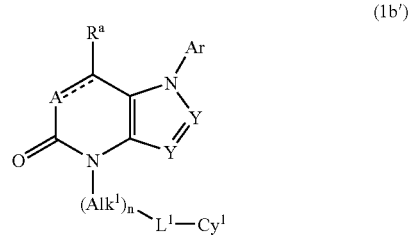

(1b')

wherein:
the dashed line represents an optional bond;
A is a —N= atom or a —N($R^b$)—, —C($R^b$)= or —C($R^b$)($R^c$)— group;
$R^a$, $R^b$ and $R^c$ is each independently a hydrogen atom or an optionally substituted $C_{1-6}$alkyl group;
each Y is independently a N atom or CH group or substituted C atom;
n is zero or the integer 1;
$Alk^1$ is an optionally substituted aliphatic or heteroaliphatic chain $L^1$ is a covalent bond or a linker atom or group;
$Cy^1$ an optionally substituted cycloaliphatic, polycycloaliphatic, heterocycloaliphatic, polyheterocycloaliphatic, aromatic or heteroaromatic group;
Ar is an optionally substituted aromatic or heteroaromatic group;
and the salts, solvates, hydrates and N-oxides thereof;
with the proviso that when the compound of formula (1b″) is a compound of formula (1c):

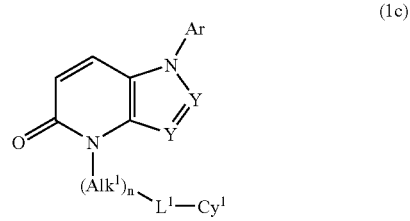

(1c)

in which
each Y is a N atom or a CH group, Ar is a 2,6-dichloro-4-trifluoromethylphenyl or 2-chloro-6-fluoro-4-trifluoromethylphenyl group, $L^1$ is a covalent bond and n is zero then $Cy^1$ is other than a cyclopropyl group.

It will be appreciated that in the following detailed description of the invention all references to formula (1b) are also references to formulae (1b') unless specifically stated otherwise.

It will be further appreciated that compounds of formulae (1a) and (1b) may have one or more chiral centres, and exist as enantiomers or diastereomers. The invention is to be understood to extend to all such enantiomers, diastereomers and mixtures thereof, including racemates. Formulae (1a) and (1b) and the formulae hereinafter are intended to represent all individual isomers and mixtures thereof, unless stated or shown otherwise. In addition, compounds of formulae (1a) and (1b) may exist as tautomers, for example keto ($CH_2C$=O)-enol (CH=CHOH) tautomers. Formulae (1a) and (1b) and the formulae hereinafter are intended to represent all individual tautomers and mixtures thereof, unless stated otherwise.

The following general terms as used herein have the stated meaning unless specifically described otherwise.

As used herein the term "alkyl" whether present as a group or part of a group includes straight or branched $C_{1-6}$alkyl groups, for example $C_{1-4}$alkyl groups such as methyl, ethyl, n-propyl, i-propyl, n-butyl, s-butyl, i-butyl or t-butyl groups. Similarly, the terms "alkenyl" or "alkynyl" are intended to mean straight or branched $C_{2-6}$alkenyl or $C_{2-6}$alkynyl groups such as $C_{2-4}$alkenyl or $C_{2-4}$alkynyl groups. Optional substituents which may be present on these groups include those optional substituents mentioned hereinafter in relation to $Alk^1$ when $Alk^1$ is an optionally substituted aliphatic chain.

The term halogen is intended to include fluorine, chlorine, bromine or iodine atoms.

The term "haloalkyl" is intended to include those alkyl groups just mentioned sustituted by one, two or three of the halogen atoms just described. Particular examples of such groups include —$CF_3$, —$CCl_3$, —$CHF_2$, —$CHCl_2$, —$CH_2F$ and —$CH_2Cl$ groups.

The term "alkoxy" as used herein is intended to include straight or branched $C_{1-6}$alkoxy e.g. $C_{1-4}$alkoxy such as methoxy, ethoxy, n-propoxy, i-propoxy, n-butoxy, s-butoxy, i-butoxy and t-butoxy. "Haloalkoxy" as used herein includes any of these alkoxy groups substituted by one, two or three halogen atoms as described above. Particular examples include —$OCF_3$, —$OCCl_3$, —$OCHF_2$, —$OCHCl_2$, —$OCH_2F$ and —$OCH_2Cl$ groups.

As used herein the term "alkylthio" is intended to include straight or branched $C_{1-6}$alkylthio, e.g. $C_{1-4}$alkylthio such as methylthio or ethylthio.

As used herein the term "alkylamino or dialkylamino" is intended to include the groups —$NHR^1$ and —$N(R^1)_2$ [where $R^1$ is an optionally substituted straight or branched alkyl group]. Where two $R^1$ groups are present these may be the same or different. In addition where two $R^1$ groups are present these may be joined together with the N atom to which they are attached to form an optionally substituted heterocycloalkyl group which may contain a further heteroatom or heteroatom containing group such as an —O— or —S— atom or —N($R^1$)— group. Particular examples of such optionally substituted heterocycloalkyl groups include optionally substituted pyrrolidinyl, piperidinyl, morpholinyl, thiomorpholinyl and N'—$C_{1-6}$alkyl-piperazinyl groups. The optional substituents which may be present on such heterocycloalkyl groups include those optional substituents as described hereinafter in relation to aliphatic chains.

When $Alk^1$ is present in compounds of formulae (1a) and (1b) as an optionally substituted aliphatic chain it may be an optionally substituted $C_{1-10}$aliphatic chain. Particular examples include optionally substituted straight or branched chain $C_{1-6}$alkylene, $C_{2-6}$alkenylene, or $C_{2-6}$alkynylene chains.

Particular examples of aliphatic chains represented by $Alk^1$ include optionally substituted —$CH_2$—, —$CH_2CH_2$—, —$CH(CH_3)CH_2$—, —$(CH_2)_2CH_2$—, —$(CH_2)_3CH_2$—, —$CH(CH_3)(CH_2)_2CH_2$—, —$CH_2CH(CH_3)CH_2$—, —$C(CH_3)_2CH_2$—, —$CH_2C(CH_3)_2CH_2$—, —$(CH_2)_2CH(CH_3)CH_2$—, —$CH(CH_3)CH_2CH_2$—, —$CH(CH_3)CH_2CH(CH_3)CH_2$—, —$CH_2CH(CH_3)CH_2CH_2$—, —$(CH_2)_2C(CH_3)_2CH_2$—, —$(CH_2)_4CH_2$—, —$(CH_2)_5CH_2$—, —CHCH—, —$CHCHCH_2$—, —$CH_2CHCH$—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$— or —(CH$_2$)$_2$CCH— chains.

Heteroaliphatic chains represented by Alk$^1$ in the compounds of formulae (1a) and (1b) include the aliphatic chains just described but with each additionally containing one, two, three or four heteroatoms or heteroatom-containing groups. Particular heteroatoms or groups include atoms or groups L$^2$ where L$^2$ is a linker atom or group. Each L$^2$ atom or group may interrupt the aliphatic group, or may be positioned at its terminal carbon atom to connect the group to an adjoining atom or group. Particular examples include optionally substituted —L$^2$CH$_2$—, —CH$_2$L$^2$—, —L$^2$CH(CH$_3$)—, —CH(CH$_3$)L$^2$—, —CH$_2$L$^2$CH$_2$—, —L$^2$CH$_2$CH$_2$—, —L$^2$CH$_2$CH(CH$_3$)—, —CH(CH$_3$)CH$_2$L$^2$—, —CH$_2$CH$_2$L$^2$—, —CH$_2$L$^2$CH$_2$CH$_2$—, —CH$_2$L$^2$CH$_2$CH$_2$L$^2$—, —(CH$_2$)$_2$L$^2$CH$_2$—, —(CH$_2$)$_3$L$^2$CH$_2$—, —L$^2$(CH$_2$)$_2$CH$_2$—, —L$^2$CH$_2$CHCH—, —CHCHCH$_2$L$^2$— and —(CH$_2$)$_2$L$^2$CH$_2$CH$_2$— chains.

When L$^2$ is present in heteroaliphatic chains as a linker atom or group it may be any divalent linking atom or group. Particular examples include —O— or —S— atoms or —C(O)—, —C(O)O—, —OC(O)—, —C(S)—, —S(O)—, —S(O)$_2$—, —N(R$^2$)— [where R$^2$ is a hydrogen atom or a straight or branched alkyl group], —N(R$^2$)O—, —N(R$^2$)N—, —CON(R$^2$)—, —OC(O)N(R$^2$)—, —CSN(R$^2$)—, —N(R$^2$)CO—, —N(R$^2$)C(O)O—, —N(R$^2$)CS—, —S(O)$_2$N(R$^2$)—, —N(R$^2$)S(O)$_2$—, —N(R$^2$)CON(R$^2$)—, —N(R$^2$)CSN(R$^2$)— or —N(R$^2$)SO$_2$N(R$^2$)— groups. Where L$^2$ contains two R$^2$ groups these may be the same or different.

The optional substituents which may be present on aliphatic or heteroaliphatic chains represented by Alk$^1$ include one, two, three or more substituents where each substituent may be the same or different and is selected from halogen atoms, e.g. fluorine, chlorine, bromine or iodine atoms, or —OH, —CO$_2$H, —CO$_2$R$^4$ [where R$^4$ is an optionally substituted straight or branched C$_{1-6}$alkyl group], e.g. —CO$_2$CH$_3$ or —CO$_2$C(CH$_3$)$_3$, —CONHR$^4$, e.g. CONHCH$_3$, —CON(R$^4$)$_2$, e.g. —CON(CH$_3$)$_2$, —COR$^4$, e.g. —COCH$_3$, C$_{1-6}$alkoxy, e.g. methoxy or ethoxy, haloC$_{1-6}$alkoxy, e.g. trifluoromethoxy or difluoromethoxy, thiol (—SH), —S(O)R$^4$, e.g. —S(O)CH$_3$, —S(O)$_2$R$^4$, e.g. —S(O)$_2$CH$_3$, C$_{1-6}$alkylthio e.g. methylthio or ethylthio, amino, —NHR$^4$, e.g. —NHCH$_3$ or —N(R$^4$)$_2$, e.g. —N(CH$_3$)$_2$ groups. Where two R$^4$ groups are present in any of the above substituents these may be the same or different.

In addition when two R$^4$ alkyl groups are present in any of the optional substituents just described these groups may be joined, together with the N atom to which they are attached, to form a heterocyclic ring. Such heterocyclic rings may be optionally interrupted by a further heteroatom or heteroatom containing group selected from —O—, —S—, —N(R$^4$)—, —C(O)— or —C(S)— groups. Particular examples of such heterocyclic rings include piperidinyl, pyrazolidinyl, morpholinyl, thiomorpholinyl, pyrrolidinyl, imidazolidinyl and piperazinyl rings.

When L$^1$ is present in compounds of formulae (1a) and (1b) as a linker atom or group it may be any such atom or group as hereinbefore described in relation to L$^2$ linker atoms and groups.

Optionally substituted cycloaliphatic groups represented by the group Cy$^1$ in compounds of the invention include optionally substituted C$_{3-10}$cycloaliphatic groups. Particular examples include optionally substituted C$_{3-10}$cycloalkyl, e.g. C$_{3-7}$cycloalkyl or C$_{3-10}$cycloalkenyl, e.g C$_{3-7}$cycloalkenyl groups.

Optionally substituted heterocycloaliphatic group represented by the group Cy$^1$ include optionally substituted C$_{3-10}$heterocycloaliphatic group. Particular examples include optionally substituted C$_{3-10}$heterocycloalkyl, e.g. C$_{3-7}$heterocycloalkyl or C$_{3-10}$heterocycloalkenyl, e.g. C$_{3-7}$heterocycloalkenyl groups, each of said groups containing one, two, three or four heteroatoms or heteroatom containing groups L$^4$ in place of or in addition to the ring carbon atoms where L$^4$ is an atom or group as previously defined for L$^2$.

Optionally substituted polycycloaliphatic groups represented by the group Cy$^1$ include optionally substituted C$_{7-10}$bi- or tricycloalkyl or C$_{7-10}$bi- or tricycloalkenyl groups. Optionally substituted heteropolycycloaliphatic groups represented by the group Cy$^1$ include optionally substituted C$_{7-10}$bi- or tricycloalkyl or C$_{7-10}$bi- or tri-cycloalkenyl groups containing one, two, three, four or more L$^4$ atoms or groups in place of or in addition to the ring carbon atoms.

Particular examples of cycloaliphatic, polycycloaliphatic, heterocycloaliphatic and heteropolycycloaliphatic groups represented by the group Cy$^1$ include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, dihydrofuranyl, tetrahydrofuranyl, tetrahydropyranyl, dihydrothiophenyl, tetrahydrothiophenyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, 5,6-dihydro-2(1H)-pyrazinone, tetrahydropyrimidinyl, thiazolinyl, thiazolidinyl, pyranyl, e.g. 2- or 4-pyranyl, piperidinyl, homopiperidinyl, heptamethyleneiminyl, piperidinone, 1,4-dioxanyl, morpholinyl, morpholinone, 1,4-dithianyl, thiomorpholinyl, piperazinyl, homopiperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, 1,3,5-oxadiazinyl, dihydroisothiazolyl, dihydroisothiazole 1,1-dioxide , e.g. 2,3-dihydroisothiazole 1,1-dioxide, dihydropyrazinyl and tetrahydropyrazinyl groups.

The optional substituents which may be present on the cycloaliphatic, polycycloaliphatic, heterocycloaliphatic or heteropolycycloaliphatic groups represented by the group Cy$^1$ include one, two, three or more substituents selected from halogen atoms, or C$_{1-6}$alkyl, e.g. methyl or ethyl, haloC$_{1-6}$alkyl, e.g. halomethyl or haloethyl such as difluoromethyl or trifluoromethyl, optionally substituted by hydroxyl, e.g. —C(OH)(CF$_3$)$_2$, C$_{1-6}$alkoxy, e.g. methoxy or ethoxy, haloC$_{1-6}$alkoxy, eg. halomethoxy or haloethoxy such as difluoromethoxy or trifluoromethoxy, thiol, C$_{1-6}$alkylthiol, e.g. methylthiol or ethylthiol, carbonyl (=O), thiocarbonyl (=S), imino (=NR$^{4a}$) [where R$^{4a}$ is an —OH group or a C$_{1-6}$alkyl group], or —(Alk$^3$)$_v$R$^5$ groups in which Alk$^3$ is a straight or branched C$_{1-3}$alkylene chain, v is zero or the integer 1 and R$^5$ is a C$_{3-8}$cycloalkyl, —OH, —SH, —N(R$^6$)(R$^7$) [in which R$^6$ and R$^7$ is each independently selected from a hydrogen atom or an optionally substituted alkyl or C$_{3-8}$cycloalkyl group], —OR$^6$, —SR$^6$, —CN, —NO$_2$, —CO$_2$R$^6$, —SOR$^6$, —SO$_2$R$^6$, —SO$_3$R$^6$, —OCO$_2$R$^6$, —C(O)R$_6$, —OC(O)R$^6$, —C(S)R$^6$, —C(O)N(R$^6$)(R$^7$), —OC(O)N(R$^6$)(R$^7$), —N(R$^6$)C(O)R$^7$, —C(S)N(R$^6$)(R$^7$), —N(R$^6$)C(S)R$^7$, —SO$_2$N(R$^6$)(R$^7$), —N(R$^6$)SO$_2$R$^7$, —N(R$^6$)C(O)N(R$^7$)(R$^8$) [where R$^8$ is as defined for R$^6$], —N(R$^6$)C(S)N(R$^7$)(R$^8$), —N(R$^6$)SO$_2$N(R$^7$)(R$^8$) or an optionally substituted aromatic or heteroaromatic group.

Particular examples of Alk$^3$ chains include —CH$_2$—, —CH$_2$CH$_2$—, —CH$_2$CH$_2$CH$_2$— and —CH(CH$_3$)CH$_2$— chains.

When R$^5$, R$^6$, R$^7$ and/or R$^8$ is present as a C$_{3-8}$cycloalkyl groups it may be for example a cyclopropyl, cyclobutyl, cyclopentyl or cyclohexyl group. Optional substituents which may be present on such groups include for example one, two or three substituents which may be the same or different selected from halogen atoms, for example fluorine, chlorine, bromine or iodine atoms, or hydroxy or C$_{1-6}$alkoxy, e.g. methoxy, ethoxy or i-propoxy groups.

When the groups R$^5$ and R$^7$ or R$^7$ and R$^8$ are both alkyl groups these groups may be joined, together with the N atom to which they are attached, to form a heterocyclic ring. Such heterocyclic rings may be optionally interrupted by a further heteroatom or heteroatom containing group selected from —O—, —S—, —N(R$^7$)—, —C(O)— or —C(S)— groups. Particular examples of such heterocyclic rings include piperidinyl, pyrazolidinyl, morpholinyl, thiomorpholinyl, pyrrolidinyl, imidazolidinyl and piperazinyl rings.

When R$^5$ is an optionally substituted aromatic or heteroaromatic group it may be any such group as described hereinafter in relation to Cy$^1$.

Additionally, when the group Cy$^1$ is a heterocycloaliphatic or heteropolycycloaliphatic group containing one or more nitrogen atoms each nitrogen atom may be optionally substituted by a group —(L$^5$)$_p$(Alk$^4$)$_q$R$^9$ in which L$^5$ is a —C(O)—, —C(O)O—, —C(S)—, —S(O)$_2$—, —CON(R$^6$)— or —SO$_2$N(R$^6$)—; p is zero or the integer 1; Alk$^4$ is an optionally substituted aliphatic or heteroaliphatic chain; q is zero or the integer 1; and R$^9$ is a hydrogen atom or an optionally substituted cycloaliphatic, heterocycloaliphatic, polycycloaliphatic, heteropolycycloaliphatic, aromatic or heteroaromatic group as herein described in relation to Cy$^1$.

When Alk$^4$ is present as an aliphatic or heteroaliphatic chain it may be for example any aliphatic or heteroaliphatic chain as hereinbefore described for Alk$^1$.

Optionally substituted aromatic groups represented by the groups Cy$^1$ include for example monocyclic or bicyclic fused ring C$_{6-12}$aromatic groups, such as phenyl, 1- or 2-napthyl, 1- or 2-tetrahydronapthyl, indanyl or indenyl groups.

Heteroaromatic groups represented by the groups Cy$^1$ include for example C$_{1-9}$heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N-C$_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,5-oxadiazolyl, 1,3,4-oxadiazolyl, 1,3,4-thiadiazolyl, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, benzothienyl, [2,3-dihydro]benzothienyl, benzotriazolyl, indolyl, indolinyl, indazolinyl, benzimidazolyl, imidazo[1,2-a]pyridyl, benzothiazolyl, benzoxazolyl, benzisoxazolyl, benzopyranyl, [3,4-dihydro]benzopyranyl, quinazolinyl, quinoxalinyl, naphthyridinyl, imidazo[1,5-a]pyridinyl, imidazo[1,5-a]pyrazinyl, imidazo[1,5-c]pyrimidinyl, pyrido[3,4-b]pyridyl, pyrido[3,2-b]pyridyl, pyrido[4,3-b]pyridyl, quinolinyl, isoquinolinyl, phthalazinyl, tetrazolyl, 5,6,7,8-tetrahydroquinolinyl, 5,6,7,8-tetrahydroisoquinolinyl, imidyl, e.g. succinimidyl, phthalimidyl or naphthalimidyl such as 1,8-naphthalimidyl, pyrazolo[4,3-d]pyrimidinyl, furo[3,2-d]pyrimidinyl, thieno[3,2-d]pyrimidinyl, pyrrolo[3,2-d]pyrimidinyl, pyrazolo[3,2-b]pyridinyl, furo[3,2-b]pyridinyl, thieno[3,2-b]pyridinyl, pyrrolo[3,2-b]pyridinyl, thiazolo[3,2-a]pyyridinyl, pyrido[1,2-a]pyrimidinyl, tetrahydroimidazo[1,2-a]pyrimidinyl and dihydroimidazo[1,2-a]pyrimidinyl groups.

Optional substituents which may be present on aromatic or heteroaromatic groups represented by the group Cy$^1$ include one, two, three or more substituents, each selected from an atom or group R$^{10}$ in which R$^{10}$ is R$^{10a}$ or —L$^6$Alk$^5$(R$^{10a}$)$_r$, where R$^{10a}$ is a halogen atom, or an amino (—NH$_2$), substituted amino, nitro, cyano, hydroxyl (—OH), substituted hydroxyl, formyl, carboxyl (—CO$_2$H), esterified carboxyl, thiol (—SH), substituted thiol, —COR$^{11}$ [where R$^{11}$ is an —L$^6$Alk$^3$(R$^{10a}$)$_r$, aryl or heteroaryl group], —CSR$^{11}$, —SO$_3$H, —SOR$^{11}$, —SO$_2$R$^{11}$, —SO$_3$R$^{11}$, —SO$_2$NH$_2$, —SO$_2$NHR$^{11}$, —SO$_2$N(R$^{11}$)$_2$, —CONH$_2$, —CSNH$_2$, —CONHR$^{11}$, —CSNHR$^{11}$, —CON(R$^{11}$)$_2$, —CSN(R$^{11}$)$_2$, —N(R$^{12}$)SO$_2$R$^{11}$ [where R$^{12}$ is a hydrogen atom or a straight or branched alkyl group], —N(SO$_2$R$^{11}$)$_2$, —N(R$^{12}$)SO$_2$NH$_2$, —N(R$^{12}$)SO$_2$NHR$^{11}$, —N(R$^{12}$)SO$_2$N(R$^{11}$)$_2$, —N(R$^{12}$)COR$^{11}$, —N(R$^{12}$)CONH$_2$, —N(R$^{12}$)CONHR$^{11}$, —N(R$^{12}$)CON(R$^{11}$)$_2$, —N(R$^{12}$)CSNH$_2$, —N(R$^{12}$)CSNHR$^{11}$, —N(R$^{12}$)CSN(R$^{11}$)$_2$, —N(R$^{12}$)CSR$^{11}$, —N(R$^{12}$)C(O)OR$^{11}$, —SO$_2$NHet$^1$ [where —NHet$^1$ is an optionally substituted C$_{5-7}$cyclicamino group optionally containing one or more other —O— or —S— atoms or —N(R$^{12}$)—, —C(O)— or —C(S)— groups], —CONHet$^1$, —CSNHet$^1$, —N(R$^{12}$)SO$_2$NHet$^1$, —N(R$^{12}$)CONHet$^1$, —N(R$^{12}$)CSNHet$^1$, —SO$_2$N(R$^{12}$)Het [where —Het is an optionally substituted monocyclic C$_{5-7}$carbocyclic group optionally containing one or more other —O— or —S— atoms or —N(R$^{12}$)—, —C(O)—, —S(O)— or —S(O)$_2$— groups], —Het, —CON(R$^{12}$)Het, —CSN(R$^{12}$)Het, —N(R$^{12}$)CON(R$^{12}$)Het, —N(R$^{12}$)CSN(R$^{12}$)Het, N(R$^{12}$)SO$_2$N(R$^{12}$)Het, aryl or heteroaryl groups; L$^6$ is a covalent bond or a linker atom or group as hereinbefore defined for L$^2$; Alk$^5$ is an optionally substituted straight or branched C$_{1-6}$alkylene, C$_{2-6}$alkenylene or C$_{2-6}$alkynylene chain, optionally interrupted by one, two or three —O— or —S— atoms or —S(O)$_n$— [where n is an integer 1 or 2] or —N(R$^{12}$)— e.g. —N(CH$_3$)— groups; and r is zero or the integer 1, 2, or 3. It will be appreciated that when two R$^{11}$ or R$^{12}$ groups are present in one of the above substituents the R$^{11}$ and R$^{12}$ groups may be the same or different.

When in the group —L$^6$Alk$^5$(R$^{10a}$)$_r$, r is an integer 1, 2 or 3, it is to be understood that the substituent or substituents R$^{10a}$ may be present on any suitable carbon atom in —Alk$^5$. Where more than one R$^{10a}$ substituent is present these may be the same or different and may be present on the same or different atom in —Alk$^5$. Clearly, when r is zero and no substituent R$^{10a}$ is present the alkylene, alkenylene or alkynylene chain represented by Alk$^5$ becomes an alkyl, alkenyl or alkynyl group.

When R$^{10a}$ is a substituted amino group it may be for example a group —NHR$^{11}$ [where R$^{11}$ is as defined above] or a group —N(R$^{11}$)$_2$ wherein each R$^{11}$ group is the same or different.

When R$^{10a}$ is a halogen atom it may be for example a fluorine, chlorine, bromine, or iodine atom.

When $R^{10a}$ is a substituted hydroxyl or substituted thiol group it may be for example a group —$OR^{11}$ or a —$SR^{12}$ group respectively.

Esterified carboxyl groups represented by the group $R^{10a}$ include groups of formula —$CO_2Alk^6$ wherein $Alk^6$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^6$ group include $R^{10a}$ atoms and groups as described above.

When $Alk^5$ is present in or as a substituent it may be for example a —$CH_2$—, —$CH(CH_3)$—, —$C(CH_3)_2$—, —$CH_2CH_2$—, —$CH_2CH_2CH_2$—, —$CH(CH_3)CH_2$—, $CH_2CH_2CH_2CH_2$—, —$CH_2CH(CH_3)CH_2$—, —$CH(CH_3)CH_2CH_2$—, —$C(CH_3)_2CH_2$—, —CH=CH—, —CH=CCH_2—, —CH_2C=CH—, —CH=CHCH_2—, —CH_2CH=CHCH_2—, —CH_2CH_2CH=CH_2—, —CC—, —CCCH_2—, —CH_2CC—, —CCCH_2CH_2—, —CH_2CCCH_2— or —CH_2CH_2CC— chain, optionally interrupted by one, two, or three —O— or —S—, atoms or —S(O)—, —S(O)_2— or —N($R^{12}$)—, e.g. —N($CH_3$)— groups. The aliphatic chains represented by $Alk^5$ may be optionally substituted by one, two or three halogen atoms in addition to any $R^{10a}$ groups that may be present.

Aryl or heteroaryl groups represented by the groups $R^{10a}$ or $R^{11}$ include mono- or bicyclic optionally substituted $C_{6-12}$ aromatic or $C_{1-9}$ heteroaromatic groups as described above for the group $Cy^1$. The aromatic and heteroaromatic groups may be attached to the group $Cy^1$ in compounds of formula (1) by any carbon or hetero e.g. nitrogen atom as appropriate.

It will be appreciated that when —$NHet^1$ or —Het forms part of a substituent $R^{10}$ the heteroatoms or heteroatom containing groups that may be present within the ring —$NHet^1$ or —Het take the place of carbon atoms within the parent carbocyclic ring.

Thus when —$NHet^1$ or —Het forms part of a substituent $R^{10}$ each may be for example an optionally substituted pyrrolidinyl, imidazolidinyl, pyrazolidinyl, piperazinyl, morpholinyl, thiomorpholinyl, piperidinyl or thiazolidinyl group. Additionally Het may represent for example, an optionally substituted cyclopentyl or cyclohexyl group. Optional substituents which may be present on —$NHet^1$ include those substituents described above when $Cy^1$ is a heterocycloaliphatic group.

Particularly useful atoms or groups represented by $R^{10}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, or thienyl, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxy-propylthio, $C_{1-6}$alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio or pyridylthio, $C_{3-7}$cycloalkyl, e.g. cyclobutyl, cyclopentyl, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino, ethylamino, —$CH(CH_3)NH_2$ or —$C(CH_3)_2NH_2$, halo$C_{1-6}$alkylamino, e.g. fluoro$C_{1-6}$alkylamino, e.g. —$CH(CF_3)NH_2$ or —$C(CF_3)_2 NH_2$, amino (—$NH_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, imido, such as phthalimido or naphthalimido, e.g. 1,8-naphthalimido, nitro, cyano, hydroxyl (—OH), formyl [HC(O)—], carboxyl (—$CO_2H$), —$CO_2Alk^6$ [where $Alk^6$ is as defined above], $C_{1-6}$alkanoyl e.g. acetyl, optionally substituted benzoyl, thiol (—SH), thio$C_{1-6}$alkyl, e.g. thiomethyl or thioethyl, sulphonyl (—$SO_3H$), $C_{1-6}$alkylsulphonyl, e.g. methylsulphonyl, aminosulphonyl (—$SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylamino-carbonyl, $C_{1-6}$dialkylamino$C_{1-6}$alkylaminocarbonyl, e.g. diethylaminoethyl-aminocarbonyl, aminocarbonylamino, $C_{1-6}$alkylaminocarbonylamino, e.g. methylaminocarbonylamino or ethylaminocarbonylamino, $C_{1-6}$dialkylamino-carbonylamino, e.g. dimethylaminocarbonylamino or diethylaminocarbonylamino, $C_{1-6}$alkylaminocabonyl$C_{1-6}$alkylamino, e.g. methylamino-carbonylmethylamino, aminothiocarbonylamino, $C_{1-6}$alkylaminothiocarbonyl-amino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)$NH_2$, $C_{1-6}$alkylsulphonyl-amino, e.g. methylsulphonylamino or ethylsulphonylamino, $C_{1-5}$dialkyl-sulphonylamino, e.g. dimethylsulphonylamino or diethylsulphonylamino, optionally substituted phenylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, benzothio, pyridylmethylthio or thiazolylmethylthio groups.

A further particularly useful group of substituents represented by $R^{10}$ when present on aromatic or heteroaromatic groups includes substituents of formula —$L^6Alk^5R^{10a}$ where $L^6$ is preferably a covalent bond or an —O— or —S— atom or —N($R^2$)—, —C(O)—, —C(O)O—, —O—C (O)—, —N($R^2$)CO—, —CON($R^2$)— or —N($R^2$)S(O)$_2$— group, $Alk^5$ is an optionally substituted $C_{1-6}$-alkyl group optionally interrupted by one or two —O— or —S— atoms or —N($R^{12}$)—, —C(O)—, —C(S)—, —CON($R^{12}$)— or —N($R^{12}$)CO— groups and $R^{10a}$ is an optionally substituted Het group as herein defined or an optionally substituted heteroaromatic group as hereinbefore described in relation to $Cy^1$.

Where desired, two $R^{10}$ substituents may be linked together to form a cyclic group such as a cyclic ether, e.g. a $C_{1-6}$alkylenedioxy group such as methylenedioxy or ethylenedioxy.

It will be appreciated that where two or more $R^{10}$ substituents are present, these need not necessarily be the same atoms and/or groups. In general, the substituent(s) may be present at any available ring position on the aromatic or heteroaromatic group represented by the group $Cy^1$.

When in compounds of formula (1a) X is a substituted —N— atom or in compounds of formulae (1a) or (1b) Y is a substituted C atom the substituents which may be present on the N or C atom include those $R^{10}$ atoms and groups as hereinbefore defined.

When Ar is present in compounds of formulae (1a) or (1b) as an optionally substituted aromatic or heteroaromatic group it may be any such group as hereinbefore described for $Cy^1$. Optional substituents which may be present include those $R^{10}$ atoms and groups as described in relation to $Cy^1$ aromatic and heteroaromatic groups.

One useful group of compounds according to the invention is that where Y is a CH group or a substituted C atom where the substituent on the C atom may in general be any $R^{10}$ atom or group as hereinbefore described or in particular a $R^{20}$ group as hereinafter defined.

A particularly useful group of compounds according to the invention is represented by the compounds of formula (1a).

An especially useful group of compounds according to the invention has the formula (2a):

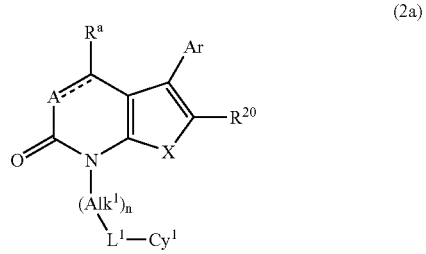

(2a)

in which
$R^{20}$ is a hydrogen atom or an atom or group $R^{10}$ as hereinbefore defined;
the dashed line, A, $R^a$, $Alk^1$, n, $L^1$, $Cy^1$, X and Ar are as generally and specifically defined previously;
and the salts, solvates, hydrates and N-oxides thereof.

In general in compounds of formula (1a), (1b) and (2a) $R^a$ is preferably a hydrogen atom or a $C_{1-4}$alkyl group, especially a methyl, ethyl, n-propyl or i-propyl group. Most preferably $R^a$ is a methyl group or most especially a hydrogen atom.

In one particularly preferred class of compounds of formula (1a), (1b) and (2a) the dashed line represents a bond and A is a —C($R^b$)═ group. In this class of compounds $R^b$ is preferably a $C_{1-4}$alkyl group, especially a methyl, ethyl, n-propyl or i-propyl group. Most preferably $R^b$ is a methyl group or most especially a hydrogen atom.

In one preferred class of compounds of formulae (1a) and (2a) X is a —O— or —S— atom, most preferably a —S— atom.

In another preferred group of compounds of formulae (1a), (1b) and (2a) n is zero.

In another preferred group of compounds of formulae (1a), (1b) and (2a) n is the integer 1 and $Alk^1$ is preferably an optionally substituted $C_{1-6}$alkylene chain, especially an optionally substituted —CH$_2$—, —CH$_2$CH$_2$—, —CH$_2$CH$_2$CH$_2$—, —CH(CH$_3$)CH$_2$— or —CH$_2$CH (CH$_3$)— chain, most especially a —CH$_2$— or —CH$_2$CH$_2$— chain.

In compounds of formula (2a) and in general in compounds of the invention $L^1$ is preferably a covalent bond or an —O— or —S— atom or an —N($R^2$)—, especially —NH— or —N(CH$_3$)—, —C(O)—, —C(S)—, —S(O)— or —S(O)$_2$— group. Most preferably $L^1$ is a covalent bond or an —O— or —S— atom or —NH— group. $L^1$ is most especially preferably is a covalent bond.

In compounds of formula (2a) and in general in compounds of the invention $Cy^1$ is preferably an optionally substituted cycloaliphatic, aromatic or heteroaromatic group as hereinbefore generally and particularly defined.

Particularly preferred $Cy^1$ optionally substituted cycloaliphatic groups include optionally substituted $C_{3-7}$cycloalkyl groups, especially cyclopropyl, cyclobutyl, cyclopentyl or cyclohexyl groups.

Particularly preferred optional substituents which may be present on $Cy^1$ optionally substituted cycloaliphatic groups include halogen atoms, especially fluorine, chlorine or bromine atoms, or $C_{1-6}$alkyl groups, especially $C_{1-3}$alkyl groups, most especially a methyl group, or a halo$C_{1-6}$alkyl group, especially a fluoro$C_{1-6}$alkyl group, most especially a —CF$_3$ group, or a $C_{1-6}$alkoxy, especially methoxy, ethoxy, propxy or i-propoxy group, or a halo$C_{1-6}$alkoxy, especially a fluoro$C_{1-6}$alkoxy, most especially a —OCF$_3$ group, or a cyano (—CN), esterified carboxyl, especially —CO$_2$CH$_3$ or —O$_2$C(CH$_3$)$_3$, nitro (—NO$_2$), amino (—NH$_2$), substituted amino, especially —NHCH$_3$ or —N(CH$_3$)$_2$, —C(O)$R^6$, especially —C(O)CH$_3$, or —N($R^6$)C(O)$R^7$, especially —NHCOCH$_3$ group.

Particularly preferred $Cy^1$ aromatic groups include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur or nitrogen atoms. Particularly preferred optionally substituted monocyclic heteroaromatic groups include optionally substituted furyl, thienyl, pyrrolyl, oxazolyl, thiazolyl, pyridyl, pyrimidinyl or triazinyl group.

Particularly preferred optional substituents which may be present on $Cy^1$ aromatic or heteroaromatic groups include atoms or groups —$R^{10a}$ or —$L^6Alk^5(R^{10a})_r$ as hereinbefore defined. Particularly useful optional substituents include halogen atoms, especially fluorine, chlorine or bromine atoms, or $C_{1-6}$alkyl groups, especially $C_{1-3}$alkyl groups, most especially a methyl group, or a halo$C_{1-6}$alkyl group, especially a fluoroC$_{1-6}$alkyl group, most especially a —CF$_3$ group, or a C$_{1-6}$alkoxy, especially methoxy, ethoxy, propxy or i-propoxy group, or a haloC$_{1-6}$alkoxy, especially a fluoroC$_{1-6}$alkoxy, most especially a —OCF$_3$ group, or a cyano (—CN), carboxyl (—CO$_2$H), esterified carboxyl (—CO$_2$Alk$^6$), especially —CO$_2$CH$_3$, —CO$_2$CH$_2$CH$_3$, or —CO$_2$C(CH$_3$)$_3$, nitro (—NO$_2$), amino (—NH$_2$), substituted amino, especially —NHCH$_3$ or —N(CH$_3$)$_2$, —COR$^{11}$, especially —COCH$_3$, or —N(R$^{12}$)COR$^{11}$, especially —NHCOCH$_3$ group.

Further preferred optional substituents which may be present on Cy$^1$ aromatic or heteroaromatic groups include groups of formula —L$^6$Alk$^5$(R$^{10a}$)$_r$ in which r is the integer 1, L$^6$ is a covalent bond or an —O— or —S— atom or a —N(R$^2$)—, especially —NH— or —N(CH$_3$)—, —C(O)—, —C(S)—, —C(O)O—, —OC(O)—, —N(R$^2$)CO—, especially —NHCO—, or —CON(R$^2$)—, especially —CHNH- group, Alk$^5$ is a C$_{1-6}$alkyl chain, especially a —CH$_2$—, —CH$_2$CH$_2$—, —CH$_2$CH$_2$CH$_2$— or —CH$_2$CH$_2$CH$_2$CH$_2$— chain and R$^{10a}$ is a substituted hydroxyl group, especially a —OCH$_3$, —OCH$_2$CH$_3$ or —OCH(CH$_3$)$_2$ group or a substituted amino group, especially a —N(CH$_3$)$_2$ or —N(CH$_2$CH$_3$)$_2$ group or a —Het group, especially an optionally substituted monocyclic C$_{5-7}$carbocyclic group containing one, two or three —O—, —S—, —N(R$^{12}$)—, especially —NH— or —N(CH$_3$)— or —C(O)— groups within the ring structure as previously described, most especially an optionally substituted pyrrolidinyl, imidazolidinyl, piperidinyl, e.g. N-methylpiperidinyl, morpholinyl, thiomorpholinyl or piperazinyl group or R$^{10a}$ is an optionally substituted heteroaromatic group, especially a five- or six-membered monocyclic heteroaromatic group containing one, two, three or four heteroatoms selected from oxygen, sulphur or nitrogen atoms, such as optionally substituted pyrrolyl, furyl, thienyl, imidazolyl, triazolyl, pyridyl, pyrimidinyl, triazinyl, pyridazinyl, or pyrazinyl group. Particularly preferred optional substituents on the —Het groups just described include hydroxyl (—OH) and carboxyl (—CO$_2$H) groups or those preferred optional substituents just described in relation to the group Cy$^1$.

In one preferred class of compounds of formula (2a) R$^{20}$ is an atom or group —R$^{10a}$ or L$^6$Alk$^6$(R$^{10a}$)$_r$ as hereinbefore defined. Preferably R$^{20}$ is a preferred atom or group as just defined for Cy$^1$. In one particularly preferred class of compounds of formula (2a) R$^{20}$ is a hydrogen atom or a carboxyl (—CO$_2$H), esterified carboxyl (—CO$_2$Alk$^6$), especially —CO$_2$CH$_3$, —CO$_2$CH$_2$CH$_3$, or —CO$_2$C(CH$_3$)$_3$, —CN, —NH$_2$, —CONH$_2$, —CONHR$^{11}$, —N(R$^{12}$)SO$_2$R$^{11}$, —N(R$^{12}$)C(O)OR$^{11}$ or —O$_2$R$^{11}$ group.

In one particularly preferred group of compounds of formula (1), (1a) and (2a) Cy$^1$ is an optionally substituted phenyl group, especially a phenyl group optionally substituted by one, two or three optional substituents where at least one, and preferably two optional substituents are located ortho to the bond joining Cy$^1$ to the remainder of the compound of formula (1), (1a) or (2a). Particularly preferred ortho substituents include halogen atoms, especially fluorine or chlorine atoms, or C$_{1-3}$alkyl groups, especially methyl groups, C$_{1-3}$alkoxy groups, especially methoxy, haloC$_{1-3}$alkyl groups, especially —CF$_3$, haloC$_{1-3}$alkoxy groups, especially —OCF$_3$, or cyano (—CN), groups. In this class of compounds a second or third optional substituent when present in a position other than the ortho positions of the ring Cy$^1$ may be preferably an atom or group —R$^{10a}$ or —L$^6$Alk$^5$(R$^{10a}$)$_r$ as herein generally and particularly described.

Particularly preferred Ar aromatic groups include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur or nitrogen atoms. Particularly preferred optionally substituted monocyclic heteroaromatic groups include optionally substituted furyl, thienyl, pyrrolyl, oxazolyl, thiazolyl, pyridyl, pyrimidinyl or triazinyl group.

Particularly preferred optional substituents which may be present on Ar aromatic or heteroaromatic groups include atoms or groups —R$^{10a}$ or —L$^6$Alk$^5$(R$^{10a}$)$_r$ as hereinbefore defined. Particularly useful optional substituents include halogen atoms, especially fluorine, chlorine or bromine atoms, or C$_{1-6}$alkyl groups, especially C$_{1-3}$alkyl groups, most especially a methyl group, or a haloC$_{1-6}$alkyl group, especially a fluoroC$_{1-6}$alkyl group, most especially a —CF$_3$ group, or a C$_{1-6}$alkoxy, especially methoxy, ethoxy, propxy or i-propoxy group, or a haloC$_{1-6}$alkoxy, especially a fluoroC$_{1-6}$alkoxy, most especially a —OCF$_3$ group, or a cyano (—CN), esterified carboxyl, especially —CO$_2$CH$_3$ or —CO$_2$C(CH$_3$)$_3$, nitro (—NO$_2$), amino (—NH$_2$), substituted amino, especially —NHCH$_3$ or —N(CH$_3$)$_2$, —COR$^{11}$, especially —COCH$_3$, or —N(R$^{12}$)COR$^{11}$, especially —NHCOCH$_3$ group.

In one particularly preferred class of compounds of formula (2a) the dashed line is present, A is a —CH= group, R$^a$ is a hydrogen atom and X is a —S— atom.

A further particularly useful class of compounds according to the invention has the formula (1b) in which the dashed line is present, A is a —CH= group, R$^a$, Ar, Alk$^1$, n and L$^1$ are as defined for formula (1b), each Y is independently a CH group or substituted C atom and Cy$^1$ is an optionally substituted aromatic or heteroaromatic group Particularly useful compounds of the invention include:

Ethyl 6-oxo-3,7-diphenyl-6,7-dihydrothieno[2,3-b]pyridine-2-carboxylate;

Ethyl 7-cyclopropylmethyl-6-oxo-3-phenyl -6,7-dihydrothieno[2,3-b]pyridine-2-carboxylate;

Ethyl 6-oxo-3-phenyl-7-(3-thienyl)-6,7-dihydrothieno[2,3-b]pyridine-2-carboxylate;

Ethyl 3-(4-fluorophenyl)-6-oxo-7-phenyl-6,7-dihydrothieno[2,3-b]pyridine-2-carboxylate;

Ethyl 3-(2-methoxyphenyl)-6-oxo-7-phenyl-6,7-dihydrothieno[2,3-b]pyridine-2-carboxylate;

Ethyl 6-oxo-7-phenyl-3-(4-tolyl)-6,7-dihydrothieno[2,3-b]pyridine-2-carboxylate;

Ethyl 3-(3-methoxyphenyl)-6-oxo-7-phenyl-6,7-dihydrothieno[2,3-b]pyridine-2-carboxylate;

6-Oxo-3,7-diphenyl-N-(2-piperidinoethyl)-6,7-dihydrothieno[2,3-b]pyridine-2-carboxamide;

6-Oxo-3,7-diphenyl-6,7-dihydrothieno[2,3-b]pyridine-2-carbonitrile;

3,7-Diphenylthieno[2,3-b]pyridin-6(7H)-one;

Ethyl 3-(2,4-difluorophenyl)-7-[4-(4-methylpiperazin-1-yl)phenyl]-6-oxo-6,7-dihydrothieno[2,3-b]pyridine-2-carboxylate;

1,4-Diphenyl-1,4-dihydro-pyrrolo[3,2-b]pyridin-5-one;

Ethyl 7-(2-chlorophenyl)-6-oxo-3-phenyl-6,7-dihydrothieno[2,3-b]pyridine-2-carboxylate;

and the salts, solvates, hydrates and N-oxides thereof.

The compounds of the invention may be prepared by a number of processes as generally described below and more specifically in the Examples hereinafter. In the following process description, the symbols Ar, $Cy^1$, $Alk^1$, n, $L^1$, $R^a$, $R^b$, $R^c$, A, X and Y when used in the formulae depicted are to be understood to represent those groups described above in relation to formulae (1a) and (1b) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1999]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1a) or (1b) but clearly the description applies equally to the preparation of compounds of formula (2a).

Thus according to a further aspect of the invention a compound of formula (1a) in which Y is a substituted e.g. —$CO_2CH_2CH_3$ substituted C atom may be prepared according to the reactions set out in Scheme 1:

halogen atom, e.g. a chlorine, bromine or iodine atom or a sulphonyloxy group such as an alkylsulphonyloxy e.g. trifluoromethylsulphonyloxy or arylsulphonyloxy e.g. phenylsulphonyloxy group.

The reaction may be performed in the presence of a solvent, for example a substituted amide such as dimethylformamide, optionally in the presence of a base, for example an inorganic base such as sodium hydride, or an organic base such as an organic amine, e.g. a cyclic amine such as 1,5-diazabicyclo[4.3.0]non-5-ene or a resin bound organic amine such as resin bound 2-tert-butylimino-2-diethylamino-1,3-dimethyl-perhydro-1,3,2-diazaphosphorine (PS-BEMP), at an elevated temperature, for example 80 to 100° C.

In a further aspect of the invention a compound of formula (1a) in which, for example, $L^1$ is a covalent bond and n is zero may be prepared by the reaction of a compound of formula (7) with a boronic acid of formula $Cy^1B(OH)_2$. The reaction may be performed in an organic solvent, for example a halogenated hydrocarbon such as dichloromethane or dichloroethane in the presence of a copper reagent, for example a copper (II) reagent such as copper (II) acetate, optionally in the presence of an oxidant, for example 2,2,6,6-tetramethyl-1-piperidinyloxy or pyridine-N-oxide, optionally in the presence of a base, for example an organic amine such as an alkylamine, e.g. triethylamine or an

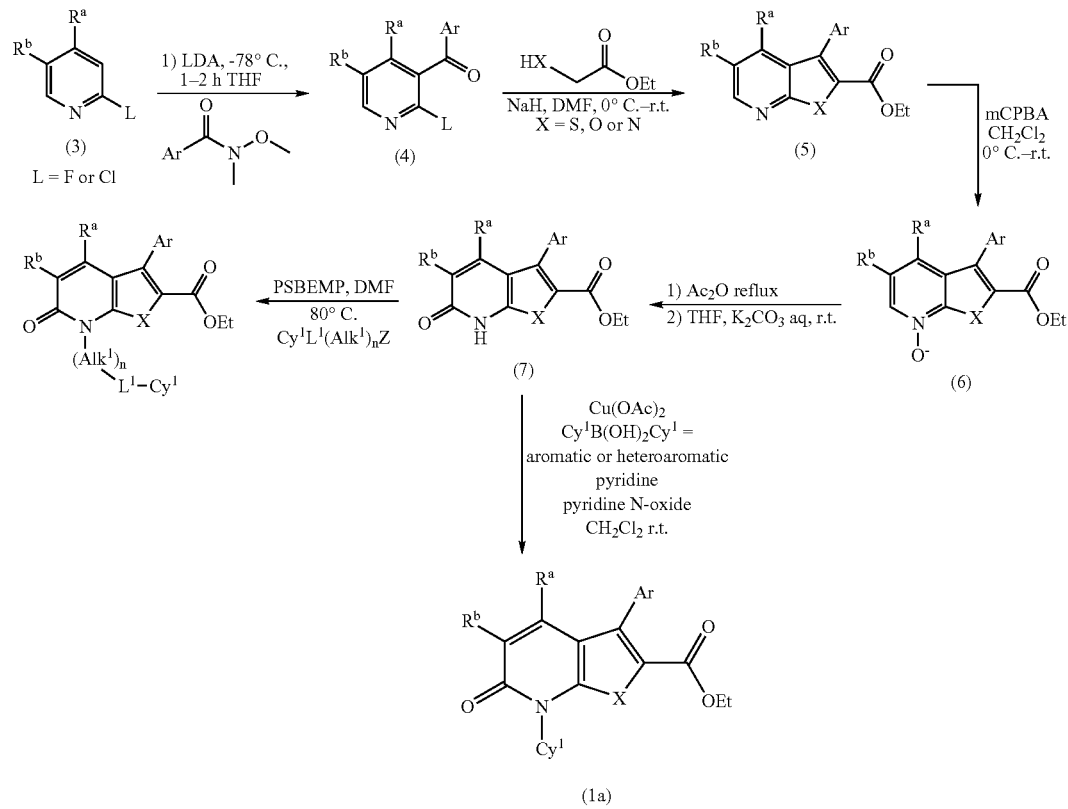

Thus a compound of formula (1a) in which Y is a substituted C atom may be prepared by reaction of a compound of formula (7) with an alkylating agent of formula $Cy^1L^1(Alk^1)_nZ$, where Z is a leaving group such as a aromatic amine, e.g. pyridine at a temperature from around ambient to the reflux temperature [see for example Chan, D. T. et al Tetrahedron Letters, 1998, 2933; Lam, P. Y. S. et al, Tetrahedron Letters, 2001, 3415]

Clearly the reactions just described may be used to prepare other compounds of the invention starting from intermediates of formula (7a) or (7b):

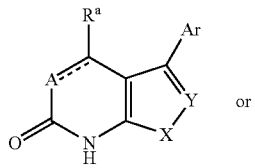
(7a)

or

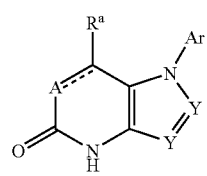
(7b)

for instance compounds of formula (7a) in which Y is a CH group.

Intermediates pyridinones of formula (7) may be prepared from pyridine N-oxides of formula (6) by sequential reaction with an anhydride, for example acetic anhydride at an elevated temperature, for example the reflux temperature followed by reaction with an inorganic base, for example a carbonate such as aqueous potassium carbonate in a solvent such as an ether for example a cyclic ether e.g. tetrahydrofuran at around ambient temperature.

Pyridine N-oxides of formula (6) may be formed from pyridines of formula (5) by standard methods of formation of N-oxides as described hereinafter.

Pyridines of formula (5) may be formed from 2-halopyridyl-(hetero)arylmethanones of formula (4) by reaction with a reagent of formula $HXCH_2CO_2R^{30}$ [where $R^{30}$ is a $C_{1-6}$alkyl group such as a methyl or ethyl group]. The reaction may be performed in the presence of a solvent such as a substituted amide for example dimethylformamide or an ether e.g. a cyclic ether such as tetrahydrofuran in the presence of a base, for example an inorganic base such as a hydride e.g. sodium hydride or an organic base such as 1,5-diazabicyclo[4.3.0]non-5-ene or a trialkylamine such as triethylamine at a temperature between about 0° C. and ambient temperature.

2-Halopyridyl-(hetero)arylmethanones of formula (4) may be prepared from 2-halopyridines of formula (3) by reaction with a base, for example a strong base such as lithium diisopropylamide or butyl lithium to form a 2-halopyridyl anion and quenching with a (hetero)aryl amide such as a Weinreb amide. The reaction may be performed in the presence of a solvent such as a substituted amide for example dimethylformamide or an ether e.g. a cyclic ether such as, at a temperature of around −78° C.

According to another aspect of the invention further compounds of formula (1a) may be prepared according to the reactions set out in Scheme 2.

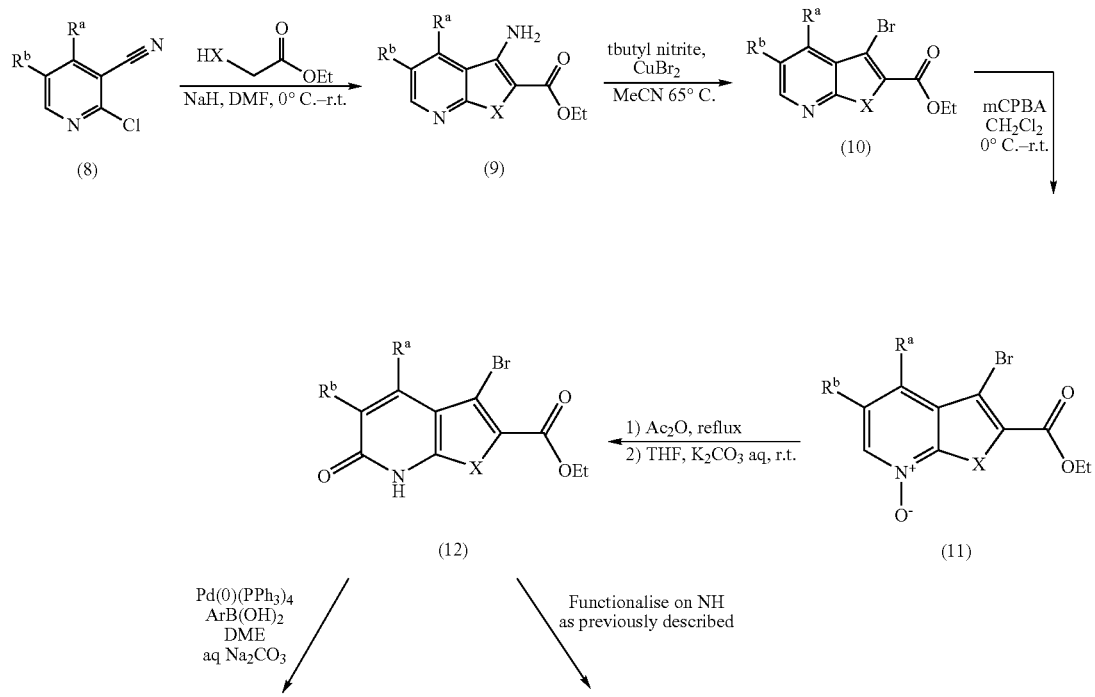

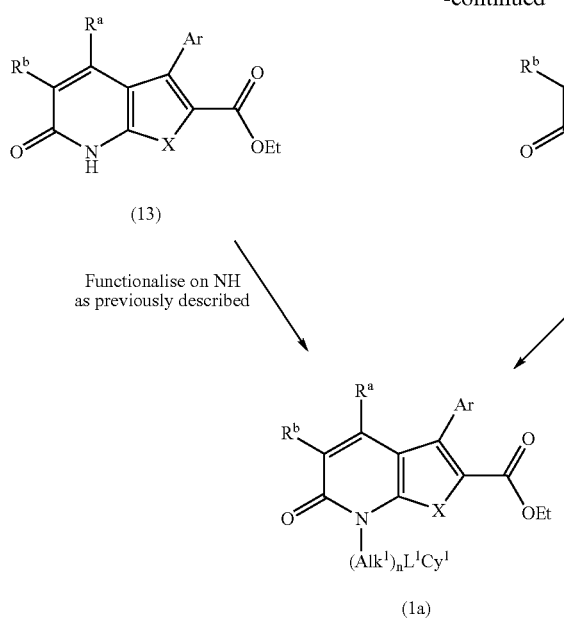

(13)

(14)

Functionalise on NH as previously described

Pd(0)(PPh₃)₄
ArB(OH)₂
DME
aq Na₂CO₃

(1a)

Thus further compounds of formula (1a) may be prepared from intermediates of formula (13), and intermediates of formula (14) may be prepared from intermediates of formula (12), by functionalisation at the 6-membered ring nitrogen according to the methods as previously described for the conversion of compounds of formula (7) to compounds of formula (1a).

Further compounds of formula (1a) may also be prepared from halogen substituted e.g. bromine substituted intermediates of formula (14), and intermediates of formula (13) may be prepared from halogen substituted e.g. bromine substituted intermediates of formula (12) by reaction with a boronic acid of formula ArB(OH)$_2$. The reaction may be performed in a solvent such as an acyclic ether, for example ethylene glycol dimethyl ether or a cyclic ether, for example tetrahydrofuran or an aromatic hydrocarbon, for example toluene in the presence of an inorganic catalyst such as a palladium catalyst e.g. tetrakis(triphenylphosphine) palladium (0) in the presence of a base, for example an aqueous inorganic base such as aqueous sodium, potassium or caesium carbonate at an elevated temperature, for example around 80° C.

Pyridinones of formula (12) and pyridine N-oxides of formula (11) may be prepared by the methods as hereinbefore described.

Halides, for example bromides, of formula (10) may be prepared by such well known methods as for example the Sandmeyer reaction. Thus for example a bromide of formula (10) may be prepared by treatment of an aryl amine of formula (9) with an alkyl nitrite, for example t-butyl nitrite and a copper salt, for example copper (II) bromide in the presence of a solvent, for example a nitrile such as acetonitrile at a temperature from about 0° to around 65° C.

Aryl amines of formula (9) may be prepared from halo nitrites of formula (8) by analogous methods to those used to prepare compounds of formula (5) as herein described.

Further 5–6 fused ring bicyclic heteroaromatic intermediates of formulae (15) and (17) may be prepared from intermediates of formula (4) by the methods shown in Scheme 3.

Scheme 3

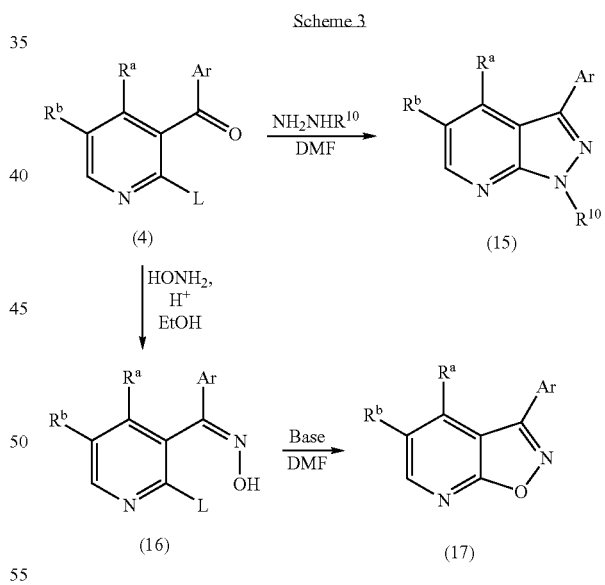

Thus pyrazolo[3,4-b]pyridines of formula (15) may be prepared by reaction of a 2-halopyridyl (or 2-halopyrimidinyl)-(hetero)arylmethanone of formula (4) with an optionally substituted hydrazine of formula R$^{10}$NHNH$_2$. The reaction may be performed in a solvent such as an amide for example a substituted amide e.g. dimethylformamide, at an elevated temperature, for example from about 60° C. to the reflux temperature.

Similarly intermediate isoxazolo[3,4-b]pyridines of formula (17) may be prepared by reaction of a 2-halopyridyl (or 2-halopyrimidinyl)-(hetero)arylmethanone of formula (4)

with hydroxylamine in the presence of an proton source for example hydrogen chloride in a solvent such as an alcohol, e.g. methanol or ethanol at a temperature from ambient to the reflux temperature to give an intermediate of formula (16) which may be cyclised to an intermediate of formula (17) by reaction with a base, for example an organic base such as 1,5-diazabicyclo[4.3.0]non-5-ene (DBU) or an inorganic base such as a hydride e.g. sodium hydride in a solvent such as an amide for example a substituted amide e.g. dimethylformamide or an ether such as a cyclic ether e.g. tetrahydrofuran at a temperature from about 0° C. to ambient temperature.

Further pyrrolo[3,2-b]pyrimidine intermediates of formula (20) may be prepared from intermediates of formula (18) by the methods shown in Scheme 4.

of an inorganic base such as a carbonate e.g. potassium or caesium carbonate in a solvent such as an aromatic amine e.g. pyridine [according to the method of Ishii, H. et al, J. Chem. Soc. Perkin Trans. 1, 1989, 2407]. Alternatively the reaction may be performed with a compound of formula Ar—L (in which L is a leaving group such as a halogen atom e.g. a bromine atom or a aryl sulfonate such as a triflate) in the presence of a catalyst such as a palladium catalyst e.g. palladium (ii) acetate in the presence of an iron catalyst e.g. 1,1'-bis(diphenylphosphino)ferrocene in a solvent such as an aromatic hydrocarbon e.g. toluene at an elevated temperature e.g. between 80° C. and the reflux temperature [according to the method of Mann, G. et al, J. Am. Chem. Soc., 1998, 120, 827–8].

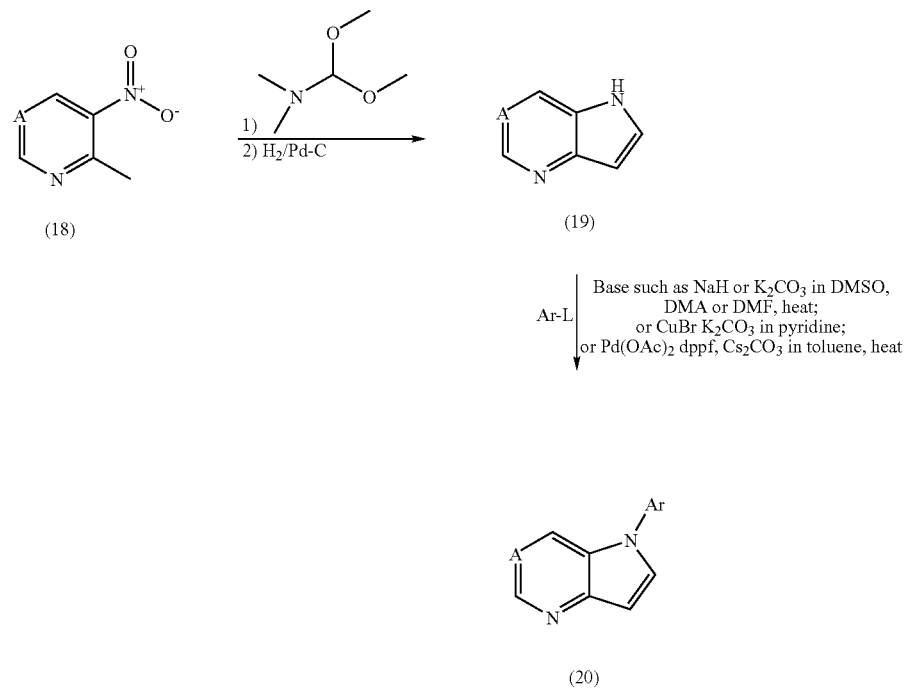

Thus a 1H-pyrrolo[3,2-b]pyridine (A=CH) or 1H-pyrrolo[3,2-b]pyrimidine (A=N) of formula (19) may be converted to an intermediate of formula (20) by reaction with a compound of formula Ar—L (in which L is a leaving group such as a halogen atom e.g. a fluorine, chlorine, bromine or iodine atom or a aryl sulfonate such as a triflate). The reaction may be performed in the presence of a base, for example a hydride such as sodium hydride or a carbonate such as potassium or caesium carbonate, in a solvent such as a sulfoxide e.g. dimethyl sulfoxide or an amide e.g. dimethylacetamide or dimethylformamide, at an elevated temperature e.g. from about 60° C. to 120° C. [according to the methods of Glamkowski, E. J. et al, J. Med. Chem., 1985, 28, 66 and Stabler, S. R. et al, Synth. Commun., 1994, 24, 123–29]. Alternatively the reaction may be performed with a compound of formula Ar—L (in which L is a leaving group such as a halogen atom e.g. a bromine atom or a aryl sulfonate such as a triflate) in the presence of a catalyst such as a copper catalyst e.g. copper (I) bromide in the presence Intermediates of formula (19) may be formed from nitropyridines (A=CH) or nitropyrimidines (A=N) of formula (18) by sequential reaction with a dialkoxymethyl-dimethyl-amine such as dimethoxymethyl-dimethyl-amine followed by catalytic reduction with a palladium catalyst such as palladium on carbon [according to the method of Mahadevan, I. et al, J. Heterocyclic Chem., 1992,29, 359–67].

Further 5–6 fused ring bicyclic heteroaromatic intermediates for use in the preparation of compounds of formula (1a) and (1b) may be prepared according to the methods of Japanese Patent Application JP9059276.

Such 5–6 fused ring bicyclic heteroaromatic intermediates of formula (15), (17), (19) and (20) as just described may be converted into further compounds of the invention by the particular methods as described above and general methods described below.

Further compounds of the invention in which A is a —N= atom may be prepared according to the methods shown in Scheme 5.

Scheme 5

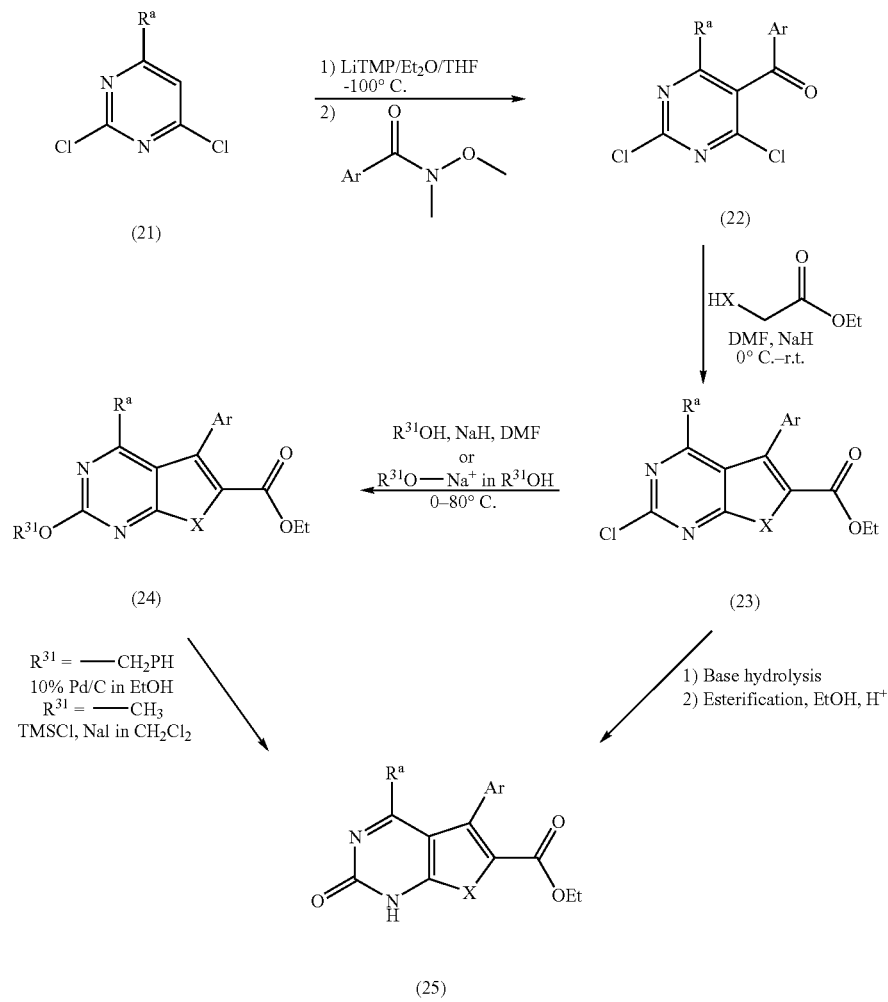

Thus an intermediate of formula (25) may be converted to a compound of the invention according to the methods as herein described for the conversion of compounds of formula (7) to compounds of formula (1a).

Intermediates of formula (25) may be prepared from intermediates of formula (24) by cleavage of an ether group. Thus when $R^{31}$ is a benzyl group it may be cleaved by such well known methods as catalytic reduction with hydrogen gas in the presence of a catalyst such as a palladium catalyst e.g. palladium on charcoal. When $R^{31}$ is an alkyl ether, e.g. a methyl ether it may be cleaved by reaction with a trialkyl-silyl halide such as trimethylsilyl chloride, optionally in the presence of an inorganic halide such as sodium iodide in a solvent such as a halogenated hydrocarbon e.g. dichloromethane or in a nitrile e.g. acetonitrile [according to the methods of Kundu, N. G. et al, J. Chem. Soc. Perkin Trans. I, 1990, 1822].

Intermediates of formula (25) may also be prepared from intermediates of formula (23) sequential by base hydrolysis, for example soudium or potassium hydroxide hydrolysis in a solvent such as an alcohol, e.g. methanol or ethanol at an elevated temperature, e.g. the reflux tempertute, followed by re-esterification by reaction with an acidified alcohol, e.g hydrogen chloride saturated ethanol at an elevated temperature, e.g. the reflux temperature.

Intermediates of formula (24) may be prepared from intermediates of formula (23) by reaction with an alkoxide, e.g. sodium methoxide or sodium benzyloxide in a solvent such as an alcohol, e.g. methanol or ethanol at a temperture between about 0° C. and the reflux temperature. Alternatively the reaction may be performed with an alcohol, e.g. methanol or benzyl alcohol in the presence of a strong base, e.g. a hydride such as sodium hydride in an inert solvent such as an amide, e.g. dimethylformamide at a temperature between about 0° C. and 80° C.

Intermediates of formula (23) may be formed from intermediates of formula (22) in a similar manner to that described for the preparation of intermediates of formula (5) form intermediates of formula (4).

Intermediates of formula (22) may be formed from intermediates of formula (21) by reaction with a strong base, e.g. lithium tetramethylpiperidine (LiTMP) in a solvent or mixture of solvents, for example an ether such as diethyl ether of tetrahydrofuran or a mixture thereof at a low temperature, e.g. around −100° C. to form a lithium anion [according to the methods of Queguiner et al, J. Het. Chem. 1990, 27, 1377 and Mattson et al, J. Org. Chem. 1990, 55, 3410] which may be further reacted with a Weinreb amide at a temperature from about −78° C. to ambient temperature.

As an alternative a lithium anion as just described may be reacted with an aldehyde of formula ARCHO under the reaction conditions just described to give an intermediate alcohol which may be oxidised give an intermediate of formula (22) by such well known methods as manganese dioxide in a solvent, e.g. a halogenated hydrocarbon such as dichloromethane.

Compounds of the invention and intermediates thereto where A represents a —N($R^b$)— or —C($R^b$)($R^c$)— group may be generated from compounds of the invention or intermediates thereto where A represents a —N= or —C($R^b$)= group by reduction, for instance by catalytic hydrogenation using a metal catalyst such as palladium on charcoal in the presence of hydrogen gas at an elevated pressure in a solvent such as an alcohol, e.g. ethanol optionally at an elevated temperaure e.g. between 40 and 60°.

Where in the general processes described above intermediates such as alkylating agents of formula $Cy^1L^1(Alk^1)_nZ$, amides of formula ArC(O)N(OMe)Me, reagents of formula HXCH$_2$CO2Et and nitroaromatics of formula (18) and any other intermediates required in the synthesis of compounds of the invention are not available commercially or known in the literature, they may be readily obtained from simpler known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other intermediates and in particular compounds of formulae (1a) and (1b) where appropriate functional groups exist in these compounds. Particular examples of such methods are given in the Examples hereinafter.

Thus for example aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile, a thiomethyl group may be introduced by using dimethyldisulphide as the electrophile, an alcohol group may be introduced by using an aldehyde as electrophile and an acid may be introduced by using carbon dioxide as electrophile. Aromatic acids of formula ArCO$_2$H may also be generated by quenching Grignard reagents of formula ArMgHal with carbon dioxide.

Aromatic acids of formula ArCO$_2$H generated by this method and acid containing compounds in general may be converted to activated derivatives, e.g. acid halides by reaction with a halogenating agent such as a thionyl halide e.g. thionyl chloride, a phosphorous trihalide such as phosphorous trichloride or a phosphorous pentahalide such as phosphorous pentachloride optionally in an inert solvent such as an aromatic hydrocarbon e.g. toluene or a chlorinated hydrocarbon e.g. dichloromethane at a temperature from about 0° C. to the reflux temperature, or may be converted into Weinreb amides of formula ArC(O)N(OMe)Me by conversion to the acid halide as just described and subsequent reaction with an amine of formula HN(OMe)Me or a salt thereof, optionally in the presence of a base such as an organic amine, e.g. triethylamine in an inert solvent such as an aromatic hydrocarbon e.g. toluene or a chlorinated hydrocarbon e.g. dichloromethane at a temperature from about 0° C. to ambient temperature.

Compounds of the invention and intermediates thereto such as compounds of formulae (5), (6), (7), (13) and (14) may be prepared by alkylation, arylation or heteroarylation. For example, compounds containing a —L$^1$H group (where L$^1$ is a linker atom or group) may be treated with an alkylating agent $Cy^1Z^2$ in which $Z^2$ is a leaving atom or group such as a halogen atom, e.g. a fluorine, chlorine, bromine or iodine atom or a sulphonyloxy group such as an alkylsulphonyloxy, e.g. trifluoromethylsulphonyloxy or arylsulphonyloxy, e.g. p-toluenesulphonyloxy group.

The reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran.

In another example, compounds containing a —L$^2$H group as defined above may be functionalised by acylation or thioacylation, for example by reaction with the alkylating agents just described but in which $Z^2$ is replaced by a —C(O)$Z^3$, C(S)$Z^3$, —N($R^2$)COZ$^3$ or —N($R^2$)C(S)$Z^3$ group in which $Z^3$ is a leaving atom or group as described for $Z^2$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation may be carried out under the same conditions with an acid (for example one of the alkylating agents described above in which $Z^2$ is replaced by a —CO$_2$H group) in the presence of a condensing agent, for example a diimide such as 1-(3-dimethylaminopropyl)-3-ethylcarbodiimide or N,N'-dicyclohexylcarbodiimide, or a benzotriazole such as [O-(7-azabenzo-triazol-1-yl)-1,1,3,3-tetramethyluronium] hexafluorophosphate advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction In a further example compounds may be obtained by sulphonylation of a compound containing an —OH group by reaction with one of the above alkylating agents but in which $Z^2$ is replaced by a —S(O)Hal or —SO$_2$Hal group [in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a —L$^2$H group as defined above may be coupled with one of the alkylation agents just described but in which $Z^2$ is replaced by an —OH group in a solvent such as tetrahydrofuran in the presence of a phosphine, e.g. triphenylphosphine and an activator such as diethyl, diisopropyl- or dimethylazodicarboxylate.

Ester groups such as —CO$_2$Alk$^6$ and —CO$_2$R$^4$ in the compound of formula (1) and intermediates thereto may be converted to the corresponding acid [—CO$_2$H] by acid- or base-catalysed hydrolysis depending on the nature of the group Alk$^6$ or R$^4$. Acid- or base-catalysed hydrolysis may be achieved for example by treatment with an organic or inorganic acid, e.g. trifluoroacetic acid in an organic solvent e.g. dichloromethane or a mineral acid such as hydrochloric acid in a solvent such as dioxan or an alkali metal hydroxide, e.g. lithium hydroxide in an aqueous alcohol, e.g. aqueous methanol.

In a further example, —$OR^6$ [where $R^6$ represents an alkyl group such as methyl group] in compounds of formula (1) and intermediates thereto may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^{31}$ group (where $R^{31}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [e.g. —$CO_2Alk6$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —$OR^6$ group by coupling with a reagent $R^6OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in the compounds may be obtained, in another example, by reaction of a corresponding amine [—$NH_2$] with sulphamide in the presence of an organic base such as pyridine at an elevated temperature, e.g. the reflux temperature.

In another example compounds containing a —$NHCSR^7$ or —$CSNHR^7$ group may be prepared by treating a corresponding compound containing a —$NHCOR^7$ or —$CONHR^7$ group with a thiation reagent, such as Lawesson's Reagent or $P_2S_5$, in an anhydrous solvent, for example a cyclic ether such as tetrahydrofuran, at an elevated temperature such as the reflux temperature.

In a further example amine (—$NH_2$) groups may be alkylated using a reductive alkylation process employing an aldehyde and a reducing agent. Suitable reducing agents include borohydrides for example sodium triacetoxyborohyride or sodium cyanoborohydride. The reduction may be carried out in a solvent such as a halogenated hydrocarbon, e.g. dichloromethane, a ketone such as acetone, or an alcohol, e.g. ethanol, where necessary in the presence of an acid such as acetic acid at around ambient temperature. Alternatively, the amine and aldehyde may be initially reacted in a solvent such as an aromatic hydrocarbon e.g. toluene and then subjected to hydrogenation in the presence of a metal catalyst, for example palladium on a support such as carbon, in a solvent such as an alcohol, e.g. ethanol.

In a further example, amine [—$NH_2$] groups in compounds of formula (1) and intermediates thereto may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

In a further example amine (—$CH_2NH_2$) groups in compounds of formula (1) and intermediates thereto may be obtained by reduction of nitrites (—CN), for example by catalytic hydrogenation using for example hydrogen in the presence of a metal catalyst, for example palladium on a support such as carbon, or Raney® nickel, in a solvent such as an ether e.g. a cyclic ether such as tetrahydrofuran or an alcohol e.g. methanol or ethanol, optionally in the presence of ammonia solution at a temperature from ambient to the reflux temperature, or by chemical reduction using for example a metal hydride e.g. lithium aluminium hydride, in a solvent such as an ether e.g. a cyclic ether such as tetrahydrofuran, at a temperature from 0° C. to the reflux temperature.

In another example, sulphur atoms in the compounds, for example when present in a group $L^1$ or $L^2$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

In a further example N-oxides of compounds of formula (1) may in general be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid or m-chloroperoxybenzoic acid in a solvent, such as a halogenated hydrocarbon e.g. dichloromethane or an alcohol e.g. tert-butanol at a temperature from the ambient temperature to the reflux temperature.

In another example compounds of formula (12) may be converted to further compounds as formula (13) in which Ar is an optionally substituted aromatic or heteroaromatic group for use in the synthesis of for example compounds of formula (1), using such well know and commonly used palladium mediated reaction conditions as are to be found in the general reference texts *Rodd's Chemistry of Carbon Compounds*, Volumes 1–15 and Supplementals (Elsevier Science Publishers, 1989), *Fieser and Fieser's Reagents for Organic Synthesis*, Volumes 1–19 (John Wiley and Sons, 1999), *Comprehensive Heterocyclic Chemistry*, Ed. Katritzky et al, Volumes 1–8, 1984 and Volumes 1–11, 1994 (Pergamon), *Comprehensive Organic Functional Group Transformations*, Ed. Katritzky et al, Volumes 1–7, 1995 (Pergamon), *Comprehensive Organic Synthesis*, Ed. Trost and Flemming, Volumes 1–9, (Pergamon, 1991), *Encyclopedia of Reagents for Organic Synthesis*, Ed. Paquette, Volumes 1–8 (John Wiley and Sons, 1995), *Larock's Comprehensive Organic Transformations* (VCH Publishers Inc., 1989) and *March's Advanced Organic Chemistry* (John Wiley and Sons, 5$^{th}$ Ed., 2001).

Salts of compounds of formula (1a) or (1b) may be prepared by reaction of compounds of formula (1a) or (1b) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1a) or (1b) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1a) or (1b) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1a) or (1b) may be separated using chiral High Performance Liquid Chromatography. Alternatively, if desired a particular enantiomer may be obtained by using an appropriate chiral intermediate in one of the processes described above.

Alternatively, a particular enantiomer may be obtained by performing an enantiomer specific enzymatic biotransformation e.g. an ester hydrolysis using an esterase and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

The following Examples illustrate the invention. All temperatures are in ° C.

The following abbreviations are used:
NMM—N-methylmorpholine; EtOAc—ethyl acetate;
MeOH—methanol; BOC—butoxycarbonyl;
DCM—dichloromethane; AcOH—acetic acid;
DIPEA—diisopropylethylamine; EtOH—ethanol;
Pyr—pyridine; Ar—aryl;
DMSO—dimethylsulphoxide; iPr—isopropyl;
$Et_2O$—diethylether; Me—methyl;
THF—tetrahydrofuran, DMF—N,N-dimethylformamide;
MCPBA—3-chloroperoxybenzoicacid NBS—N-bromosuccinimide
FMOC—9-fluorenylmethoxycarbonyl r.t.—room temperature
DBU—1,8-Diazabicyclo[5,4-0]undec-7-ene
EDC—1-[3-(dimethylamino)propyl]-3-ethylcarbodiimide hydrochloride
HOBT—1-hydroxybenzotriazole hydrate All NMRs were obtained either at 300 MHz or 400 MHz.
Compounds were named with the aid of either Beilstein Autonom supplied by MDL Information Systems GmbH, Theodor-Heuss-Allee 108, D-60486 Frankfurt, Germany or ACD Labs Name (v.5.0) supplied by Avanced Chemical Development, Toronto, Canada.

LCMS retention times (RT) quoted were generated on a Hewlett Packard 1100 LC/MS using the following following method: Phenomenex Luna 3 $\mu C_{18}$(2) 50×4.6mm column; mobile phase A=0.1% formic acid in water; mobile phase B=0.1% formic acid in MeCN; flow rate of 0.9 $mLmin^{-1}$, column temperature 40° C.

| Gradient:- | Time | % B |
|---|---|---|
| | Initial | 5 |
| | 2.00 | 95 |
| | 3.00 | 95 |
| | 5.0 | 5 |
| | 5.5 | end |

Intermediate 1

3-Benzoyl-2-fluoropyridine

To a freshly prepared solution of lithium diisopropylamide (22 mmol) in dry THF (20 mL) under nitrogen and cooled to −78° was added a solution of 2-fluoropyridine (1.94 g, 20 mmol) in dry THF (10 mL). The reaction was stirred for 2.5 h at −78° before adding a solution of N-methoxy-N-methyl benzamide (3.47 g, 21 mmol) in THF (8 mL). The reaction mixture was allowed to warm to room temperature over 1.5 h and stir at room temperature for 1 h. The reaction was quenched with water (50 mL), extracted with EtOAc (2×50 mL), the extracts dried ($MgSO_4$) and concentrated in vacuo. The crude product was purified by chromatography on silica (5–20% EtOAc in isohexane) to give the title compound as a colourless oil (1.05 g, 26%). δH ($CDCl_3$) 8.44 (1H, ddd, J 4.9, 2.0, 1.1 Hz), 8.06 (1H, ddd, J 9.3, 7.4, 2.0 Hz), 7.84 (2H, dm, J 8.4 Hz), 7.66 (1H, tt, J 7.4, 1.3 Hz), 7.52 (2H, tm, J 7.8 Hz), 7.38 (1H, ddd, J 6.8, 4.9, 1.9 Hz). LCMS ($ES^+$) RT 3.27 minutes, 202 $(M+H)^+$ Intermediate 2

Ethyl 3-Phenylthieno[2,3-b]pyridine-2-carboxylate

To a solution of ethyl 2-mercaptoacetate (0.6 mL, 5.5 mmol) in dry DMF (10 mL) under nitrogen and cooled with an ice bath was added sodium hydride (220 mg of 60% dispersion in oil, 5.75 mmol). After hydrogen evolution had ceased the cooling bath was removed and the reaction stirred at room temperature for 30 mins. A solution of Intermediate 1 (920 mg, 4.6 mmol) in DMF (5 mL) was added and the reaction stirred at room temperature for 3 h. The reaction was quenched with water (50 mL) and extracted with EtOAc (3×50 mL). The combined EtOAc layers were washed with brine (50 mL), dried ($MgSO_4$) and concentrated in vacuo to give a mixture of the title compound and uncyclised ethyl 2-(3-benzoylpyridin-2-ylsulfanyl)acetate. This crude mixture was dissolved in EtOH (10 mL) and sodium ethoxide (10 mL of 0.5M solution in EtOH, 5.0 mmol) added. The reaction was stirred at room temperature for 45 mins after which time complete conversion of uncyclised material to title compound was observed. The reaction was diluted with EtOAc (50 mL), washed with water (20 mL), dried ($MgSO_4$) and concentrated in vacuo. The crude product was purified by chromatography on silica (10% EtOAc in isohexane) to give the title compound as a white solid (780 mg, 60%). δH ($CDCl_3$) 8.63 (1H, dd, J 4.5, 1.4 Hz), 7.78 (1H, dd, J 8.2, 1.5 Hz), 7.41 (3H, m), 7.33–7.32 (2H, m), 7.24 (1H, dd, J 8.2, 4.6 Hz), 4.18 (2H, q, J 7.1 Hz), 1.15 (3H, t, J 7.1 Hz) LCMS ($ES^+$) RT 3.90 minutes, 284 $(M+H)^+$.

Intermediate 3

Ethyl 3-phenylthieno[2,3-b]pyridine-2-carboxylate N-oxide

To a solution of Intermediate 2 in DCM (10 mL) was added MCPBA (738 mg of 60% w/w, 2.57 mmol) and the reaction stirred at r.t. for 6 h. The reaction mixture was diluted with DCM (20 mL), washed with 2M NaOH (aq), dried ($MgSO_4$) and concentrated in vacuo. The crude product was purified by chromatography on silica (80% EtOAc in isohexane—EtOAc) to give the title compound as a white solid (670 mg, 90%). δH ($CDCl_3$) 8.36 (1H, d, J 6.1 Hz), 7.55–7.49 (4H, m), 7.44–7.39 (2H, m), 7.26 (1H, dd, J 8.2, 6.2 Hz), 4.20 (2H, q, J 7.1 Hz), 1.16 (3H, t, J 7.1 Hz). LCMS ($ES^+$) RT3.18 minutes, 300 $(M+H)^+$ Intermediate 4

Ethyl 6-oxo-3-phenyl-6,7-dihydrothieno[2,3-b]pyridine-2-carboxylate

A mixture of Intermediate 3 (400 mg, 1.34 mmol) and acetic anhydride (20 mL) was heated to reflux for 18 h. The reaction mixture was concentrated in vacuo and the residue co-evapourated with toluene (4×20 mL). The crude material was dissolved in THF (20 mL) and treated with 10% aqueous $K_2CO_3$ (20 mL). The reaction was stirred at room temperature for 18 h and then extracted with EtOAc (3×25 mL). The EtOAc extracts were dried ($MgSO_4$) and concentrated in vacuo. The crude product was purified by chromatography on silica (40–50% EtOAc in isohexane) to give the title compound as a white solid (193 mg, 48%). δH ($CDCl_3$) 7.48 (1H, d, J 9.5 Hz), 7.43–7.36 (3H, m), 7.31–7.28 (2H, m), 6.53 (1H, d, J 9.5 Hz), 4.13 (2H, q, J 7.1 Hz), 1.12 (3H, t, J 7.1 Hz). LCMS ($ES^+$) RT 3.25 minutes, 322 (($M+Na)^+$, 24%), 300 (($M+H)^+$, 100%).

Intermediate 5

Ethyl 3-aminothieno[2,3-b]pyridine-2-carboxylate

A mixture of 2-chloro-3-cyanopyridine (330 g), ethyl 2-mercaptoacetate (361.2 g), sodium carbonate (265 g) and EtOH (1.2 L) was heated to reflux for 4.5 hours. It was then cooled to ambient temperature, added to water (10 L) and the addition was washed in with water (5 L). The resulting slurry was stirred for 30 minutes and then it was filtered. The filter cake was washed with two portions of water (2×2.5 L) and dried at the pump. The solids were then dried to constant weight under vacuum at 45° to yield the title compound as a brown solid (493.1 g, 93.2%). δH ($CDCl_3$) 8.68 (1H, dd, J 4.7, 1.2 Hz), 7.93 (1H, dd, J 8.5, 1.2 Hz), 7.29 (1H, dd, J 8.5, 4.7 Hz), 5.90 (2H, b), 4.38 (2H, q, J 7.0 Hz), 1.40 (3H, t, J 7.0 Hz). LCMS RT 2.9 minutes, 223 $(M+H)^+$ Intermediate 6

Ethyl 3-bromothieno[2,3-b]pyridine-2-carboxylate

Intermediate 5 (363.6 g) was added in portions over two hours to a mixture of copper(II) bromide (403.3 g), t-butyl nitrite (220.6 g) and acetonitrile (3.6 L) stirred at a temperature of 20 to 25°. The mixture was stirred at 20° for 2 hours before it was slowly added to 2M HCl(aq) (4.2 L). The reaction mixture slurry was filtered and the solids were washed with water (500 mL). The combined filtrate was extracted with EtOAc (8 L), and the EtOAc solution was washed with 2M HCl(aq) (2.2 L). The solids were dissolved in EtOAc (6 L) and this solution was washed twice with 2M HCl(aq) (4.4 L and 2.2 L). The two EtOAc solutions were then combined and washed with 2M HCl(aq) (2.2 L) and twice with water (2×2 L). The EtOAc solution was then dried ($MgSO_4$), filtered and concentrated in vacuo at 40 mbar and 60° to give a solid residue. This was broken up and dried to constant weight under vacuum at 45° to yield the title compound as a brown solid (458.5 g, 97.9%). δH (DMSO-d6) 8.89 (1H, d, J 4.7 Hz), 8.47 (1H, d, J 8.6 Hz), 7.71 (1H, dd, J 8.6, 4.7 Hz), 4.46 (2H, q, J 7.2 Hz), 1.40 (3H, t, J 7.2 Hz). LCMS RT 3.8 minutes, 288 $(M+H)^+$ Intermediate 7

Ethyl 3-Bromothieno[2,3-b]pyridine-2-carboxylate N-oxide

To a slurry of Intermediate 6 (214 g, 0.747 Mol) in DCM (2140 mL) under nitrogen was added MCPBA (240 g @ 70%=168 g, 0.97 Mol) portion wise over 0.5 h. The reaction was then stirred at r.t. for 18 h. The reaction mixture was quenched with water (800 mL) and pH adjusted to 8.5 with 10% w/v sodium carbonate solution (1250 mL). The basic aqueous layer was removed and the organic layer washed with water until pH 7. The organic layer was concentrated in vacuo and the crude title product was recovered as a tan solid. The crude product was purified by slurrying in methyl tert-butyl ether (600 mL) for 1 hr at 0–5° to give the title compound (174 g, 77%). δH ($CDCl_3$) 8.44 (1H, dd, J 6.2, 0.8 Hz), 7.87 (1H, dd, J 8.3, 0.8 Hz), 7.48 (1H, dd, J 8.3, 6.2 Hz), 4.49 (2H, q, J 7.1 Hz), 1.48 (3H, t, J 7.1 Hz). LCMS ($ES^+$) RT 2.61 minutes, 302$(M)^+$ Intermediate 8

Ethyl 3-bromo-6-oxo-6,7-dihydrothieno[2,3-b]pyridine-2-carboxylate

A mixture of Intermediate 7 (500 mg, 1.66 mmol) and DMF (10 mL) was set to stir at 0° under nitrogen. To this reaction mixture was added trifluoroacetic anhydride (3.49 g, 2.36 mL, 16.6 mmol) in one portion via syringe. After stirring for 16 hours the volatiles were removed in vacuo and the residue co-evaporated with toluene (2×20 mL). The crude material was then extracted with EtOAc (2×100 mL). The EtOAc extracts were dried ($MgSO_4$) and concentrated in vacuo. The crude product was purified by a re-slurry in toluene (10 mL) to give the title compound as a beige solid (260 mg, 52%). δH (DMSO-d6) 12.20 (1H, brs), 7.75 (1H, d, J 9.0 Hz), 6.50 (1H, d, J 9.0 Hz), 4.15 (2H, q, J 7.1 Hz), 1.12 (3H, t, J 7.1 Hz). LCMS ($ES^+$) RT 2.86 minutes, 302 (($M+H)^+$, 100%). MP=261.7–268.1° C.

Intermediate 9

Ethyl 3-bromo-6-oxo-7-phenyl-6,7-dihydrothieno[2,3-b]pyridine-2-carboxylate

To a 2 necked round bottomed flask was added in sequence Intermediate 8 (302 mg, 1.00 mmol), copper(II) acetate (278 mg, 1.50 mmol, 150 mol %), phenylboronic acid (488 mg, 4.00 mmol), DCM (5 mL) and pyridine (158 mg, 2.00 mmol). The reaction was stirred at room temperature for 18 h with the exclusion of moisture. The reaction was then diluted with DCM (50 mL), washed with 2M HCl(aq) (50 mL), the aqueous was re-extracted with DCM (50 mL). The combined organics were then washed with water (50 mL), dried ($MgSO_4$) and concentrated in vacuo. The crude product was purified by a slurry in methanol (12 mL), to give the title compound as a beige solid (270 mg, 72%). δH ($CDCl_3$) 7.82 (1H, d, J 8.5 Hz), 7.70–7.62 (3H, m), 7.54–7.42 (2H, m), 6.70 (1H, d, J 8.5 Hz), 4.15 (2H, q, J 7.1 Hz), 1.14 (3H, t, J 7.1 Hz). LCMS ($ES^+$) RT 3.75 minutes, 378 $(M+H)^+$. MP=201.6–206.0° C.

Intermediate 10

Ethyl 3-(4-fluorophenyl)-6-oxo-6,7-dihydrothieno[2,3-b]pyridine-2-carboxylate

A mixture of Intermediate 8 (241 mg, 0.8 mmol), tetrakis (triphenylphosphine)palladium(0) (92 mg, 0.08 mmol, 10 mol %), 2M $K_2CO_3$ (aq) (0.8 mL, 1.6 mmol) and 4-fluorophenylboronic acid in ethylene glycol dimethyl ether (10 mL) was heated to reflux under nitrogen for 20 h. Solvent was removed in vacuo and the crude product purified by chromatography on silica (10% THF in DCM) to give the title compound as a white solid (210 mg). LCMS ($ES^+$) RT 3.24 minutes, 318 $(M+H)^+$.

Intermediate 11

6-Oxo-3-phenyl-6,7-dihydrothieno[2,3-b]pyridine-2-carboxamide

To a solution of Intermediate 4 (5.13 g, 17 mmol) in 1:1 THF water (200 mL) was added lithium hydroxide monohydrate (1.6 g, 37.4 mmol) and the reaction stirred at r.t. overnight. The reaction was incomplete at this time and was therefore concentrated on a rotary evaporator by approx. half and the reaction heated at 60° for 20 h. Reaction showed complete conversion to the carboxylic acid at this time. The reaction was diluted with water (50 mL) and 2M HCl(aq) added with stirring until a precipitate had formed (pH 1–2). The solid was filtered, washed with several portions of water and dried in a vacuum oven to afford 6-oxo-3-phenyl-6,7-dihydrothieno[2,3-b]pyridine-2-carboxylic acid as a solid (3.0 g). LC RT 2.72 minutes. This compound was suspended in anhydrous DMF (30 mL), 1,1'-carbonyldiimidazole (2.14 g, 13.2 mmol) added and the reaction stirred for 30 mins. Ammonia (75 mL of 25% aqueous solution) was added and the reaction stirred at r.t. for 1 h before being concentrated in vacuo. The resultant solid was suspended in 2M HCl(aq), collected by filtration and dried in a vacuum oven to give the title compound as a white solid (2.63 g). δH (DMSO-d6) 7.63–7.49 (4H, m), 7.45–7.42 (2H, m), 6.51 (1H, d, J 9.2 Hz), 6.28 (1H, bs). LCMS (ES$^+$) 271 (M+H)$^+$.

Intermediate 12

6-oxo-3-phenyl-6,7-dihydrothieno[2,3-b]pyridine-2-carbonitrile

To a solution of Intermediate 11 (270 mg, 1.0 mmol) and pyridine (141 μL, 1.0 mmol) in dry DCM (10 mL) was added trifluoroacetic anhydride (160 μL, 2.0 mmol) and the reaction stirred at r.t. for 16 h. Solvent was removed in vacuo and the resultant solid suspended in water (30 mL) and acidified with 2M HCl(aq) (10 mL). The solid was collected by filtration, washed with water (25 mL) and dried in vacuo to afford the title compound as a white solid (220 mg, 87%). δH (DMSO-d6) 7.85 (1H, d, J 9.1 Hz), 7.63–7.58 (5H, m), 6.69 (1H, d, J 9.1 Hz). LCMS (ES$^+$) 253 (M+H)$^+$.

Intermediate 13

6-Oxo-3,7-diphenyl-6,7-dihydrothieno[2,3-b]pyridine-2-sulfonyl chloride

To a solution of the compound of Example 84 (675 mg, 2.5 mmol) in dry DCM (20 mL) cooled to −78° was added chlorosulfonic acid (1.72 g, 14.7 mmol) over 5 mins. After 15 minutes reaction was removed from the cooling bath and stirred at r.t. for 1 h. Reaction was poured onto ice-water and extracted with DCM. The combined DCM extracts were dried (MgSO$_4$) and concentrated in vacuo to give the title compound as a yellow solid (65 mg).

Intermediate 14

Ethyl 3-(2,4-difluorophenyl)-6-oxo-6,7-dihydrothieno[2,3-b]pyridine-2-carboxylate The title compound was prepared from Intermediate 8 and 2,4-difluorophenylboronic acid following the analogous procedure described for Intermediate 10. This gave the title compound as a white solid LCMS (ES$^+$) 336 (M+H)$^+$.

Intermediate 15

1-Phenyl-1H-pyrrolo[3,2-b]pyridine

1H-Pyrrolo[3,2-b]pyridine (0.5 g, 4.24 mmol), phenylboronic acid (1.03 g, 8.44 mmol), copper(II) acetate (1.54 g, 8.48 mmol), and 4A molecular sieves (2 g), were suspended in DCM (10 mL). Triethylamine (1.19 mL, 8.5 mmol) and pyridine (0.7 mL, 8.65 mmol) were added and the reaction stirred at r.t. for three days. The reaction mixture was diluted with further DCM, filtered and concentrated in vacuo. Chromatography (silica, EtOAc) gave the title compound (325 mg). δH (CDCl$_3$) 7.80 (1H, d, J 8.2 Hz), 7.54–7.30 (7H, m), 7.15 (1H, brs), 6.88 (1H, brs). LCMS (ES$^+$) RT 1.20 minutes, 195 (M+H)$^+$.

Intermediate 16

1-Phenyl-1H-pyrrolo[3,2-b]pyridine 4-oxide

Intermediate 15 (307 mg, 1.58 mmol) was dissolved in DCM (5 mL) and treated with MCPBA (356 mg, 2.06 mmol). After stirring for eighteen hours at r.t. the reaction was diluted with DCM, washed twice with 2M sodium hydroxide, dried (sodium sulphate) and concentrated in vacuo to give the title compound (285 mg). δH (CDCl$_3$) 8.15 (1H, d, J 6.2 Hz), 7.55–7.47 (2H, m), 7.42–7.37 (5H, m), 7.07, (1H, dd, J 0.7, 3.5 Hz), 7.01 (1H, dd, J 6.2, 8.4 Hz). LCMS (ES$^+$) RT 2.527 minutes, 211 (M+H)$^+$.

Intermediate 17

1-Phenyl-1,4-dihydro-pyrrolo[3,2-b]pyridin-5-one

Intermediate 16 (273 mg, 1.3 mmol) was dissolved in DMF (3 mL) and treated at 0° with trifluoroacetic anhydride (1.8 mL, 13 mmol), was allowed to warm to r.t. and stir for two hours. The reaction was diluted with toluene and concentrated in vacuo, re-dissolved in EtOH and concentrated again to give the title compound as an olive coloured solid (420 mg). δH (CDCl$_3$) 8.10 (1H, d, J 9.2 Hz), 7.72–7.51 (6H, m), 6.85–6.82 (2H, m). LCMS (ES$^+$) RT 2.668 minutes 211 (M+H)$^+$.

EXAMPLE 1

Ethyl 6-oxo-3,7-diphenyl-6,7-dihydrothieno[2,3-b]pyridine-2-carboxylate

To an oven dried flask was added in sequence 4 Å molecular sieves (33 mg), phenylboronic acid (82 mg, 0.67 mmol), DCM (3 mL), pyridine (53 mg, 0.67 mmol), Intermediate 4 (100 mg, 0.33 mmol), copper(II) acetate (6 mg, 0.033 mmol, 10 mol %) and pyridine N-oxide (34 mg, 0.36 mmol). The reaction was stirred at room temperature for 18 h with the exclusion of moisture. The reaction was then diluted with DCM (20 mL), washed with 2M HCl(aq) (2×10 mL), 2M NaOH(aq) (3×10 mL), dried (MgSO$_4$) and concentrated in vacuo. The crude product was purified by chromatography on silica (DCM—1% MeOH in DCM) to give the title compound as a buff solid (95 mg, 77%). δH (CDCl$_3$) 7.68–7.56 (3H, m), 7.54–7.42 (6H, m), 7.40–7.38 (2H, m), 6.70 (1H, d, J 9.6 Hz), 4.15 (2H, q, J 7.1 Hz), 1.14 (3H, t, J 7.1 Hz). LCMS (ES$^+$) RT 3.87 minutes, 376 (M+H)$^+$.

EXAMPLE 2

Ethyl 7-cyclopropylmethyl-6-oxo-3-phenyl-6,7-dihydrothieno[2,3-b]pyridine-2-carboxylate To a solution of Intermediate 4 (90 mg, 0.3 mmol) in dry DMF (3 mL) was added polystyrene supported 2-tert-butyl-imino-2-diethylamino-1,3-dimethyl-perhydro-1,3,2-diaza-phosphorine (PS-BEMP, 177 mg) and cyclopropylmethyl bromide (101 mg, 73 μL, 0.75 mmol). The reaction was then heated to 80° under nitrogen for 18 h. The crude reaction mixture was filtered to remove PS-BEMP and the resin washed with EtOAc. The filtrate was concentrated in vacuo and the residue purified by chromatography (DCM—1% MeOH in DCM) to give the title compound as a brown gum (57 mg, 54%). Recrystallisation from diisopropyl ether gave the title compound as brown needles (30 mg). δH (CDCl$_3$) 7.44–7.35 (3H, m), 7.31–7.24 (4H, m), 6.45 (1H, d, J 9.5 Hz), 4.14 (2H, q, J 7.1 Hz), 4.04 (2H, d, J 7.1 Hz), 1.42 (1H, m), 1.12 (3H, t, J 7.1 Hz), 0.53 (4H, m). LCMS (ES$^+$) RT 4.04 minutes, 354 (M+H)$^+$.

EXAMPLE 3

Ethyl 7-(4-dimethylaminophenyl)-6-oxo-3-phenyl-6,7-dihydrothieno[2,3-b]pyridine-2-carboxylate To an oven dried flask was added in sequence 4-dimethylaminophenylboronic acid (551 mg, 3.34 mmol), DCM (10 mL), pyridine (0.27 mL, 3.34 mmol), Intermediate 4 (500 mg, 1.67 mmol), copper(II) acetate (34 mg, 0.17 mmol, 10 mol %) and pyridine N-oxide (318 mg, 3.34 mmol). The reaction was stirred at r.t. for 24 h with the exclusion of moisture. The reaction was then diluted with DCM (20 mL), washed with saturated NH$_4$Cl(aq), NaHCO$_3$ (aq), dried (MgSO$_4$) and concentrated in vacuo. The crude product was purified by chromatography on silica (5–10% EtOAc in DCM) to give the title compound as a white solid (150 mg, 21%). δH (DMSO-d6) 7.51–7.49 (3H, m), 7.42–7.40 (3H, m), 7.30 (2H, d, J 9.0 Hz), 6.89 (2H, d, J 9.0 Hz), 6.53 (1H, d, J 9.6 Hz), 4.07 (2H, q, J 7.1 Hz), 3.31 (6H, s), 1.06 (3H, t, J 7.1 Hz). LCMS (ES$^+$) RT 4.10 minutes, 419 (M+H)$^+$.

General Procedure for the Preparation of Ethyl 7-aryl-6-oxo-3-phenyl-6,7-tetrahydrothieno[2,3-b]pyridine-2-carboxylates The compounds of the following Examples 4–16 were prepared by parallel synthesis using a Radleys Carousel reaction station (Radleys Ltd., Saffron Walden, U.K.) following a procedure similar to that described for Example 3. Therefore to each oven dried reaction tube in the Carousel was added a magnetic stirrer, the appropriate arylboronic acid (1.0 mmol), DCM (5 mL), pyridine (0.08 mL, 1.0 mmol), Intermediate 4 (150 mg, 0.5 mmol), copper(II) acetate (10 mg, 0.05 mmol, 10 mol %) and pyridine N-oxide (95 mg, 1.0 mmol). The reactions were stirred at r.t. for 18 h with the exclusion of moisture. Each reaction was then diluted with DCM (20 mL), washed with saturated NH$_4$Cl (aq), NaHCO$_3$(aq), dried (MgSO$_4$) and concentrated in vacuo. The crude products were purified on silica eluting with 0–25% EtOAc in DCM to give the title compounds as solids.

EXAMPLE 4

Ethyl 7-(4-methoxyphenyl)-6-oxo-3-phenyl-6,7-dihydrothieno[2,3-b]pyridine-2-carboxylate δH (DMSO-d6) 7.51–7.39 (8H, m), 7.19 (2H, d, J 9.0 Hz), 6.55 (1H, d, J 9.6 Hz), 4.08 (2H, q, J 7.1 Hz), 3.88 (3H, s), 1.05 (3H, t, J 7.1 Hz). LCMS (ES$^+$) RT 3.85 minutes, 406 (M+H)$^+$.

EXAMPLE 5

Ethyl 7-(3-methoxyphenyl)-6-oxo-3-phenyl-6,7-dihydrothieno[2,3-b]pyridine-2-carboxylate δH (DMSO-d6) 7.59 (1H, t, J 8.3 Hz), 7.51 (3H, m), 7.49 (1H, m), 7.46 (2H, m), 7.18 (2H, m), 7.11 (1H, m), 6.57 (1H, d, J 9.7 Hz), 4.06 (2H, q, J 7 Hz), 3.82 (3H, s), 1.07 (3H, t, J 7 Hz). LCMS (ES$^+$) RT 3.87 minutes, 406 (M+H)$^+$.

EXAMPLE 6

Ethyl 6-oxo-3-phenyl-7-(4-tolyl)-6,7-dihydrothieno[2,3-b]pyridine-2-carboxylate

δH (DMSO-d6) 7.53–7.40 (10 H, m), 6.55 (1H, d, J 9.7 Hz), 4.07 (2H, q, J 7.1 Hz), 2.45 (3H, s), 1.06 (3H, t, J 7.1 Hz). LCMS (ES$^+$) RT 4.11 minutes, 390 (M+H)$^+$.

EXAMPLE 7

Ethyl 7-(5-indolyl)-6-oxo-3-phenyl-6,7-dihydrothieno[2,3-b]pyridine-2-carboxylate δH (DMSO-d6) 11.48 (1H, bs), 7.71 (1H, s), 7.64 (1H, d, J 8.6 Hz), 7.55–7.16 (7H, m), 7.13 (1H, d, J 2.1 Hz), 6.58 (1H, m), 6.57 (1H, d, J 9.6 Hz), 4.05 (2H, q, J 7.1 Hz), 1.03 (3H, t, J 7.1 Hz). LCMS (ES$^+$) RT 3.73 minutes, 415 (M+H)$^+$.

EXAMPLE 8

Ethyl 6-oxo-3-phenyl-7-(3-thienyl)-6,7-dihydrothieno[2,3-b]pyridine-2-carboxylate δH (DMSO-d6) 8.04 (1H, dd, J 3.1, 1.4 Hz), 7.85 (1H, dd, J 5.1, 3.1 Hz), 7.41 (3H, m), 7.39 (3H, m), 7.28 (1H, d, J 1.4 Hz), 6.55 (1H, d, J 9.7 Hz), 4.09 (2H, q, J 7.1 Hz), 1.06 (3H, t, J 7.1 Hz). LCMS (ES$^+$) RT 3.83 minutes, 382 (M+H)$^+$.

EXAMPLE 9

Ethyl 6-oxo-3-phenyl-7-(4-trifluoromethoxyphenyl)-6,7-dihydrothieno[2,3-b]pyridine-2-carboxylate LCMS (ES$^+$) RT 4.20 minutes 460 (M+H)$^+$.

EXAMPLE 10

Ethyl 7-(3-fluorophenyl)-6-oxo-3-phenyl-6,7-dihydrothieno[2,3-b]pyridine-2-carboxylate LCMS (ES$^+$) RT 3.91 minutes 394 (M+H)$^+$.

EXAMPLE 11

Ethyl 7-(4-fluorophenyl)-6-oxo-3-phenyl-6,7-dihydrothieno[2,3-b]pyridine-2-carboxylate LCMS (ES+) RT 3.88 minutes 394 (M+H)+.

EXAMPLE 12

Ethyl 7-(4-chlorophenyl)-6-oxo-3-phenyl-6,7-dihydrothieno[2,3-b]pyridine-2-carboxylate LCMS (ES+) RT 4.14 minutes 410 (M+H)+.

EXAMPLE 13

Ethyl 7-(3-cyanophenyl)-6-oxo-3-phenyl-6,7-dihydrothieno[2,3-b]pyridine-2-carboxylate LCMS (ES+) RT 3.72 minutes 401 (M+H)+.

EXAMPLE 14

Ethyl 6-oxo-3-phenyl-7-(3-tolyl)-6,7-dihydrothieno[2,3-b]pyridine-2-carboxylate

LCMS (ES+) RT 4.09 minutes, 390 (M+H)+.

EXAMPLE 15

Ethyl 6-oxo-3-phenyl-7-(4-trifluoromethylphenyl)-6,7-dihydrothieno[2,3-b]pyridine-2-carboxylate LCMS (ES+) RT 4.22 minutes, 444 (M+H)+.

EXAMPLE 16

Ethyl 7-(3-bromophenyl)-6-oxo-3-phenyl-6,7-dihydrothieno[2,3-b]pyridine-2-carboxylate LCMS (ES+) RT 4.24 minutes, 454 (M+H)+.

EXAMPLE 17

Ethyl 3-(4-fluorophenyl)-6-oxo-7-phenyl-6,7-dihydrothieno[2,3-b]pyridine-2-carboxylate To an oven dried flask was added in sequence phenylboronic acid (78 mg, 0.64 mmol), DCM (5 mL), pyridine (0.64 mmol), Intermediate 10 (100 mg, 0.32 mmol), copper(II) acetate (0.032 mmol, 10 mol %) and pyridine N-oxide (0.35 mmol). The reaction was stirred at r.t. for 48 h with the exclusion of moisture. The reaction was then diluted with DCM (20 mL), washed with saturated NH$_4$Cl(aq), dried (MgSO$_4$) and concentrated in vacuo. The crude product was purified by chromatography on silica (0–5% THF in DCM) to give the title compound as a white solid (75 mg). δH (CDCl$_3$) 7.70–7.56 (3H, m), 7.50–7.42 (3H, m), 7.40–7.32 (2H, m), 7.25–7.15 (2H, m), 6.64 (1H, d, J 9.6 Hz), 4.16 (2H, q, J 7 Hz), 1.17 (3H, t, J 7 Hz). LCMS (ES+) RT 3.77 minutes, 394 (M+H)+. C$_{22}$H$_{16}$NFO$_3$S requires C, 67.16%; H, 4.10%; N, 3.56%; found C, 67.16%; H, 4.10%; N, 3.54%.

EXAMPLE 18

Ethyl 7-(3-chlorophenyl)-3-(4-fluorophenyl)-6-oxo-6,7-dihydrothieno[2,3-b]pyridine-2-carboxylate To an oven dried flask was added in sequence 3-chlorophenylboronic acid (108 mg, 0.688 mmol), dichloroethane (5 mL), pyridine (0.056 mL, 0.688 mmol), Intermediate 10 (109 mg, 0.344 mmol), copper(II) acetate (8 mg, 0.034 mmol, 10 mol %) and pyridine N-oxide (36 mg, 0.38 mmol). The reaction was heated at 70° for 48 h with the exclusion of moisture. The reaction was then diluted with DCM (20 mL), washed with saturated NH$_4$Cl(aq), dried (MgSO$_4$) and concentrated in vacuo. The crude product was purified by chromatography on silica (0–5% THF in DCM) to give the title compound as a white solid (75 mg). LCMS (ES+) RT 3.93 minutes, 428 (M+H)+.

EXAMPLE 19

Ethyl 6-oxo-7-phenyl-3-(2-tolyl)-6,7-dihydrothieno[2,3-b]pyridine-2-carboxylate

2M K$_2$CO$_3$(aq) (0.25 mL, 0.5 mmol) was added to a solution of Intermediate 9 (100 mg, 0.266 mmol), Tetrakis(triphenylphosphine)palladium(0) (30 mg, 0.027 mmol, 10 mol %) and 2-tolylboronic acid (44 mg, 0.32 mmol) in ethylene glycol dimethyl ether (4 mL) and the reaction heated to reflux for 24 h under nitrogen. The mixture was diluted with water (10 mL), extracted with DCM (2×8 mL), the combined DCM extracts dried (MgSO$_4$) and concentrated in vacuo. The crude product was purified by chromatography on silica (0–20% EtOAc in DCM) to give the title compound as a white solid (57 mg). δH (CDCl$_3$) 7.60–7.48 (3H, m), 7.40 (2H, m), 7.27–7.10 (4H, m), 7.07 (1H, m), 6.51 (1H, d, J 9 Hz), 4.03 (2H, q, J 7 Hz), 2.06 (3H, s), 0.99 (3H, t, J 7 Hz). LCMS (ES+) RT 3.87 minutes, 390 (M+H)+. C$_{23}$H$_{19}$NO$_3$S requires C, 70.93%; H, 4.92%; N, 3.60%; found C, 70.66%; H, 4.95%; N, 3.52%.

General Procedure for the Preparation of Ethyl 3-aryl-6-oxo-7-phenyl-6,7-tetrahydrothieno[2,3-b]pyridine-2-carboxylates The compounds of the following Examples 20–43 were prepared by parallel synthesis using a Radleys Carousel reaction station (Radleys Ltd., Saffron Walden, U.K.) following a procedure similar to that described for the compound of Example 19. Each reaction tube in the Carousel was charged with the appropriate arylboronic acid (0.32 mmol, 1.2 equiv.), Intermediate 9 (100 mg, 0.266 mmol), tetrakis(triphenylphosphine)palladium(0) (30 mg, 10 mol %) and a magnetic stirrer bar. Ethylene glycol dimethyl ether (4 mL) was added to each tube followed by 2M K$_2$CO$_3$(aq) (0.25 mL, 5 mmol) and the reactions heated to reflux under nitrogen for 24 h. Each reaction was then diluted with water (10 mL), extracted with DCM (2×8 mL) and the combined DCM extracts dried (MgSO$_4$) and concentrated in vacuo. The crude products were purified on silica eluting with 0–25% EtOAc in DCM to give the title compounds as solids.

EXAMPLE 20

Ethyl 6-oxo-7-phenyl-3-(3-tolyl)-6,7-dihydrothieno[2,3-b]pyridine-2-carboxylate

δH (DMSO-d6) 7.70–7.60 (3H, m), 7.56 (2H, m), 7.45 (1H, d, J 10 Hz), 7.37 (1H, d, J 7 Hz), 7.36 (1H, m), 7.27

(2H, m), 6.55 (1H, d, J 10 Hz), 4.03 (2H, q, J 7 Hz), 2.38 (3H, s), 1.05 (3H, t, J 7 Hz). LCMS (ES$^+$) RT 3.93 minutes, 390 (M+H)$^+$. $C_{23}H_{19}NO_3S$ requires C, 70.93%; H, 4.92%; N, 3.60%; found C, 70.74%; H, 4.95%; N, 3.60%.

EXAMPLE 21

Ethyl 6-oxo-7-phenyl-3-(4-tolyl)-6,7-dihydrothieno[2,3-b]pyridine-2-carboxylate

δH (CDCl$_3$) 7.70–7.50 (3H, m), 7.48–7.30 (3H, m), 7.25–7.15 (4H, m), 6.52 (1H, d, J 10 Hz), 4.07 (2H, q, J 7 Hz), 2.36 (3H, s), 1.08 (3H, t, J 7 Hz). LCMS (ES$^+$) RT 3.94 minutes, 390 (M+H)$^+$. $C_{23}H_{19}NO_3S$ requires C, 70.93%; H, 4.92%; N, 3.60%; found C, 70.42%; H, 4.92%; N, 3.58%.

EXAMPLE 22

Ethyl 3-(2-methoxyphenyl)-6-oxo-7-phenyl-6,7-dihydrothieno[2,3-b]pyridine-2-carboxylate δH (CDCl$_3$) 7.60–7.50 (3H, m), 7.48–7.30 (3H, m), 7.27 (1H, d, J 10 Hz), 7.16 (1H, m), 7.01–6.94 (2H, m), 6.51 (1H, d, J 10 Hz), 4.05 (2H, q, J 7 Hz), 3.71 (3H, s), 1.03 (3H, t, J 7 Hz). LCMS (ES$^+$) RT 3.67 minutes, 406 (M+H)$^+$. $C_{23}H_{19}NO_4S$ requires C, 68.13%; H, 4.72%; N, 3.45%; found C, 67.87%; H, 4.71%; N, 3.37%.

EXAMPLE 23

Ethyl 3-(2-fluorophenyl)-6-oxo-7-phenyl-6,7-dihydrothieno[2,3-b]pyridine-2-carboxylate δH (CDCl$_3$) 7.80–7.50 (3H, m), 7.49–7.25 (3H, m), 7.48–7.10 (4H, m), 6.55 (1H, d, J 10 Hz), 4.07 (2H, q, J 7 Hz), 1.06 (3H, t, J 7 Hz). LCMS (ES$^+$) RT 3.71 minutes, 394 (M+H)$^+$. $C_{22}H_{16}NFO_3S$ requires C, 67.16%; H, 4.10%; N, 3.56%; found C, 66.99%; H, 4.05%; N, 3.49%.

EXAMPLE 24

Ethyl 3-(3-chlorophenyl)-6-oxo-7-phenyl-6,7-dihydrothieno[2,3-b]pyridine-2-carboxylate δH (CDCl$_3$) 7.68–7.58 (3H, m), 7.48–7.32 (5H, m), 7.28 (2H, m), 6.66 (1H, d, 10 Hz), 4.17 (2H, q, J 7 Hz), 1.16 (3H, t, J 7 Hz). LCMS (ES$^+$) RT 3.96 minutes, 410 (M+H)$^+$. $C_{22}H_{16}NClO_3S$ requires C, 64.47%; H, 3.93%; N, 3.42%; found C, 64.47%; H, 3.94%; N, 3.35%.

EXAMPLE 25

Ethyl 3-(2-chlorophenyl)-6-oxo-7-phenyl-6,7-dihydrothieno[2,3-b]pyridine-2-carboxylate δH (CDCl$_3$) 7.60–7.05 (10 H, m), 6.53 (1H, d, J 10 Hz), 4.04 (2H, q, J 7 Hz), 1.01 (3H, t, J 7 Hz). LCMS (ES$^+$) RT 3.87 minutes, 410 (M+H)$^+$. $C_{22}H_{16}NClO_3S$ requires C, 64.47%; H, 3.93%; N, 3.42%; found C, 64.19%; H, 3.97%; N, 3.41%.

EXAMPLE 26

Ethyl 3-(5-chloro-2-methoxyphenyl)-6-oxo-7-phenyl-6,7-dihydrothieno[2,3-b]pyridine-2-carboxylate δH (CDCl$_3$) 7.60–7.45 (3H, m), 7.43–7.34 (2H, m), 7.32 (1H, dd, J 9, 3 Hz), 7.26 (1H, d, J 10 Hz), 7.14 (1H, d, J 3 Hz), 6.88 (1H, d, J 8 Hz), 6.53 (1H, d, J 10 Hz), 4.08 (2H, m), 3.69 (3H, s), 1.06 (3H, t J 7 Hz). LCMS (ES$^+$) RT 4.27 minutes, 440 (M+H)$^+$.

EXAMPLE 27

Ethyl 3-(4-fluoro-2-methylphenyl)-6-oxo-7-phenyl-6,7-dihydrothieno[2,3-b]pyridine-2-carboxylate δH (CDCl$_3$) 7.60–7.48 (3H, m), 7.45–7.37 (2H, m), 7.18 (1H, m), 7.04 (1H, dd, J 8, 6 Hz), 6.98–6.89 (2H, m), 6.52 (1H, d, J 9 Hz), 4.04 (2H, q, J 7 Hz), 2.06 (3H, s), 1.03 (3H, t, J 7 Hz). LCMS (ES$^+$) RT 4.28 minutes, 408 (M+H)$^+$.

EXAMPLE 28

Ethyl 3-(2,3-dichlorophenyl)-6-oxo-7-phenyl-6,7-dihydrothieno[2,3-b]pyridine-2-carboxylate δH (CDCl$_3$) 7.60–7.53 (2H, m), 7.51–7.46 (2H, m), 7.45–7.30 (2H, m), 7.25 (1H, t, J 7.5 Hz), 7.19 (1H, d, J 10 Hz), 7.13 (1H, dd, J 7.5, 1.5 Hz), 6.54 (1H, d, J 10 Hz), 4.04 (2H, m), 1.02 (3H, t, J 7 Hz). LCMS (ES$^+$) RT 4.49 minutes, 444 (M+H)$^+$.

EXAMPLE 29

Ethyl 3-(2,4-difluorophenyl)-6-oxo-7-phenyl-6,7-dihydrothieno[2,3-b]pyridine-2-carboxylate δH (CDCl$_3$) 7.60–7.47 (3H, m), 7.42–7.33 (2H, m), 7.31 (1H, dd, J 10, 1 Hz), 7.23 (1H, q with F coupling, J 8 Hz), 6.98–6.85 (2H, m), 6.56 (1H, d, J 10 Hz), 4.12 (2H, m), 1.08 (3H, t J 7 Hz). LCMS (ES$^+$) RT 4.09 minutes, 412 (M+H)$^+$.

EXAMPLE 30

Ethyl 3-(3-methoxyphenyl)-6-oxo-7-phenyl-6,7-dihydrothieno[2,3-b]pyridine-2-carboxylate LCMS (ES$^+$) RT 3.74 minutes, 406 (M+H)$^+$.

EXAMPLE 31

Ethyl 3-(4-methoxyphenyl)-6-oxo-7-phenyl-6,7-dihydrothieno[2,3-b]pyridine-2-carboxylate LCMS (ES$^+$) RT 3.72 minutes, 406 (M+H)$^+$. $C_{23}H_{19}NO_4S$ requires C, 68.13%; H, 4.72%; N, 3.45%; found C, 67.96%; H, 4.70%; N, 3.40%.

EXAMPLE 32

Ethyl 3-(3-cyanophenyl)-6-oxo-7-phenyl-6,7-dihydrothieno[2,3-b]pyridine-2-carboxylate LCMS (ES$^+$) RT 3.57 minutes, 401 (M+H)$^+$.

EXAMPLE 33

Ethyl 3-(4-cyanophenyl)-6-oxo-7-phenyl-6,7-dihydrothieno[2,3-b]pyridine-2-carboxylate LCMS (ES$^+$) RT 3.58 minutes, 401 (M+H)$^+$.

EXAMPLE 34

Ethyl 3-(3-fluorophenyl)-6-oxo-7-phenyl-6,7-dlihydrothieno[2,3-b]pyridine-2-carboxylate LCMS (ES$^+$) RT 3.78 minutes, 394 (M+H)$^+$. $C_{22}H_{16}NFO_3S$ requires C, 67.16%; H, 4.10%; N, 3.56%; found C, 67.06%; H, 4.10%; N, 3.54%.

EXAMPLE 35

Ethyl 3-(4-chlorophenyl)-6-oxo-7-phenyl-6,7-dihydrothieno[2,3-b]pyridine-2-carboxylate LCMS (ES$^+$) RT 4.05 minutes, 410 (M+H)$^+$. $C_{22}H_{16}NClO_3S$ requires C, 64.47%; H, 3.93%; N, 3.42%; found C, 64.31%; H, 3.93%; N, 3.45%.

EXAMPLE 36

Ethyl 3-(2,4-dichlorophenyl)-6-oxo-7-phenyl-6,7-dihydrothieno[2,3-b]pyridine-2-carboxylate LCMS (ES$^+$) RT 4.70 minutes, 445 (M+H)$^+$.

EXAMPLE 37

Ethyl 3-(2,5-dichlorophenyl-6-oxo-7-phenyl-6,7-dihydrothieno[2,3-b]pyridine-2-carboxylate LCMS (ES$^+$) RT 4.57 minutes, 445 (M+H)$^+$.

EXAMPLE 38

Ethyl 3-(5-fluoro-2-methoxyphenyl)-6-oxo-7-phenyl-6,7-dihydrothieno[2,3-b]pyridine-2-carboxylate LCMS (ES$^+$) RT 3.98 minutes, 424 (M+H)$^+$.

EXAMPLE 39

Ethyl 3-(2,6-dimethylphenyl)-6-oxo-7-phenyl-6,7-dihydrothieno[2,3-b]pyridine-2-carboxylate LCMS (ES$^+$) RT 4.04 minutes, 404 (M+H)$^+$.

EXAMPLE 40

Ethyl 6-oxo-7-phenyl-3-(3-pyridyl)-6,7-dihydrothieno[2,3-b]pyridine-2-carboxylate LCMS (ES$^+$) RT 3.00 minutes, 377 (M+H)$^+$.

EXAMPLE 41

Ethyl 6-oxo-7-phenyl-3-(2-trifluoromethylphenyl)-6,7-dihydrothieno[2,3-b]pyridine-2-carboxylate LCMS (ES$^+$) RT 3.80 minutes, 444 (M+H)$^+$.

EXAMPLE 42

Ethyl 6-oxo-7-phenyl-3-(3-trifluoromethylphenyl)-6,7-dihydrothieno[2,3-b]pyridine-2-carboxylate LCMS (ES$^+$) RT 3.97 minutes, 444 (M+H)$^+$.

EXAMPLE 43

Ethyl 6-oxo-7-phenyl-3-(4-trifluoromethylphenyl)-6,7-dihydrothieno[2,3-b]pyridine-2-carboxylate LCMS (ES$^+$) RT 3.99 minutes, 444 (M+H)$^+$.

EXAMPLE 44

Ethyl 6-oxo-3-phenyl-7-(3-pyridinyl)-6,7-dihydrothieno[2,3-b]pyridine-2-carboxylate A mixture of Intermediate 4 (299 mg, 1.0 mmol), pyridine-3-boronic acid (246 mg, 2.0 mmol), pyridine-N-oxide (115 mg, 1.2 mmol), copper(II) acetate (182 mg, 1.0 mmol) and pyridine (0.160 mL, 2.0 mmol) in DCM (20 mL) was stirred at r.t. for 3 days. The mixture was diluted with DCM (30 mL) and washed with saturated NH$_4$Cl(aq) plus ammonia (pH 10, 2×100 mL), dried (Na$_2$SO$_4$) and concentrated in vacuo. The crude product was purified by column chromatography on silica (3% MeOH in DCM) to give the title compound as a white solid (35 mg, 9%). δH (CDCl$_3$) 9.00 (1H, d, J 4.5 Hz), 8.95 (1H, s), 8.01 (1H, ddd, J 1.5, 2.4, 8.1 Hz), 7.76 (1H, dd, J 4.7, 8.1 Hz), 7.68–7.52 (4H, m), 7.55–7.52 (2H, m), 6.77 (1H, d, J 9.7 Hz), 4.31 (2H, q, J 7.1 Hz), 1.30 (3H, t, J 7.1 Hz). m/z (ES$^+$) 377.0 (M+H)$^+$.

EXAMPLE 45

Ethyl 7-benzyl-6-oxo-3-phenyl-6,7-dihydrothieno[2,3-b]pyridine-2-carboxylate

Sodium hydride (32 mg of 60% w/w suspension in oil, 0.8 mmol, 1.2 equiv.) was added to a solution of Intermediate 4 (200 mg, 0.67 mmol) in anhydrous DMF (5 mL) under nitrogen and cooled with an ice bath. The reaction was stirred for 5 minutes before adding benzyl bromide (0.12 mL, 1.0 mmol, 1.5 equiv.). The reaction was heated at 60° for 18 h. The reaction was partitioned between water and EtOAc, the EtOAc extracts were dried (MgSO$_4$) and then concentrated in vacuo. The crude residue was purified by chromatography on silica (0–20% EtOAc in DCM) to give the title compound as an off-white solid (80 mg). δH (CDCl$_3$) 7.60–7.20 (11H, m), 6.51 (1H, d, J 10 Hz), 5.33 (2H, s), 4.08 (2H, q, J 7 Hz), 1.07 (3H, t, J 7 Hz). LCMS (ES$^+$) RT 4.05 minutes, 390 (M+H)$^+$.

General Procedure for the Preparation of Ethyl 7-alkyl-6-oxo-3-phenyl-6,7-tetrahydrothieno[2,3-b]pyridine-2-carboxylates The compounds of the following Examples 46–56 were prepared by parallel synthesis using a Radleys Carousel reaction station (Radleys Ltd., Saffron Walden, U.K.) following a procedure similar to that described for Example 2. Each reaction tube in the Carousel was charged with the appropriate alkyl or arylalkyl halide (1.5 mmol, 1.5 equiv.), Intermediate 4 (200 mg, 0.67 mmol), polystyrene supported 2-tert-butylimino-2-diethylamino-1,3-dimethyl-perhydro-1,3,2-diazaphosphorine (PS-BEMP, 364 mg, 0.8 mmol, 1.2equiv.) and a magnetic stirrer bar. Anhydrous DMF (4 mL) was added to each tube and the reactions stirred at 65° under nitrogen for 48 h. Each reaction was partitioned between water and DCM and the combined DCM extracts dried (MgSO$_4$) and concentrated in vacuo. The crude products were purified on silica eluting with 0–20% EtOAc in DCM to give the title compounds as solids.

EXAMPLE 46

Ethyl 7-(cyclohexylmethyl)-6-oxo-3-phenyl-6,7-dihydrothieno[2,3-b]pyridine-2-carboxylate δH (CDCl$_3$) 7.40–7.35 (3H, m), 7.27–7.24 (3H, m), 6.42 (1H, d, J 10 Hz), 4.12 (2H, q, J 7 Hz), 3.95 (2H, d, J 7.5 Hz), 2.08–2.05 (1H, m), 1.67–1.53 (5H, m), 1.16–1.09 (5H, m), 1.11 (3H, t, J 7 Hz). LCMS (ES$^+$) RT 5.17 minutes, 396 (M+H)$^+$.

EXAMPLE 47

Ethyl 6-oxo-7-(1-phenylethyl)-3-phenyl-6,7-dihydrothieno[2,3-b]pyridine-2-carboxylate δH (CDCl$_3$) 7.30–7.18 (11H, m), 6.72 (1H, m), 6.49 (1H, d, J 10 Hz), 4.05–3.99 (2H, m), 1.91 (3H, d, J 7 Hz), 1.01 (3H, t, J 7 Hz). LCMS (ES$^+$) RT 4.29 minutes, 404 (M+H)$^+$.

EXAMPLE 48

Ethyl 7-(3-methoxybenzyl)-6-oxo-3-phenyl-6,7-dihydrothieno[2,3-b]pyridine-2-carboxylate δH (CDCl$_3$) 7.40–7.35 (3H, m), 7.29 (1H, d, J 10 Hz), 7.25–7.17 (3H, m), 6.93 (1H, m), 6.90 (1H, bs), 6.77 (1H, m), 6.50 (1H, d, J 10 Hz), 5.30 (2H, s), 4.08 (2H, q, J 7 Hz), 3.72 (3H, s), 1.07 (3H, t, J 7 Hz). LCMS (ES$^+$) RT 4.09 minutes, 420 (M+H)$^+$.

EXAMPLE 49

Ethyl 7-(2,6-difluorobenzyl)-6-oxo-3-phenyl-6,7-dihydrothieno[2,3-b]pyridine-2-carboxylate δH (CDCl$_3$) 7.41–7.35 (3H, m), 7.29–7.15 (4H, m), 6.85 (2H, t, J 8 Hz), 6.45 (1H, d, J 10 Hz), 5.45 (2H, s), 4.08 (2H, q, J 7 Hz), 1.06 (3H, t, J 7 Hz). LCMS (ES$^+$) RT 4.06 minutes, 426 (M+H)$^+$.

EXAMPLE 50

Ethyl 7-(3-methylbutyl)-6-oxo-3-phenyl-6,7-dihydrothieno[2,3-b]pyridine-2-carboxylate LCMS (ES$^+$) RT 4.64 minutes, 370 (M+H)$^+$.

EXAMPLE 51

Ethyl 7-allyl-6-oxo-3-phenyl-6,7-dihydrothieno[2,3-b]pyridine-2-carboxylate

LCMS (ES$^+$) RT 3.84 minutes, 340 (M+H)$^+$.

EXAMPLE 52

Ethyl 6-oxo-7-(2-phenylethyl)-3-phenyl-6,7-dihydrothieno[2,3-b]pyridine-2-carboxylate LCMS (ES$^+$) RT 3.45 minutes, 404 (M+H)$^+$.

EXAMPLE 53

Ethyl 7-(2-chlorobenzyl)-6-oxo-3-phenyl-6,7-dihydrothieno[2,3-b]pyridine-2-carboxylate LCMS (ES$^+$) RT 4.40 minutes, 424 (M+H)$^+$.

EXAMPLE 54

Ethyl 7-(3-chlorobenzyl)-6-oxo-3-phenyl-6,7-dihydrothieno[2,3-b]pyridine-2-carboxylate LCMS (ES$^+$) RT 4.45 minutes, 424 (M+H)$^+$.

EXAMPLE 55

Ethyl 7-(4-chlorobenzyl)-6-oxo-3-phenyl-6,7-dihydrothieno[2,3-b]pyridine-2-carboxylate LCMS (ES$^+$) RT 4.49 minutes, 424 (M+H)$^+$.

EXAMPLE 56

Ethyl 7-(2-morpholinoethyl)-6-oxo-3-phenyl-6,7-dihydrothieno[2,3-b]pyridine-2-carboxylate This compound was purified by chromatography on silica eluting with 0–20% THF in DCM. LCMS (ES$^+$) RT 2.52 minutes, 413 (M+H)$^+$.

EXAMPLE 57

Ethyl 7-(4-bromophenyl)-6-oxo-3-phenyl-6,7-dihydrothieno[2,3-b]pyridine-2-carboxylate To an oven dried flask was added in sequence 4-bromophenylboronic acid (5.0 g, 25 mmol), DCM (100 mL), pyridine (2.7 mL), Intermediate 4 (3.74 g, 12.5 mmol), copper(II) acetate (2.26 g, 12.5 mmol) and pyridine N-oxide (1.46 g). The reaction was stirred at room temperature for 72 h with the exclusion of moisture. The reaction was then diluted with DCM (100 mL), washed with 2M HCl(aq), NaHCO$_3$ (aq), dried (MgSO$_4$) and concentrated in vacuo. The crude product was purified by chromatography on silica (0–20% EtOAc in DCM) to give the title compound as a white solid (2.03 g). δH (DMSO-d6) 7.89 (2H, J 8.7 Hz), 7.58 (2H, J 8.7 Hz), 7.53–7.49 (3H, m), 7.46 (1H, d, J 9.7 Hz), 7.42–7.40 (2H, m), 6.57 (1H, d, J 9.7 Hz), 4.07 (2H, q, J 7.1 Hz), 1.06 (3H, t, J 7.1 Hz). LCMS (ES$^+$) RT 4.25 minutes, 456 (M+H)$^+$.

EXAMPLE 58

Ethyl 7-(4-morpholinophenyl)-6-oxo-3-phenyl-6,7-dihydrothieno[2,3-b]pyridine-2-carboxylate To a mixture of the compound of Example 57 (100 mg, 0.22 mmol), caesium carbonate (101 mg, 0.31 mmol), Pd(OAc)$_2$ (5 mg, 0.022 mmol, 10 mol %) and 2,2'-bis(diphenylphosphino)-1-1'-binaphthyl (BINAP) (21 mg, 0.033 mmol, 15 mol %) in toluene (2 mL) and under nitrogen was added morpholine (0.024 mL, 0.27 mmol). The reaction mixture was heated to 100° for 18 h. Solvent was removed in vacuo and the crude product purified by chromatography on silica (0–20% THF in DCM) to give the title compound as a white solid (40 mg).

δH (CDCl$_3$) 7.50–7.18 (8H, m), 7.01 (2H, d, J 9 Hz), 6.52 (1H, d, J 10 Hz), 4.06 (2H, q, J 7 Hz), 3.82 (4H, m), 3.22 (4H, m), 1.06 (3H, t, J 7 Hz). LCMS (ES$^+$) RT 3.82 minutes, 461 (M+H)$^+$.

EXAMPLE 59

6-oxo-3,7-diphenyl-6,7-dihydrothieno[2,3-b]pyridine-2-carboxylic acid

To a solution of the compound of Example 1 (4.53 g, 12.1 mmol) in 2:1 THF-water (150 mL) was added LiOH.H$_2$O (1.50 g, 36.2 mmol) and the reaction stirred for 36 h at r.t. The reaction was diluted with water 50 mL and 2M HCl(aq) added with stirring until a precipitate had formed (pH 1–2). The solid was filtered, washed with several portions of water and dried in a vacuum oven (50° C.) to afford the title compound as a white solid (4.2 g). δH (DMSO-d6) 13.00 (1H, bs), 7.70–7.40 (11H, m), 6.55 (1H, d, J 10 Hz). LCMS (ES$^+$) RT 3.10 minutes, 348 (M+H)$^+$.

EXAMPLE 60

2-[(4-Methylpiperazino)carbonyl]-3,7-diphenylthieno[2,3-b]pyridin-6(7H)-one

To a suspension of the compound of Example 59 (100 mg, 0.29 mmol) in DCM (2 mL) was added EDC (67 mg, 0.348 mmol) and HOBT (43 mg, 0.32 mmol) and the mixture stirred at r.t. for 15 minutes. A solution N-methyl piperazine (28 mg, 0.32 mmol) in DCM (0.5 mL) was added and the reaction stirred at r.t. for 18 h. The reaction mixture was diluted with DCM (10 mL), washed with water (2×5 mL), dried (MgSO$_4$) and concentrated in vacuo. The crude product was purified by chromatography on silica (0–20% THF in DCM) to give the title compound as an off-white solid (82 mg). δH (DMSO-d6) 7.67 (1H, dd, J 10, 1 Hz), 7.62–7.52 (3H, m), 7.51–7.40 (5H, m), 7.35–7.31 (2H, m), 6.51 (1H, dd, J 10, 1 Hz), 2.44 (8H, m), 1.88 (3H, s). LCMS (ES$^+$) RT 2.18 minutes, 430 (M+H)$^+$.

EXAMPLE 61

N-Ethyl-6-oxo-3,7-diphenyl-6,7-dihydrothieno[2,3-b]pyridine-2-carboxamide

EDC (66 mg, 0.35 mmol) and HOBT (43 mg, 0.32 mmol) were added to the compound of Example 59 (100 mg, 0.29 mmol) in DCM (2 mL). After 15 min ethylamine hydrochloride (26 mg, 0.32 mmol) and NMM (0.070 mL, 0.63 mmol) were added and the reaction mixture was stirred at r.t. overnight. Water (2 mL) and DCM (2 mL) were added, the suspension filtered through a hydrophobic frit and the organic phase concentrated in vacuo. The crude product was purified by column chromatography on silica (1% MeOH in DCM) to give the title compound as a white solid (95 mg, 88%). δH (DMSO-d6) 7.69–7.61 (3H, m), 7.59–7.49 (3H, m), 7.45 (1H, d, J 9.6 Hz), 7.44–7.42 (4H, m), 7.05 (1H, t, J 5.4 Hz), 6.54 (1H, d, J 9.6 Hz), 3.03 (2H, q, J 7.1 Hz), 0.84 (3H, t, J 7.1 Hz). LCMS (ES$^+$) RT 3.33 minutes, 375.0 (M+H)$^+$.

The following compounds of Examples 62–74 were prepared from the compound of Example 59 and the appropriate amine or amine hydrochloride by the method of Example 61.

EXAMPLE 62

N-(3-Hydroxypropyl)-6-oxo-3,7-diphenyl-6,7-dihydrothieno[2,3-b]pyridine-2-carboxamide LCMS (ES$^+$) RT 2.99 minutes, 405.0 (M+H)$^+$

EXAMPLE 63

6-Oxo-3,7-diphenyl-N-[2-(1-pyrrolidinyl)ethyl]-6,7-dihydrothieno[2,3-b]pyridine-2-carboxamide LCMS (ES$^+$) RT 2.29 minutes, 444.1 (M+H)$^+$

EXAMPLE 64

6-Oxo-3,7-diphenyl-N-(2-piperidinoethyl)-6,7-dihydrothieno[2,3-b]pyridine-2-carboxamide LCMS (ES$^+$) RT 2.33 minutes, 458.1 (M+H)$^+$

EXAMPLE 65

N-(3-Methoxypropyl-6-oxo-3,7-diphenyl-6,7-dihydrothieno[2,3-b]pyridine-2-carboxamide LCMS (ES$^+$) RT 3.28 minutes, 419.0 (M+H)$^+$

EXAMPLE 66

N-(2-Methoxyethyl)-6-oxo-3,7-diphenyl-6,7-dihydrothieno[2,3-b]pyridine-2-carboxamide LCMS (ES$^+$) RT 3.24 minutes, 405.0 (M+H)$^+$

EXAMPLE 67

3,7-Diphenyl-2-(1-pyrrolidinylcarbonyl)thieno[2,3-b]pyridin-6(7H)-one

LCMS (ES$^+$) RT 3.43 minutes, 401.0 (M+H)$^+$

EXAMPLE 68

N-[3-(1H-Imidazol-1-yl)propyl]-6-oxo-3,7-diphenyl-6,7-dihydrothieno[2,3-b]pyridine-2-carboxamide LCMS (ES$^+$) RT 2.28 minutes, 455.1 (M+H)$^+$

EXAMPLE 69

N-(2-Morpholinoethyl)-6-oxo-3,7-diphenyl-6,7-dihydrothieno[2,3-b]pyridine-2-carboxamide LCMS (ES$^+$) RT 2.28 minutes, 460.1 (M+H)$^+$

EXAMPLE 70

N-[3-(4-Methylpiperazino)propyl]-6-oxo-3,7-diphenyl-6,7-dihydrothieno[2,3-b]pyridine-2-carboxamide LCMS (ES$^+$) RT 2.16 minutes, 487.1 (M+H)$^+$

EXAMPLE 71

N-(3-Morpholinopropyl)-6-oxo-3,7-diphenyl-6,7-dihydrothieno[2,3-b]pyridine-2-carboxamide LCMS (ES$^+$) RT 2.26 minutes, 474.1 (M+H)$^+$

EXAMPLE 72

N,N-Diethyl-6-oxo-3,7-diphenyl-6,7-dihydrothieno[2,3-b]pyridine-2-carboxamide

LCMS (ES$^+$) RT 3.62 minutes, 403.0 (M+H)$^+$

EXAMPLE 73

N,N-Dimethyl-6-oxo-3,7-diphenyl-6,7-dihydrothieno[2,3-b]pyridine-2-carboxamide

LCMS (ES$^+$) RT 3.17 minutes, 375.0 (M+H)$^+$

EXAMPLE 74

N-Methyl-6-oxo-3,7-diphenyl-6,7-dihydrothieno[2,3-b]pyridine-2-carboxamide

LCMS (ES$^+$) RT 3.15 minutes, 361.0 (M+H)$^+$

EXAMPLE 75

6-Oxo-3,7-diphenyl-6,7-dihydrothieno[2,3-b]pyridine-2-carboxamide 1,1'-Carbonyldiimidazole (51 mg, 0.32 mmol) was added to the compound of Example 59 (100 mg, 0.29 mmol) in DMF (2 mL). After 15 min aq. ammonia (0.190 mL, 25% solution, 3.0 mmol) was added and the solution stirred at r.t. overnight. The mixture was concentrated in vacuo and azeotroped twice with heptane. The crude product was purified by column chromatography on silica (3% MeOH in DCM) to give the title compound as a white solid (74 mg, 74%). δH (DMSO-d6) 7.87–7.76 (3H, m), 7.75–7.68 (5H, m), 7.64–7.61 (2H, m), 7.54 (1H, d, J 9.6 Hz), 6.69 (1H, d, J 9.6 Hz), 6.25 (2H, br s). LCMS (ES$^+$) RT 2.95 minutes, 347.0 (M+H)$^+$.

EXAMPLE 76

N-Methoxy-N-methyl-6-oxo-3,7-diphenyl-6,7-dihydrothieno[2,3-b]pyridine-2-carboxamide N,O-Dimethylhydroxylamine hydrochloride (31 mg, 0.32 mmol) was added to a mixture of the compound of Example 59 (101 mg, 0.29 mmol), HOBT (55 mg, 0.41 mmol), EDC (78 mg, 0.41 mmol) and NMM (0.090 mL, 0.81 mmol) in DCM (3 mL). The mixture was stirred for 6 h at room temperature. DCM was added and the mixture washed with 2M HCl(aq). The organic phase was re-extracted with DCM. The combined organics were dried (Na$_2$SO$_4$) and concentrated in vacuo. The crude product was purified by column chromatography on silica (3.5% MeOH in DCM) to give the title compound as a white solid (95 mg, 84%). δH (DMSO-d6) 7.48–7.35 (3H, m), 7.34–7.30 (3H, m), 7.29–7.23 (3H, m), 7.16–7.13 (2H, m), 6.33 (1H, d, J 9.6 Hz), 3.26 (3H, s), 2.79 (3H, s). LCMS (ES$^+$) RT 3.27 minutes, 391 (M+H)$^+$.

EXAMPLE 77

6-Oxo-3,7-diphenyl-6,7-dihydrothieno[2,3-b]pyridine-2-carbonitrile

A mixture of cyanuric chloride (28 mg, 0.15 mmol) and the compound of Example 75 (52 mg, 0.15 mmol) in DMF (1.5 mL) was heated at 110° for 18 h. Two further portions of cyanuric chloride (14 mg, 0.075 mmol) were added and heating continued for a further 26 h. Water was added and the precipitate filtered off, washed with water and dried. The crude product was purified by column chromatography on silica (1% THF in DCM) to give the title compound as a white solid (35 mg, 71%). δH (DMSO-d6) 7.78 (1H, d, J 9.6 Hz), 7.71–7.67 (1H, m), 7.66–7.64 (1H, m), 7.64–7.59 (7H, m), 7.59–7.58 (1H, m), 6.67 (1H, d, J 9.6 Hz). LCMS (ES$^+$) RT 3.65 minutes, 329 (M+H)$^+$.

EXAMPLE 78

2-(1-Hydroxy-1-methylethyl)-3,7-diphenylthieno[2,3-b]pyridin-6(7H)-one

A solution of methyl magnesium iodide (0.084 mL of a 3M solution in ether, 0.25 mmol) was added drop-wise to a solution of the compound of Example 1 (47 mg, 0.13 mmol) in DCM (2 mL) at 0°. The mixture was allowed to warm to r.t. and stirred for 18 h. More methyl magnesium iodide (0.084 mL of a 3M solution in ether, 0.25 mmol) was added at 0° and the mixture stirred at r.t. for 1 h. DCM and NH$_4$Cl(aq) were added, the aqueous phase re-extracted with DCM and the combined organic extracts dried (Na$_2$SO$_4$) and concentrated in vacuo. The crude product was purified by column chromatography on silica (1% MeOH in DCM) to give the title compound as a yellow solid (36 mg, 80%). δH (DMSO-d6) 7.74–7.64 (3H, m), 7.60–7.52 (5H, m), 7.39 (2H, dd, J 7.8, 1.6 Hz), 7.10 (1H, d, J 9.5 Hz), 6.45 (1H, d, J 9.5 Hz), 2.58 (6H, s). LCMS (ES$^+$) RT 3.46 minutes, 362 (M+H)$^+$.

EXAMPLE 79

2-(Hydroxymethyl)-3,7-diphenylthieno[2,3-b]pyridin-6(7H)-one

Lithium borohydride (0.100 mL, 2M in THF, 0.2 mmol) was added to a solution of the compound of Example 1 (75 mg, 0.198 mmol) in THF (2 mL) and the reaction mixture was stirred at r.t. overnight. Two further portions of lithium borohydride (0.100 mL, 2M in THF, 0.198 mmol) were added and the mixture stirred for a further 6 h. The reaction was quenched by the addition of 2M HCl(aq) and the mixture neutralised by the addition of Na$_2$CO$_3$ The resulting precipitate was filtered off, washed with water and dried to give the title compound as a white solid (55 mg, 97%). δH (DMSO-d6) 7.68–7.41 (11H, m), 6.49 (1H, d, J 9.5 Hz), 5.57 (1H, br s), 4.50 (2H, br s). LCMS (ES$^+$) RT 3.10 minutes, 334.0 (M+H)$^+$.

EXAMPLE 80 tert-Butyl N-(6-oxo-3,7-diphenyl-6,7-dihydrothieno[2,3-b]pyridin-2-yl)carbamate

Triethylamine (0.076 mL, 0.55 mmol) and diphenylphosphoryl azide (0.119 mL, 0.55 mmol) were added to a solution of the compound of Example 59 (174 mg, 0.5 mmol) in dry tert-butanol (5 mL) and the mixture heated under reflux under nitrogen for 6 h. The cooled mixture was poured into saturated NaHCO$_3$(aq) (20 mL) and extracted with DCM (2×20 mL). The combined organic fractions were dried (MgSO$_4$), filtered and concentrated in vacuo. The crude product was purified by flash column chromatography on silica (EtOAc) to give the title compound (1 96 mg, 94%). δH (CDCl$_3$) 7.5–7.25 (11H, m), 6.70 (1H, br s), 6.46 (1H, d, J 9 Hz), 1.29 (9H, s). m/z (ES$^+$) 419 (M+H)$^+$.

EXAMPLE 81

2-Amino-3,7-diphenylthieno[2,3-b]pyridin-6(7H)-one

Trifluoroacetic acid (2 mL) was added to a solution of the compound of Example 80 (170 mg, 0.406 mmol) in DCM (2 mL) and the reaction mixture stirred for 2 h at r.t. The mixture was added to saturated NaHCO$_3$(aq) (20 mL) and the product extracted with DCM (2×20 mL). The combined organic fractions were dried (MgSO$_4$), filtered and concentrated in vacuo. The crude product was purified by flash column chromatography on silica (EtOAc), followed by radial chromatography (20% EtOH in DCM) to give the title compound as a buff solid (30 mg, 23%). δH (CDCl$_3$) 7.8–7.3 (13H, m), 6.58 (1H, d, J 9 Hz). m/z (ES$^+$) 319 (M+H)$^+$.

EXAMPLE 82 tert-Butyl N-methylsulfonyl-N-(6-oxo-3,7-diphenyl-6,7-dihydrothieno[2,3-b]pyridin-2-yl)carbamate Sodium bis(trimethylsilyl) amide (0.25 mL of a 1M solution in THF, 0.25 mmol) was added to a solution of the compound of Example 80 (105 mg, 0.25 mmol) in dry THF (5 mL) under a nitrogen atmosphere at 0°. After 30 min methane sulfonyl chloride (28.6 mg, 0.25 mmol) was added. The reaction mixture was allowed to warm to r.t. over 1 h then poured into saturated NaHCO$_3$(aq) (20 mL) and the product extracted with DCM (2×20 mL). The combined organic fractions were dried (MgSO$_4$), filtered and concentrated in vacuo. The crude product was purified by radial chromatography on silica (EtOAc) to give the title compound (115 mg, 92%). δH (CDCl$_3$) 7.6–7.28 (11H, m), 6.55 (1H, d, J 9 Hz), 2.68 (3H, s), 1.32 (9H, s). m/z (ES$^+$) 497 (M+H)$^+$.

EXAMPLE 83

N-(6-Oxo-3,7-diphenyl-6,7-dihydrothieno[2,3-b]pyridin-2-yl)methanesulfonamide

Trifluoroacetic acid (2.5 mL) was added to a solution of the compound of Example 82 (105 mg, 0.212 mmol) in DCM (2.5 mL) and the reaction mixture stirred for 2 h at r.t. The mixture was added to saturated NaHCO$_3$ solution (20 mL) and the product extracted with DCM (2×20 mL). The combined organic fractions were dried (MgSO$_4$), filtered and concentrated in vacuo. The crude product was purified by radial chromatography on silica (EtOAc) to give the title compound (62 mg, 74%). δH (CDCl$_3$) 7.6–7.25 (11H, m), 6.58 (1H, d, J 9 Hz), 6.31 (1H, br s), 2.53 (3H, s). m/z (ES$^+$) 397 (M+H)$^+$.

EXAMPLE 84

3,7-Diphenylthieno[2,3-b]pyridin-6(7H)-one

2M HCl(aq) (10 mL) was added to a solution of the compound of Example 59 (300 mg, 0.864 mmol) in dioxane (30 mL) and the mixture heated at reflux for 16 h. The cooled reaction mixture was poured into 10% NaOH(aq) (50 mL) and extracted with DCM (2×50 mL) The combined organic fractions were dried (Na$_2$SO$_4$), filtered and concentrated in vacuo to give the title compound as a white solid in quantitative yield. δH (CDCl$_3$) 7.83 (1H, d, J 9 Hz), 7.7–7.35 (10 H, m), 6.80 (1H, s), 6.67 (1H, d, J 9 Hz). m/z (ES$^+$) 304 (M+H)$^+$.

EXAMPLE 85

N-(6-Oxo-3,7-diphenyl-6,7-dihydrothieno[2,3-b]pyridin-2-yl)acetamide

Acetyl chloride (0.10 mL) was added to a solution of the compound of Example 81 (116 mg, 0.38 mmol) and pyridine (0.10 mL) in DCM (5 mL) and the mixture stirred at r.t. overnight. The reaction was quenched with MeOH and partitioned between DCM and water. The organic phase was dried (MgSO$_4$) and concentrated in vacuo. The crude product was purified by column chromatography on silica (0–5% MeOH in EtOAc) to give the title compound (39 mg, 21 %). δH(CDCl$_3$) 7.65 (1H, br s), 7.63–7.39 (11H, m), 6.63 (1H, d, J 9.5 Hz), 1.99 (3H, s). LCMS (ES$^+$) RT 2.621 minutes, 361 (M+H)$^+$.

EXAMPLE 86

1-Methyl-N-(6-oxo-3,7-diphenyl-6,7-dihydrothieno[2,3-b]pyridin-2-yl)-1H-imidazole-4-sulfonamide 1-Methyl-1H-imidazole-4-sulfonyl chloride (96 mg, 0.53 mmol) was added to a solution of the compound of Example 81 (136 mg, 0.44 mmol) and pyridine (52 mg, 0.66 mmol) in DCM (10 mL) and the reaction mixture stirred at r.t. overnight. The mixture was partitioned between DCM and NaHCO$_3$(aq). The organic phase was dried (MgSO$_4$) and concentrated in vacuo. The crude product was purified by column chromatography on silica (10% MeOH in DCM) to give the title compound (75 mg, 37%). δH (MeOH-d4) 7.60–7.48 (5H, m), 7.38–7.25 (6H, m), 7.23 (1H, m), 7.13 (2H, m), 6.48 (1H, d, J 9.5 Hz), 3.55 (3H, s). LCMS (ES$^+$) RT 2.90 minutes, 463 (M+H)$^+$.

EXAMPLE 87

Ethyl 7-[4-(benzyloxy)phenyl]-6-oxo-3-phenyl-6,7-dihydrothieno[2,3-b]pyridine-2-carboxylate A mixture of Intermediate 4 (2.50 g, 8.36 mmol), 4-(benzyloxy)phenylboronic acid (2.86 g, 12.5 mmol), copper(II) acetate (3.04 g, 16.7 mmol) and pyridine (2.7 mL, 33.4 mmol) in DCM (200 mL) was stirred at r.t. for 5 days. The mixture was diluted with DCM (100 mL) and filtered through celite. The filtrate was washed with 2M HCl(aq) (2×200 mL), dried (Na$_2$SO$_4$) and concentrated in vacuo. The crude product was purified by column chromatography on silica (3% MeOH in DCM) to give the title compound as a white solid (1.35 g, 34%). δH (CDCl$_3$) 7.52–7.35 (13H, m), 7.21–7.16 (2H, m), 6.60 (1H, d, J 9.6 Hz), 5.15 (2H, s), 4.14 (2H, q, J 7.1 Hz), 1.13 (3H, t, J 7.1 Hz). m/z (ES$^+$) 482.1 (M+H)$^+$.

EXAMPLE 88

Ethyl 7-[4-(hydroxymethyl)phenyl]-6-oxo-3-phenyl-6,7-dihydrothieno[2,3-b]pyridine-2-carboxylate A mixture of Intermediate 4 (300 mg, 1.0 mmol), 4-(hydroxymethyl)phenyl boronic acid (304 mg, 12.5 mmol), copper(II) acetate (913 mg, 5.0 mmol) and pyridine (0.404 mL, 5.0 mmol) in DCM (7 mL) was stirred at r.t. for 3 days. The mixture was diluted with DCM, washed with HCl (2M), dried (MgSO$_4$) and concentrated in vacuo. The crude product was purified by column chromatography on silica (50–100% EtOAc in isohexane) to give the title compound as a white solid (255 mg, 63%). δH (CDCl$_3$) 7.54 (2H, d, J 8.9 Hz), 7.44–7.28 (8H, m), 6.53 (1H, d, J 10.6 Hz), 4.72 (2H, s), 4.06 (2H, q, J 7.1 Hz), 1.05 (3H, t, J 7.1 Hz). LCMS (ES$^+$) RT 3.45 minutes, 406 (M+H)$^+$.

EXAMPLE 89

Ethyl 7-(4-hydroxyphenyl)-6-oxo-3-phenyl-6,7-dihydrothieno[2,3-b]pyridine-2-carboxylate A mixture of Intermediate 4 (554 mg, 1.86 mmol), 4-hydroxyphenyl boronic acid (511 mg, 3.71 mmol), copper(II) acetate (37 mg, 0.187 mmol), pyridine-N-oxide (350 mg, 3.71 mmol) and pyridine (0.370 mL, 3.71 mmol) in DCM (20 mL) was stirred at r.t. overnight. The reaction mixture was diluted with DCM, washed with NH$_4$Cl(aq) and water, dried (MgSO$_4$) and concentrated in vacuo. The crude product was purified by column chromatography on silica (5% MeOH in DCM) to give the title compound as a cream solid (484 mg, 73%). δH (DMSO-d6) 10.06 (1H, s), 7.54–7.50 (3H, m), 7.47–7.45 (3H, m), 7.37 (2H, d, J 9 Hz), 7.02 (2H, d, J 9 Hz), 6.58 (1H, d, J 10 Hz), 4.11 (2H, q, J 7 Hz), 1.09 (3H, t, J 7 Hz). LCMS (ES$^+$) 392.1 (M+H)$^+$.

EXAMPLE 90

Ethyl 7-[4-(2-hydroxyethoxy)phenyl]-6-oxo-3-phenyl-6,7-dihydrothieno[2,3-b]pyridine-2-carboxylate 2-Bromoethanol (0.148 mL, 2.08 mmol) was added to the compound of Example 89 (370 mg, 0.95 mmol) and Cs$_2$CO$_3$ (342 mg, 1.04 mmol) in DMF (5 mL) and the mixture heated at 80° for 2 days. The solvent was removed in vacuo and the residue partitioned between EtOAc and HCl (10%). The aqueous phase was extracted with EtOAc (2×20 mL). The combined organics were washed with brine, dried (MgSO$_4$) and concentrated in vacuo. The crude product was purified by column chromatography on silica (2% to 10% MeOH in DCM) to give the title compound (73 mg, 18%). δH (CDCl$_3$) 7.44–7.28 (8H, m), 7.07 (2H, d, J 8 Hz), 6.52 (1H, d, J 9.6 Hz), 4.12–3.93 (6H, m), 1.06 (3H, t, J 7.1 Hz). LCMS (ES$^+$) RT 3.42 minutes, 436 (M+H)$^+$.

EXAMPLE 91

Ethyl 7-{4-[2-(2-methyl-1H-imidazol-1-yl)ethoxy]phenyl}-6-oxo-3-phenyl-6,7-dihydrothieno[2,3-b]pyridine-2-carboxylate Pyridine (0.136 mL, 1.68 mmol) was added to a mixture of the compound of Example 90 (73 mg, 0.168 mmol) and tosylchloride (40 mg, 0.21 mmol) in DCM (2 mL) at 0°. The reaction mixture was stirred at 0° for 5 h then allowed to warm to r.t. The mixture was diluted with DCM (20 mL), washed with 2M HCl(aq), 10% NaOH(aq) and brine, dried (MgSO$_4$) and concentrated in vacuo. The crude product was purified by column chromatography on silica (50 to 80% EtOAc in isohexane) to give the intermediate tosylate, ethyl 7-[4-(2-[(4-methylphenyl)sulfonyl]oxyethoxy)phenyl]-6-oxo-3-phenyl-6,7-dihydro-1-benzothiophene-2-carboxylate, as a solid (73 mg, 12%). δH(CDCl$_3$) 7.78 (2H, d, J 8.6 Hz), 7.43–7.27 (10H, m), 6.93 (2H, d, J 8.6 Hz), 6.52 (1H, d, J 9.6 Hz), 4.38–4.35 (2H, m), 4.18–4.15 (2H, m), 4.07 (2H, q, J 7.1 Hz), 2.40 (3H, s), 1.06 (3H, t, J 7.1 Hz). LCMS (ES$^+$) RT 4.15 minutes, 590 (M+H)$^+$.

A mixture of this tosylate (70 mg, 0.12 mmol), 2-methylimidazole (11 mg, 0.13 mmol) and Cs$_2$CO$_3$ (43 mg, 0.13 mmol) in DMF (1 mL) was heated at 80° for 6 h. The solvent was removed in vacuo and the residue partitioned between DCM (15 mL) and NaHCO$_3$(aq) (15 mL). The organic phase was extracted with DCM (2×10 mL). The combined organics were dried (MgSO$_4$) and concentrated in vacuo. The crude product was purified by column chromatography on silica (10% MeOH in DCM) to give the title compound (20 mg, 34%). δH(CDCl$_3$) 7.43–7.28 (8H, m), 7.19–7.15 (2H, m), 7.01–6.90 (2H, m), 6.51 (1H, d, J 9.6 Hz), 4.25–4.20 (4H, br m), 4.06 (2H, q, J 7.1 Hz), 2.43 (3H, s), 1.05 (3H, t, J 7.1 Hz). LCMS (ES$^+$) RT 2.62 minutes, 500 (M+H)$^+$.

EXAMPLE 92

Ethyl 7-[4-(2-morpholinoethoxy)phenyl]-6-oxo-3-phenyl-6,7-dihydrothieno[2,3-b]pyridine-2-carboxylate To a mixture of the compound of Example 89 (100 mg, 0.256 mmol) and caesium carbonate (202 mg, 0.62 mmol) in dry DMF (5 mL) was added 2-(chloroethyl)morpholine hydrochloride (58 mg, 0.31 mmol) and the reaction heated at 60° under nitrogen for 48 h. The reaction was partitioned between water and EtOAc, the EtOAc extracts dried (MgSO$_4$) and concentrated in vacuo. The crude product was then purified by column chromatography on silica eluting with 0–5% MeOH in DCM to give the title compound as a white solid (68 mg). δH (CDCl$_3$) 7.44–7.20 (8H, m), 7.04 (2H, d, J 9 Hz), 6.51 (1H, d, J 10 Hz), 4.15–4.03 (4H, m), 3.68 (4H, m), 2.79 (2H, t, J 6 Hz), 2.54 (4H, m), 1.05 (3H, t, J 7 Hz). LCMS (ES$^+$) RT 2.53 minutes, 505 (M+H)$^+$.

EXAMPLE 93

Ethyl 6-oxo-3,7-diphenyl-4,5,6,7-tetrahydrothieno[2,3-b]pyridine-2-carboxylate

Hydrogen at 20 to 25 bar was applied to a mixture of the compound of Example 1 (185 mg), 10% ruthenium on carbon (64 mg) and EtOH (25 mL) stirred at 60 to 90° for 30 hours. The mixture was filtered to remove the catalyst and the filter was washed with EtOH (70 mL). The solution was concentrated in vacuo to give a crude product. This was purified by preparative HPLC (0.08% formic acid in acetonitrile, pH 2, Luna 2 C18 5 μm 250 mm) to give the title compound as a white solid (48 mg, 26%). δH (CDCl$_3$) 7.59–7.48 (3H, m), 7.47–7.36 (5H, m), 7.30 (2H, dd, J 8.5, 2.1 Hz), 4.10 (2H, q, J 7.3 Hz), 2.84 (2H, m), 2.75 (2H, m), 1.10 (3H, t, J 7.3 Hz). LCMS RT 4.1 minutes, 378 (M+H)$^+$

EXAMPLE 94

7-(4-Methoxybenzyl)-6-oxo-3-phenyl-6,7-dihydrothieno[2,3-b]pyridine-2-carbonitrile Sodium hydride (24 mg of 60% w/w dispersion in oil, 0.6 mmol) was added to a solution of Intermediate 12 (126 mg, 0.5 mmol) in dry DMF (4 mL) and stirred at r.t. for 10 mins under nitrogen. 4-Methoxybenzyl chloride (68 µL, 0.5 mmol) was added and the reaction mixture heated to 60° for 2 hours. The reaction was allowed to cool to r.t. and was partitioned between EtOAc (75 mL) and brine (50 mL). The organic layer was dried ($Na_2SO_4$), concentrated in vacuo and the crude product purified by column chromatography (silica, 10% EtOAc in DCM) to give the title compound as a white solid (93 mg, 50%). δH ($CDCl_3$) 7.48 (1H, d, J 9.6 Hz), 7.42–7.33(5H, m), 7.26 (2H, d, J 8.8 Hz), 6.77 (2H, d, J 8.8 Hz), 6.55 (1H, d, J 9.6 Hz), 5.19 (2H, s), 3.68 (3H, s). LCMS ($ES^+$) 395 $(M+H)^+$.

EXAMPLE 95

N-Allyl-6-oxo-3,7-diphenyl-6,7-dihydrothieno[2,3-b]pyridine-2-carboxamide

To a stirred solution of the compound of Example 59 (174 mg, 0.5 mmol) in dry DCM (5 mL) was added allyl amine (29 mg, 0.5 mmol), triethylamine (101 mg, 1 mmol), and a catalytic amount of 4-dimethylaminopyridine followed by EDC (96 mg, 0.5 mmol). The reaction mixture was stirred at r.t. for 4 h and then poured into 2M HCl(aq) (20 mL). The product was extracted with DCM (2×20 mL) and the combined organic fractions dried ($MgSO_4$), filtered and the solvent removed in vacuo. Purification by radial chromatography (silica, EtOAc) gave the title compound as a solid (70 mg). δH ($CDCl_3$) 7.7–7.1 (11H, m), 4.48 (1H, d, J 10 Hz), 5.6–5.4 (1H, m), 5.28 (1H, bs), 4.84 (1H, dd, J 10, 1 Hz), 4.69 (1H, dd, J 10, 1 Hz), 3.8–3.6 (2H, m). LCMS ($ES^+$) 387 $(M+H)^+$.

EXAMPLE 96

N-(2,3-dihydroxypropyl)-6-oxo-3,7-diphenyl-6,7-dihydrothieno[2,3-b]pyridine-2-carboxamide To a stirred solution of the compound of Example 95 (50 mg) in 8:1 acetone-water (10 mL) was added 4-methylmorpholine N-oxide (100 mg) followed by a catalytic amount of $OsO_4$. The reaction mixture was stirred for 16 h and then poured into saturated $NaHCO_3$ solution (20 mL). The product was extracted with DCM (2×20 mL) and the combined organic fractions dried over $MgSO_4$, filtered and solvent removed in vacuo. The crude product was purified by column chromatography (silica, 10% EtOH in DCM) to give the title compound as a solid (32 mg). δH ($CDCl_3$) 7.8–7.1 (11H, m), 6.44 (1H, d, J 10 Hz), 5.62 (1H, bs), 3.7–3.1 (5H, m). LCMS ($ES^+$) 421 $(M+H)^+$.

EXAMPLE 97

(6-Oxo-3,7-diphenyl-6,7-dihydrothieno[2,3-b]pyridin-2-yl)-urea

To a stirred solution of the monohydrochloride salt of the compound of Example 81 (0.177 g, 0.5 mmol) in dry pyridine (5 mL) was added excess trimethylsilyl isocyanate and the reaction stirred at r.t. for 16 h. The reaction was poured onto 2M HCl(aq) (20 mL) and extracted with DCM (2×20 mL). The combined organic fractions were dried over $MgSO_4$, filtered and solvent removed in vacuo. The crude product was purified by radial chromatography (silica, EtOAc) to give the title compound as a solid (6 mg). δH (DMSO-d6) 8.78 (1H, s), 7.8–7.55 (5H, m), 7.5–7.4 (6H, m), 6.48 (1H, d, J 10 Hz), 6.32 (2H, bs). LCMS ($ES^+$) 362 $(M+H)^+$.

EXAMPLE 98

1-Ethyl-3-(6-oxo-3,7-diphenyl-6,7-dihydrothieno[2,3-b]pyridin-2-yl)-urea

The title compound was prepared from the HCl salt of the compound of Example 81 and ethyl isocyanate following the method described for the compound of Example 97 to give the product as a solid (24 mg). δH (DMSO-d6) 8.59 (1H,s), 7.8–7.4 (11H, m), 6.67 (1H, t, J 5 Hz), 6.38 (1H, d, J 10 Hz), 3.1–2.9 (2H, m), 0.97 (3H, t, J 7 Hz). LCMS ($ES^+$) 390 $(M+H)^+$.

EXAMPLE 99

1-(2-Hydroxyethyl)-3-(6-oxo-3,7-diphenyl-6,7-dihydrothieno[2,3-b]pyridin-2-yl)-urea To a stirred suspension of the monohydrochloride salt of the compound of Example 81 (177 mg, 0.5 mmol) in dry DCM was added phosgene (0.26 mL of 1.93M solution in toluene, 0.5 mmol), followed by triethylamine (101 mg, 1.0 mmol). The reaction was stirred for 1 h at r.t. before adding more triethylamine (51 mg, 0.5 mmol) and ethanolamine (31 mg, 0.5 mmol). The reaction was stirred for a further hour and then poured into saturated $NaHCO_3$(aq) (20 mL). The product was extracted with DCM (2×20 mL), the combined organic fractions dried over $MgSO_4$, filtered and the solvent removed in vacuo. The crude product was purified by radial chromatography (silica, EtOAc) to give the title compound as a solid (34 mg). δH (DMSO-d6) 8.84 (1H,s), 7.8–7.3 (11H, m), 6.85 (1H, t, J 5 Hz), 6.41 (1H, d, J 10 Hz), 4.69 (1H, t, J 5 Hz), 3.4–3.2 (2H, m), 3.1–2.9 (2H, m). LCMS ($ES^+$) 406 $(M+H)^+$.

EXAMPLE 100

6-Oxo-3,7-diphenyl-6,7-dihydrothieno[2,3-b]pyridine-2-sulfonic acid methylamide

To a solution of Intermediate 13 (32 mg, 0.085 mmol) in DCM (5 mL) was added methylamine (40% solution in water, 0.17 mmol, 0.1 mL) and the reaction stirred at r.t. for 18 h. The reaction was partitioned between DCM and saturated $NaHCO_3$(aq) and the DCM layer dried over $MgSO_4$, filtered and concentrated in vacuo. The crude product was purified by column chromatography (silica, EtOAc) to give the title compound as an off-white solid (10 mg). δH ($CDCl_3$) 7.71 (2H, dt, J 8.5, 1.8 Hz), 7.73 (1H, d, J 9.6 Hz), 7.48–7.62 (5H, m), 7.40 (2H, m), 6.86 (1H, s), 6.63 (1H, d, J 9.6 Hz), 4.41 (1H, q, J 5.3 Hz), 2.68 (3H, d, J 5.3 Hz). LCMS ($ES^+$) RT 3.14 minutes, 397 $(M+H)^+$.

EXAMPLE 101

6-Oxo-6,7-diphenyl-6,7-dihydrothieno[2,3-b]pyridine-2-sulfonic acid pyrrolidine amide The title compound was prepared from Intermediate 13 (18 mg) and pyrrolidine (0.1 mL) following the method described for the compound of Example 100 to give the product as an off-white solid (4 mg). δH (CDCl$_3$) 7.89 (2H, m), 7.74 (1H, d, J 9.6 Hz), 7.48–7.60 (5H, m), 7.40 (2H, m), 6.87 (1H, s), 6.64 (1H, d, J 9.6 Hz), 3.24 (4H, m), 1.77 (4H, m). LCMS (ES$^+$) RT 3.47 minutes, 437 (M+H)$^+$.

EXAMPLE 102

7-[4-(2-Morpholinoethoxy)phenyl]-6-oxo-3-phenyl-6,7-dihydrothieno[2,3-b]pyridine The compound of Example 92 (91 mg, 0.18 mmol) was dissolved in dioxane (1 mL) and 4M HCl(aq) (1 mL) added and the mixture heated at reflux for 48 h. The reaction was partitioned between 2M NaOH(aq) and THF and the combined THF layers were dried (MgSO$_4$), filtered and concentrated in vacuo. The crude product was purified by column chromatography (silica, 0–10% MeOH in EtOAc) to give the title compound as an off-white solid (73 mg, 94%). δH (CDCl$_3$) 7.74 (1H, d, J 9.6 Hz), 7.33–7.28 (7H, m), 7.05–7.01 (2H, m), 6.75 (1H, s), 6.58 (1H, d, J 9.6 Hz), 4.12 (2H, t, J 5.7 Hz), 3.76–3.67 (4H), m), 2.78 (2H, t, J 5.7 Hz), 2.56–2.52 (4H, m). LCMS (ES$^+$) RT 2.46 minutes, 433 (M+H)$^+$.

EXAMPLE 103

7-[4-(2-Morpholinoethoxy)phenyl]-6-oxo-3-phenyl-6,7-dihydrothieno[2,3-b]pyridine-2-carboxylic acid A mixture of the compound of Example 92 (230 mg, 0.46 mmol), sodium hydroxide (91 mg, 2.28 mmol) and EtOH (5 mL) was heated at reflux for 18 h. EtOH was removed in vacuo and the residue treated with 2M HCl(aq) (2 mL) to give a white solid. The reaction was diluted with water and then freeze dried. The resultant solid was extracted with isopropanol and the extracts concentrated in vacuo to give the title compound as a white solid (97 mg). δH (DMSO-d6) 7.62–7.37 (8H, m), 7.21–7.16 (2H, m), 6.50 (1H, J 9.6 Hz), 4.20 (2H, t, J 5.7 Hz), 3.62–3.59 (4H, m), 2.76 (2H, t, J 5.7 Hz), 2.54–2.51 (4H, m). LCMS (ES$^+$) RT 2.35 minutes, 477 (M+H)$^+$.

EXAMPLE 104

7-[4-(2-Morpholinoethoxy)phenyl]-6-oxo-3-phenyl-6,7-dihydrothieno[2,3-b]pyridine-2-carboxamide To a suspension of the compound of Example 103 (120 mg, 0.25 mmol) in dry DMF (3 mL) was added 1,1'-carbonyldiimidazole (41 mg) and the reaction stirred for 1 h. A further portion of 1,1'-carbonyldiimidazole (5 mg) was added and the reaction stirred for 30 mins before adding aqueous ammonia (1.5 mL of 25% solution). The reaction was stirred for 2 h and then was diluted with water (20 mL). The product was extracted with EtOAc (2×15 mL) and the combined organic extracts washed with water (×2), brine (×2) and dried over MgSO$_4$. Solvent was removed in vacuo to give the title compound as a solid (128 mg). δH (CDCl$_3$) 7.52–7.49 (3H, m), 7.40–7.18 (5H, m), 7.10–7.00 (2H, m), 6.51 (1H, d, J 9.6 Hz), 5.34 (2H, bs), 4.12 (2H, t, J 5.7 Hz), 3.71–3.67 (4H, m), 2.79 (2H, t, J 5.7 Hz), 2.56–2.53 (4H, m). LCMS (ES$^+$) RT 2.28 minutes, 476 (M+H)$^+$.

EXAMPLE 105

7-[4-(2-Morpholinoethoxy)phenyl]-6-oxo-3-phenyl-6,7-dihydrothieno[2,3-b]pyridine-2-carbonitrile To a solution of the compound of Example 104 (128 mg, 0.27 mmol) in dry DCM (1.5 mL) was added pyridine (44 μL, 0.54 mmol) followed by trifluoroacetic anhydride (46 μL, 0.32 mmol). TLC showed the reaction was complete after 5 minutes and the reaction was then diluted with DCM (20 mL) and washed with 2M NaOH(aq) (20 mL). The DCM layer was separated, dried (MgSO$_4$), filtered and concentrated in vacuo. The resultant residue was co-evaporated with toluene (2×15 mL) to give the title compound as a solid (73 mg). δH (CDCl$_3$) 7.62 (1H, d, J 9.7 Hz), 7.51–7.45 (5H, m), 7.29–7.26 (2H, m), 7.08–7.04 (2H, m), 6.62 (1H, d, J 9.7 Hz), 4.14 (2H, t, J 5.6 Hz), 3.71–3.68 (4H, m), 2.81 (2H, t, J 5.6 Hz), 2.58–2.54 (4H, m). LCMS (ES$^+$) RT 2.47 minutes, 458 (M+H)$^+$.

EXAMPLE 106

Ethyl 7-[4-(2,3-dihydroxypropoxy)phenyl]-6-oxo-3-phenyl-6,7-dihydrothieno[2,3-b]pyridine-2-carboxylate A mixture of the compound of Example 89 (680 mg, 1.74 mmol), 2,2-dimethyl-1,3-dioxalan-4-ylmethyl p-toluenesulfonate (600 mg, 2.09 mmol), and caesium carbonate (680 mg, 2.09 mmol) in DMF (3 mL) was heated at 80° for 18 h. The reaction mixture was cooled and then partitioned between DCM (30 mL) and water (30 mL). The aqueous layer was extracted with two further portions of DCM (10 mL) and the combined organic layers washed with brine, dried (MgSO$_4$) and concentrated in vacuo. The crude product was purified by column chromatography (silica, 10–15% EtOAc in DCM) to give ethyl 7-[4-(2,2-dimethyl-[1,3]dioxan-4-ylmethoxy)phenyl]-6-oxo-3-phenyl-6,7-dihydrothieno[2,3-b]pyridine-2-carboxylate as a white solid (474 mg, 54%). δH (CDCl$_3$) 7.52–7.43 (8H, m), 7.25–7.20 (2H, m), 6.67 (1H, d, J 9.6 Hz), 4.66–4.58 (1H, m), 4.32–4.01 (5H, m), 1.58 (3H, s), 1.51 (3H, s), 1.22 (3H, t, J 7.1 Hz). LCMS (ES$^+$) RT 3.99 minutes, 505 (M+H)$^+$. This intermediate (450 mg) was dissolved in EtOH (10 mL) and a catalytic amount of Dowex® 50WX4-200 resin in H$^+$ form was added followed by water (1 mL). The reaction was heated at 50° overnight and then diluted with EtOH (10 mL) and filtered hot to remove Dowex® resin. The filtrate was concentrated in vacuo to give the title compound as an off-white solid (388 mg). δH (CDCl$_3$) 7.60–7.38 (8H, m), 7.27–7.24 (2H, m), 6.72 (1H, d, J 9.6 Hz), 6.30–4.23 (5H, m), 4.03–3.89 (2H, m), 1.26 (3H, t, J 7.1 Hz). LCMS (ES$^+$) RT 3.18 minutes, 488 (M+Na)$^+$, 466 (M+H)$^+$.

EXAMPLE 107

7-{4-[2-(2-Methyl-1H-imidazol-1-yl)ethoxy]phenyl}-6-oxo-3-phenyl-6,7-dihydrothieno[2,3-b]pyridine-2-carboxamide To a solution of the compound of Example 91 (134 mg, 0.27 mmol) in EtOH (0.5 mL) and water (0.73 mL) was added sodium hydroxide (0.27 mL of a 1M solution, 0.27 mmol) and the mixture heated at reflux for 5 h. The reaction was freeze dried to give 7-{4-[2-(2-Methyl-1H-imidazol-1-yl)ethoxy]phenyl}-6-oxo-3-phenyl-6,7-dihydrothieno[2,3-b]pyridine-2-carboxylic acid as a solid. LCMS (ES$^+$) RT 2.34 minutes, 472 (M+H)$^+$. This compound was dissolved in DMF (2 mL) and thionyl chloride (30 µL, 0.405 mmol) was added and the reaction stirred at r.t. for 5 mins. Aqueous ammonia (2 mL of a 25% solution) was added and the reaction stirred for 30 mins. The reaction was diluted with water (20 mL) and extracted with EtOAc (3×30 mL). The combined EtOAc extracts were washed with water (2×10 mL), brine (20 mL), dried (MgSO$_4$) and concentrated in vacuo to give the title compound as a solid (104 mg, 82%). δH (CDCl$_3$) 7.52–7.48 (3H, m), 7.37–7.33 (2H, m), 7.29–7.26 (2H, m), 7.20–7.18 (1H, m), 7.01–6.96 (3H, m), 6.90–6.88 (2H, m), 6.50 (1H, d, J 9.6 Hz), 4.23–4.20 (4H, m), 2.42 (3H, s). LCMS (ES$^+$) RT 2.28 minutes, 471 (M+H)$^+$.

EXAMPLE 108

7-{4-[2-(2-Methyl-1H-imidazol-1-yl)ethoxy]phenyl}-6-oxo-3-phenyl-6,7-dihydrothieno[2,3-b]pyridine-2-carbonitrile To a suspension of the compound of Example 107 (93 mg, 0.20 mmol) and pyridine (32 µL, 0.4 mmol) in DCM (1 mL) was added trifluoroacetic anhydride (34 µL, 0.24 mmol) and the reaction stirred at r.t. for 30 mins. A further 60 µL of trifluoroacetic anhydride was added and the reaction stirred for 18 h before being diluted with DCM (10 mL) and THF (5 mL). The mixture was washed with 2M NaOH(aq), brine and the organic layer separated and dried over MgSO$_4$. Solvent was removed in vacuo and the residue purified by column chromatography (silica, 2–5% MeOH in DCM) to give the title compound as a solid (60 mg, 67%). δH (CDCl$_3$) 7.62 (1H, d, J 9.7 Hz), 7.51–7.44 (5H, m), 7.30–7.27 (2H, m), 7.01–6.98 (2H, m), 6.89 (2H, d, J 0.9 Hz), 6.61 (1H, d, J 9.7 Hz), 4.30–4.20 (4H, m), 2.43 (3H, s). LCMS (ES$^+$) RT 2.46 minutes, 453 (M+H)$^+$.

EXAMPLE 109

7-{4-[2-(2-Methyl-1H-imidazol-1-yl)ethoxy]phenyl}-6-oxo-3-phenyl-6,7-dihydrothieno[2,3-b]pyridine To a solution of the compound of Example 91 (60 mg, 0.12 mmol) in dioxane (1 mL) was added 4M HCl(aq) (1 mL) and the mixture heated at reflux for 48 h. Reaction was diluted with 2M NaOH(aq) (5 mL) and extracted with DCM (2×10 mL). The combined DCM extracts were dried (MgSO4), filtered and concentrated in vacuo. The resultant solid was dried at 60° in a vacuum oven to afford the title compound (32 mg, 62%). δH (CDCl$_3$) 7.76 (1H, d, J 9.6 Hz), 7.42–7.30 (6H, m), 7.00–6.92 (4H, m), 6.76 (1H, s), 6.58 (1H, d, J 9.6 Hz), 4.26–4.20 (4H, m), 2.46 (3H, s). LCMS (ES$^+$) RT 2.48 minutes, 428 (M+H)$^+$.

EXAMPLE 110

Ethyl 7-[4-(2-methyl-1H-imidazol-1-ylmethyl)phenyl]-6-oxo-3-phenyl-6,7-dihydrothieno[2,3-b]pyridine-2-carboxylate To a suspension of the compound of Example 88 (130 mg, 0.32 mmol) in THF (2 mL) was added NaH (14 mg of 60% dispersion in oil, 0.35 mmol). DMF (0.5 mL) was added to aid solubility and the reaction was stirred for 1 h. Thionyl chloride (25 µL, 0.35 mmol) was added to the reaction mixture cooled in an ice-bath. The mixture was stirred in the ice-bath for 30 mins before quenching the reaction with water (20 mL) and basifying with NaHCO$_3$(aq). The product was extracted into DCM (2×15 mL) and the combined DCM layers dried over MgSO$_4$, filtered and concentrated in vacuo to give ethyl 7-(4-chloromethylphenyl)-6-oxo-3-phenyl-6,7-dihydrothieno[2,3-b]pyridine-2-carboxylate LCMS (ES$^+$) RT 3.97 minutes, 424 (M+H)$^+$. To a solution of this compound in DMF (1 mL) was added 2-methylimidazole (13 mg, 0.16 mmol) and caesium carbonate (52 mg, 0.16 mmol) and the mixture heated at 80° for 3 h. DMF was removed in vacuo and the residue purified by column chromatography (silica, 40–100% EtOAc in isohexane followed by 5% MeOH in DCM) and also mass directed hpic to give the title compound as a solid (3 mg). δH (MeOH-d4) 7.47–7.27 (10 H, m), 7.06 (1H, d, J 1.4 Hz), 6.82 (1H, d, J 1.4 Hz), 6.50 (1H, d, J 9.6 Hz), 5.26 (2H, s), 4.00 (2H, q, J 7.1 Hz), 2.28 (3H, s), 0.99 (3H, t, J 7.1 Hz). LCMS (ES$^+$) RT 2.53 minutes, 470 (M+H)$^+$.

EXAMPLE 111

Ethyl 7-(4-bromophenyl)-3-(2,4-difluorophenyl)-6-oxo-6,7-dihydrothieno[2,3-b]pyridine-2-carboxylate To an oven dried flask was added in sequence 4-bromophenylboronic acid (4.2 g, 20.88 mmol), DCM (100 mL), pyridine (1.7 mL), Intermediate 14 (3.5 g, 10.44 mmol), copper(II) acetate (3.8 g, 20.88 mmol) and pyridine N-oxide (992 mg). The reaction was stirred at room temperature for 7 days with the exclusion of moisture. A further equivalent each of Cu(OAc)$_2$, pyridine N-oxide and pyridine was added and reaction stirred for 20 h. The reaction was then diluted with DCM (100 mL), washed with 2M HCl(aq), NaHCO$_3$ (aq), dried (MgSO$_4$) and concentrated in vacuo. The crude product was purified by chromatography on silica (0–3% THF in DCM) to give the title compound as an off-white solid (1.03 g). LCMS (ES$^+$) RT 4.13 minutes, 489 (M+H)$^+$.

EXAMPLE 112

Ethyl 3-(2,4-difluorophenyl)-7-[4-(4-methylpiperazin-1-yl)phenyl]-6-oxo-6,7-dihydrothieno[2,3-b]pyridine-2-carboxylate hydrochloride The title compound was prepared from the compound of Example 111 (1.0 g, 2.04 mmol) and N-methylpiperazine (230 µL, 2.45 mmol) following the analogous procedure described for the compound of Example 58. The crude product was purified by column chromatography (silica, 1% NH$_3$(aq) 10% MeOH 90% DCM) to give the product as a yellow solid (320 mg). This solid was dissolved in DCM and treated with 4M HCl(aq). Solvent was removed in vacuo and the residue re-dissolved in hot DCM. The solution was allowed to cool and the resultant solid collected by filtration to give the title compound as an off-white solid (310 mg). δH (DMSO-d6) 7.66–7.52 (5H, m), 7.39–7.33 (3H, m), 6.67 (1H, d, J 9.6 Hz), 4.10 (2H, q, J 3.1 Hz), 3.50–3.10 (8H, m), 2.94 (3H, s), 1.19 (3H, q, J 3.1 Hz). LCMS (ES$^+$) RT 2.57 minutes, 510 (M+H)$^+$.

EXAMPLE 113

3-(2,4-Difluorophenyl)-7-[4-(4-methylpiperazin-1-yl)phenyl]-6-oxo-6,7-dihydrothieno[2,3-b]pyridine To a solution of the compound of Example 112 (310 mg, 0.61 mmol) in dioxane (35 mL) was added 4M HCl(aq) (20 mL) and the mixture heated at reflux for 18 h. Reaction had not reached completion and so a few drops of concentratedHCl were added and reflux continued for 5 h. The reaction was quenched with saturated $Na_2CO_3$(aq) and extracted with DCM (×3). The combined DCM extracts were dried ($Na_2SO_4$), filtered and concentrated in vacuo. The crude product contained a small amount of residual ester starting material. The product was therefore dissolved in EtOH (15 mL) and heated at reflux with NaOH (50 mg) for 16 h. Solvent was removed in vacuo and the residue partitioned between DCM and saturated $Na_2CO_3$(aq). The DCM layer was washed with $Na_2CO_3$(aq) (×3), dried ($Na_2SO_4$) and concentrated in vacuo to give the pure title compound as an off-white solid (280 mg). δH (DMSO-d6) 8.10–7.95 (2H, m), 7.86 (1H, dt, J 9.5, 2.6 Hz), 7.74–7.63 (4H, m), 7.55–7.52 (2H, m), 6.92 (1H, d, J 9.5 Hz), 3.72–3.67 (8H, m), 2.67 (3H,s). LCMS (ES$^+$) RT 2.47 minutes, 438 (M+H)$^+$.

EXAMPLE 114

1,4-Diphenyl-1,4-dihydro-pyrrolo[3,2-b]pyridin-5-one

Intermediate 17 (230 mg, 1.1 mmol) copper(II) acetate (22 mg, 0.11 mmol), pyridine N-oxide (209 mg, 3.3 mmol), and phenyl boronic acid (344 mg, 2.2 mmol) were suspended in DCM (5 mL) and treated with pyridine (0.33 mL, 3.3 mmol). The reaction was stirred at r.t. for eighteen hours, further copper(II) acetate (415 mg, 2.08 mmol) was added and the reaction stirred for a further four hours. The reaction mixture was diluted with DCM, washed with ammonium chloride solution, separated, dried and concentrated in vacuo. Chromatography (ethyl acetate-silica) gave the title compound. δH (DMSO-d6) 7.75 (1H, d, J 9.6 Hz), 7.57–7.34 (11H, m), 6.20 (1H, d, J 9.6 Hz), 5.66 (1H, dd, J 0.6, 3.1 Hz). LCMS (ES$^+$) RT 3.278 minutes, 287(M+H)$^+$.

EXAMPLE 115

4-(4-Methoxyphenyl)-1-phenyl-1,4-dihydro-pyrrolo[3,2-b]pyridin-5-one

The title compound was prepared from 4-methoxyphenylboronic acid and Intermediate 17 following the method described for the compound of Example 114. δH (DMSO-d6) 7.01 (1H, d, J 9.6 Hz), 7.8–7.6 (6H, m), 7.49 (1H, d, J 8.9 Hz), 7.27 (1H, d, J 8.9 Hz), 6.42 (1H, d, J 9.6 Hz), 5.91 (1H, d, J 2.8 Hz), 4.01 (3H, s). LCMS (ES$^+$) RT 3.299 minutes, 317(M+H)$^+$

EXAMPLE 116

Ethyl 6-Oxo-3-phenyl-7-pyridin-3-ylmethyl-6,7-dihydro-thieno[2,3-b]pyridine-2-carboxylate To a solution of Intermediate 4 (200 mg, 0.67 mmol) in DMF (5 mL) at 0° was added sodium hydride (60 mg, 1.5 mmol, 60% dispersion in mineral oil) and the solution stirred for 5 minutes. 3-(Bromomethyl)-pyridine (202 mg, 0.8 mmol) was added and the reaction heated at 65° for 18 hours. The reaction was poured into saturated ammonium chloride solution and the aqueous phase extracted with EtOAc (×3). The organic phases were dried (MgSO$_4$), filtered and the solvents removed in vacuo. Column chromatography (silica, 20% THF in DCM) gave the title product as an off white solid (110 mg). δH (CDCl$_3$) 9.00–8.25 (2H, bm), 7.76 (1H, d, J 7.8 Hz), 7.40–7.35 (3H, m), 7.32 (1H, d, J 9.2 Hz), 7.26–7.18 (3H, m), 6.51 (1H, d, J 9.2 Hz), 5.33 (2H, s), 4.11 (2H, q, J 7.1 Hz), 1.09 (3H, t, J 7.1 Hz). LCMS (ES$^+$) RT 3.25 minutes, 391 (M+H)$^+$

EXAMPLE 117

Ethyl 7-(1-Benzyloxycarbonyl-piperidin-4-ylmethyl)-6-oxo-3-phenyl-6,7-dihydro-thieno[2,3-b]pyridine-2-carboxylate To a solution of Intermediate 4 (1.0 g, 3.35 mmol) in DMF (10 mL) at 0° was added sodium hydride (160 mg, 4.0 mmol, 60% dispersion in mineral oil) and the solution stirred for 5 minutes. N-Benzyloxycarbonyl-4-bromomethylpiperidine (1 g, 4 mmol) was added and the reaction heated at 65° for 18 hours. The reaction was poured into saturated ammonium chloride solution and the aqueous phase extracted with EtOAc (×3). The organic phases were dried (MgSO$_4$), filtered and the solvents removed in vacuo. Column chromatography (silica, 0–15% EtOAc in DCM) gave the title product as an off white solid (410 mg). δH (CDCl$_3$) 7.40–7.36 (3H, m), 7.30–7.23 (8H, m), 6.42 (1H, d, J 9.6 Hz), 5.06 (2H, s), 4.28–3.80 (4H, bm), 4.13 (2H, q, J 7.0 Hz), 2.80 (2H, m), 2.26 (1H, m), 1.70 (2H, m), 1.42 (2H, m), 1.12 (3H, t, J 7.0 Hz). LCMS (ES$^+$) RT 4.24 minutes, 531 (M+H)$^+$

EXAMPLE 118

Ethyl 6-Oxo-3-phenyl-7-piperidin-4-ylmethyl-6,7-dihydro-thieno[2,3-b]pyridine-2-carboxylate The compound of Example 117 (400 mg) was dissolved in EtOH (20 mL) and 10% palladium on carbon (40 mg) added. A hydrogen atmosphere (1 atmosphere) was applied and the reaction allowed to stir at ambient temperature for 18 hours. The reaction was filtered and the solvents removed in vacuo to give the title product as a white solid (210 mg). δH (CDCl$_3$) 7.50–7.45 (3H, m), 7.28–7.20 (3H, m), 6.42 (1H, d, J 9.6 Hz), 4.12 (2H, q, J 7.1 Hz), 3.98 (2H, d, J 7.4 Hz), 3.05 (2H, m), 2.55 (2H, m), 2.18 (1H, m), 1.60 (2H, m), 1.30 (2H, m), 1.11 (3H, t, J 7.1 Hz). LCMS (ES$^+$) RT 2.43 minutes, 397 (M+H)$^+$

EXAMPLE 119

Ethyl 7-(1-Methanesulfonyl-piperidin-4-ylmethyl)-6-oxo-3-Phenyl-6,7-dihydro-thieno[2,3-b]pyridine-2-carboxylate The compound of Example 118 (104 mg, 0.26 mmol) was dissolved in DCM (5 mL) and triethylamine (73 μL) followed by methanesulphonylchloride (40 μL, 0.28 mmol) added. The reaction was allowed to stir at ambient temperature for 18 hours. The reaction was diluted with brine and extracted with DCM (×3). The organic phases were washed with saturated NaHCO$_3$ solution and dried (MgSO$_4$). The reaction was filtered and the solvents removed in vacuo to give the title product as a white solid (120 mg). δH (CDCl$_3$)

7.45–7.30 (3H, m), 7.27–7.10 (3H, m), 6.43 (1H, d, J 9.4 Hz), 4.12 (2H, q, J 7.1 Hz), 4.02 (2H, d, J 7.2 Hz), 3.75 (2H, m), 2.70 (3H, s), 2.61 (2H, m), 2.20 (1H, m), 1.82 (2H, m), 1.55 (2H, m), 1.12 (3H, t, J 7.1 Hz). LCMS (ES$^+$) RT 3.55 minutes, 475 (M+H)$^+$

EXAMPLE 120

Ethyl 7-(2-nitrophenyl)-6-oxo-3-phenyl-6,7-dihydrothieno[2,3-b]pyridine-2-carboxylate Sodium hydride (440 mg of a 60% suspension in mineral oil, 11 mmol) was added portionwise to a suspension of Intermediate 4 (2.99 g, 10 mmol) in DMF (50 mL) at r.t. 1-Fluoro-2-nitrobenzene (1.48 mL, 15 mmol) was added and the mixture heated at 80° for 4 days. The reaction was quenched with a few drops of water and the solvent removed in vacuo. Purification by column chromatography on silica (DCM to 5% MeOH in DCM then in 2% THF in DCM) gave the title compound (807 mg, 19%) as a yellow solid. δH (DMSO-d6) 8.44 (1H, dd, J 1.3, 8.2 Hz), 8.17–8.08 (2H, m), 8.03–7.98 (1H, m), 7.61–7.57 (4H, m), 7.53–7.50 (2H, m), 6.62 (1H, d, J 9.7 Hz), 4.14 (2H, q, J 7.1 Hz), 1.12 (3H, t, J, 7.1 Hz).). LCMS (ES$^+$) RT 3.748 minutes, 421.0 (M+H)$^+$.

EXAMPLE 121

Ethyl 7-(2-aminophenyl)-6-oxo-3-phenyl-6,7-dihydrothieno[2,3-b]pyridine-2-carboxylate A mixture of the compound of Example 120 (455 mg, 1.08 mmol) and palladium on charcoal (10% Pd wt/wt, 90 mg) in EtOH (20 mL) was stirred under an atmosphere of hydrogen (balloon) for 45 h. The catalyst was filtered off and the filtrate concentrated in vacuo. Purification by column chromatography on silica (3% to 5% THF in DCM) gave the title compound as a pale yellow solid (257 mg, 61%). δH (DMSO-d6) 7.59–7.52 (3H, m), 7.48–7.44 (3H, m), 7.33–7.28 (1H, m), 7.16 (1H, dd, J 1.5, 7.8 Hz), 6.98 (1H, dd, J 1.2, 8.2 Hz), 6.77–6.73 (1H, m), 6.59 (1H, d, J 9.6 Hz), 5.33 (2H, br s), 4.12 (2H, q, J 7.1 Hz), 1.12 (3H, t, J 7.1 Hz). ). LCMS (ES$^+$) RT 3.581 minutes, 391.0 (M+H)$^+$.

EXAMPLE 122

Ethyl 7-(2-ethylaminophenyl)-6-oxo-3-phenyl-6,7-dihydrothieno[2,3-b]pyridine-2-carboxylate Obtained from the compound of Example 120 by the method of Example 121 using longer reaction times. White solid. δH (DMSO-d6) 7.60–7.54 (3H, m), 7.50–7.45 (3H, m), 7.43–7.39 (1H, m), 7.18 (1H, dd, J 1.5, 7.7 Hz), 6.93 (1H, d, J 7.7 Hz), 6.79–6.75 (1H, m), 6.59 (1H, d, J 9.6 Hz), 5.47 (1H, t, J 5.8 Hz), 4.13 (2H, q, J 6.9 Hz), 3.18 (2H, qn, J 6.7 Hz), 1.13 (3H, t, J 7.0 Hz), 1.11 (3H, t, J 7.1 Hz). LCMS (ES$^+$) RT 3.947 minutes, 419.1 (M+H)$^+$.

EXAMPLE 123

7-(2—Nitrophenyl)-6-oxo-3-phenyl-6,7-dihydrothieno[2,3-b]pyridine-2-carboxylic acid A mixture of the compound of Example 120 (150 mg, 0.357 mmol) and lithium hydroxide monohydrate (30 mg, 0.714 mmol) in dioxane (3 mL) and water (3 mL) was heated under reflux for 1.5 h. The dioxane was removed in vacuo, the aqueous residue acidified (2M HCl) and the precipitate filtered off and dried to give the title compound as a pale orange solid (112 mg, 80%). δH (DMSO-d6) 13.06 (1H, br s), 8.29 (1H, dd, J 1.3, 8.2 Hz), 8.02–7.93 (2H, m), 7.88–7.84 (1H, m), 7.46–7.35 (6H, m), 6.46 (1H, d, J 9.7 Hz). LCMS (ES$^+$) RT 3.137 minutes, 393.0 (M+H)$^+$.

EXAMPLE 124

7-(2—Nitrophenyl)-6-oxo-3-phenyl-6,7-dihydrothieno[2,3-b]pyridine-2-carboxamide

A mixture of the compound of Example 123 (105 mg, 0.268 mmol) and 1,1'-carbonyldiimidazole (65 mg, 0.40 mmol) in DMF (3 mL) was stirred at r.t. for 45 min. Concentrated ammonia solution (1 mL) was added and the mixture stirred overnight at r.t. Volatiles were removed in vacuo, the residue taken up in DCM, washed 2M HCl(aq), dried (Na$_2$SO$_4$), and concentrated in vacuo. Purification by column chromatography on silica (4% MeOH in DCM) gave the title compound as a yellow solid (42 mg). δH (DMSO-d6) 8.28 (1H, dd, J 1.3, 8.2 Hz), 7.99 (1H, dt, J 1.4, 7.8 Hz), 7.92 (1H, dd, J 1.4, 7.8 Hz), 7.87–7.82 (1H, m), 7.54–7.47 (3H, m), 7.46–7.37 (3H, m), 6.44 (1H, d, J 9.7 Hz), 6.21 (2H, v br). LCMS (ES$^+$) RT 2.997 minutes, 392.0 (M+H)$^+$.

EXAMPLE 125

Ethyl 7-(2-chlorophenyl)-6-oxo-3-phenyl-6,7-dihydrothieno[2,3-b]pyridine-2-carboxylate tert-Butyl nitrite (0.145 mL, 1.22 mmol) was added to a suspension of copper (II) chloride (120 mg, 0.894 mmol) in acetonitrile (10 mL) at 0° C. After 10 min, a solution of the compound of Example 121 (317 mg, 0.813 mmol) in acetonitrile (5 mL) was added. The mixture was stirred at 0° for 30 min then warmed to r.t. The solvent was removed in vacuo, the residue dissolved in DCM, washed HCl (2M), dried (Na$_2$SO$_4$) and concentrated in vacuo. Purification by column chromatography on silica (2% to 3% THF in DCM) gave the title compound as a yellow solid (163 mg, 49%). δH (DMSO-d6) 7.91 (1H, ddd, J 1.7, 7.7 Hz), 7.86–7.83 (1H, m), 7.78–7.70 (2H, m), 7.60–7.57 (4H, m), 7.53–7.49 (2H, m), 6.66 (1H, d, J 9.7 Hz), 4.13 (2H, q, J 7.1 Hz), 1.11 (3H, t, J 7.1 Hz). LCMS (ES$^+$) RT 3.944 minutes, 410.0 (M+H)$^+$.

EXAMPLE 126

7-(2-Chlorophenyl)-6-oxo-3-phenyl-6,7-dihydrothieno[2,3-b]pyridine-2-carboxylic acid Obtained from the compound of Example 125 by the method of Example 123. Off-white solid. δH (DMSO-d6) 13.09 (1H, br s), 7.86–7.82 (1H, m), 7.78–7.76 (1H, m), 7.71–7.64 (2H, m), 7.52–7.41 (6H, m), 6.58 (1H, d, J, 9.7 Hz). LCMS (ES$^+$) RT 3.247 minutes, 381.9 (M+H)$^+$.

EXAMPLE 127

7-(2-Chlorophenyl)-6-oxo-3-phenyl-6,7-dihydrothieno[2,3-b]pyridine-2-carboxamide A mixture of the compound of Example 126 (125 mg, 0.328 mmol) and 1,1'-carbonyldiimidazole (80 mg, 0.49 mmol) in DMF (3 mL) was stirred at r.t. for 90 min. Concentrated ammonia solution (0.5 mL) was added and the mixture stirred for 1 h. Volatiles were removed in vacuo. The residue was treated with 2M HCl(aq) and the resulting solid filtered off and dried. Purification by column chromatography on silica (3% MeOH in DCM) gave the title compound as a pale brown solid (105 mg, 84%). δH (DMSO-d6) 7.91–7.89 (1H, m), 7.83–7.80 (1H, m), 7.76–7.69 (2H, m), 7.66–7.59 (3H, m), 7.56–7.53 (2H, m), 7.51 (1H, d, J 9.7 Hz), 6.62 (1H, d, J 9.6 Hz), 6.2 (2H, br s). LCMS (ES$^+$) RT 3.120 minutes, 380.8 (M+H)$^+$.

EXAMPLE 128

6-Oxo-3,7-diphenyl-6,7-dihydrothieno[2,3-b]pyridine-2-carbothioamide

Hydrogen sulphide was bubbled through a solution of the compound of Example 77 (539 mg, 1.64 mmol) in pyridine (1 0 mL) and triethylamine (0.5 mL) for 30 minutes. The reaction was left to stand for 60 h at r.t. and then nitrogen bubbled through the mixture to ensure the solution was purged of H$_2$S. The solution was diluted with DCM and washed with water (×2), 2M HCl(aq) (×2) and brine. The organic layer was separated, dried (Na$_2$SO$_4$) and concentrated in vacuo. The crude product was recrystallised from DCM-hexane to give the title compound as a solid (327 mg, 40%). δH (DMSO-d6) 9.70 (1H, s), 7.70–7.47 (9H, m), 7.45 (2H, m), 7.38 (1H, d J 9.6 Hz), 6.52 (1H, d, J 9.6 Hz). LCMS (ES$^+$) RT 3.33 minutes, 385 (M+Na)$^+$, 363 (M+H)$^+$.

EXAMPLE 129

7-(2-chlorophenyl)-6-Oxo-3phenyl-6,7-dihydrothieno[2,3-b]pyridine-2-carbothioamide To a mixture of Lawesson's reagent (26.3 mg, 0.065 mmol) and the compound of Example 127 (50 mg, 0.13 mmol) was added toluene (10 mL) and the reaction heated at 110° for 1 h. A further portion of Lawesson's reagent (52.6 mg, 0.13 mmol) was added and reaction heated for 6.5 h. The reaction was diluted with DCM, washed with water, dried (Na$_2$SO$_4$) and concentrated in vacuo. The crude product was purified by column chromatography (silica, 5–10% EtOAc in DCM) to give the title compound as a yellow solid (10 mg, 20%). δH (MeOH-d4) 7.67 (1H, m), 7.58–7.46 (7H, m), 7.40 (3H, m), 6.48 (1H, d, J 9.6 Hz). LCMS (ES$^+$) RT 3.41 minutes, 397 (M+H)$^+$.

The following assays and animal models can be used to demonstrate the potency and selectivity of the compounds according to the invention. In each assay an IC50 value was determined for each test compound and represents the concentration of compound necessary to achieve 50% inhibition.

Preparation of Activated Human P38α for Inhibitor Assays.

Purification of Human p38α

Human p38α, incorporating an N-terminal (His)6 tag, was expressed in baculovirus-infected High-Five™ cells (Invitrogen) according to the manufacturers instructions. The cells were harvested 72 h post-infection and lysed in phosphate buffered saline (PBS) containing 1% (w/v) β-octylglucoside and Complete, EDTA-free™ protease inhibitors (Roche Molecular Biochemicals). The lysate was centrifuged at 35000×g for 30 min at 4° C. and the supernatant applied to a NiNTA™ column (Qiagen). Bound protein was eluted by 150 mM imidazole in PBS (after a wash with 15 mM imidazole in PBS) and directly applied to a HiTrap Q™ column (AP Biotech). Bound protein was eluted using a 20 column volume, 0 to 1M NaCl gradient. Fractions containing (His)6-p38 were aliquotted and stored at −70° prior to their activation.

Preparation of GST-MKK6EE-Containing Lysates

*E. coli* (BL21 pLysS) expressing the constituitively activated form of human MKK6 fused with an N-terminal glutathione-S-transferase tag (GST-MKK6EE) were harvested by centrifugation and frozen at −70°. Cells were lysed by resuspension in ⅒th the culture volume of PBS containing Complete, EDTA-free™ protease inhibitors followed by sonication on ice for 4×15 sec. Cell debris was removed by centrifugation at 35,000×g and the resultant supernatant stored in aliquots at −70°.

Activation of (His)6-p38

0.45 mL of purified (His)6-p38 was incubated with 50 μL of the GST-MKK6EE-containing lysate for 30 min at 23° in the presence of 1 mM β-glycerophosphate, 10 mM MgCl$_2$ and 9 mM ATP. The extent of activation was monitored by mass spectrometric detection of the doubly-phosphorylated form of (His)6-p38, which routinely comprised greater than 90% of the final (His)6-p38 preparation. The activated (His)6-p38 was then diluted ×10 in PBS and repurified using the method described above. The concentration of purified, activated (His)6-p38 was measured by UV absorbance at 280 nm using A280,0.1 %=1.2 and the preparation stored in aliquots at −70° prior to its use in inhibitor assays.

P38 Inhibition Assays

Inhibition of Phosphorylation of Biotinylated Myelin Basic Protein (MBP)

The inhibition of p38 catalysed phosphorylation of biotinylated MBP is measured using a DELFIA based format. The assay was performed in a buffer comprising, 20 mM HEPES (pH 7.4), 5 mM MgCl$_2$ and 3mM DTT. For a typical IC50 determination, biotinylated MBP (2.5 μM) was incubated at room temperature in a streptavidin-coated microtitre plate together with activated gst-p38 (10 nM) and ATP (1 μM) in the presence of a range of inhibitor concentrations (final concentration of DMSO is 2 percent). After fifteen minutes the reaction was terminated by the addition of EDTA (75 mM). The microtitre plate was then washed with Tris buffered saline (TBS), prior to the addition of 100 μl of anti-phospho MBP antibody (mouse) together with europium-labeled anti-mouse IgG antibody. After one hour at room temperature the plate was again washed in TBS followed by the addition of Enhancement solution (PerkinElmer Wallac). Fluorescence measurements were performed after a further fifteen minutes at room temperature. IC50 values are determined from the plot of Log$_{10}$ inhibitor concentration (x-axis) versus percentage inhibition of the fluorescence generated by a control sample in the absence of inhibitor (y-axis).

Purification of Human Peripheral Bood Mononuclear Cells

Peripheral blood mononuclear cells (PBMC) were isolated from normal healthy volunteers. Whole blood was taken by venous puncture using heparinised vacutainers (Becton Dickinson), diluted 1 in 4 in RPMI 1640 (Gibco, UK) and centrifuged at 400 g for 35 min over a Ficoll-paque gradient (Amersham-Pharmacia Biotech, UK). Cells at the interface were removed and washed once followed by a low speed spin (250 g) to remove platelets. Cells were then resuspended in DMEM containing 10% FCS, penicillin 100 units ml$^{-1}$, streptomycin 50 μg ml$^{-1}$ and glutamine 2 mM (Gibco, UK).

Inhibitor Dilutions

Inhibitor stocks (20 mM) were kept as a frozen solution (−20° C.) in DMSO. Serial dilutions of inhibitors were performed in DMSO as 250-times concentrated stocks. Inhibitors were diluted 1 in 250 into tissue culture media, prewarmed to 37° C. and transferred to plates containing PBMC. PBMC and inhibitors were incubated together for 30 mins prior to addition of LPS. Inhibitors used in whole blood assays were prepared according to a different regime. Using the same stock solution serial dilutions of inhibitors were performed in DMSO. Inhibitors were then diluted 1 in 500 straight into whole blood in a volume of 1 μL. Inhibitor was incubated with whole blood for 30 mins prior to the addition of LPS.

LPS Stimulation of PBMC

PBMC were resuspended at a density of $2 \times 10^5$ cells/well in flat bottomed 96 well tissue culture treated plates. After the addition of inhibitor cells were stimulated with an optimal dose of LPS (*E Coli* strain B5:055, Sigma, at a final concentration of 1 μg ml$^{-1}$) and incubated at 37° C. in 5% $CO_2$/95% air for 18 hours. TNF-α levels were measured from cell free supernatants by sandwich ELISA (BioSource #CHC1751).

LPS Stimulation of Whole Blood

Whole blood was taken by venous puncture using heparinised vacutainers (Becton Dickinson), and 500 μl of blood aliquoted into each well of a 24 well tissue culture treated plate. After the addition of inhibitor cells were stimulated with an optimal dose of LPS (*E coli* strain B5:055, Sigma, at a final concentration of 1 μg ml$^{-1}$) and incubated at 37° C. without $CO_2$ for 18 hours. TNF-α levels were measured from cell free supernatants by sandwich ELISA (BioSource #CHC1751).

Rat LPS Induced TNF Release

Male Lewis rats (1 80–200 g) are anaesthetised with Isofluor and injected i.v. with LPS* in a volume of 0.5 ml sterile saline. After 90 minutes blood is collected into EDTA tubes for preparation of plasma samples. Plasma is stored at −70° C. prior to assay for TNFα by commercial ELISA.

Rat CIA

Female Lewis rats (180–200 g) are anaesthetised with Isofluor and immunised i.d. at the base of the tail with 2×100 μl of emulsion containing 4 mg/ml bovine collagen II in 0.01M acetic acid and Freund's Incomplete Adjuvant at a ratio of 1:1.

A polyarthritis develops with onset from about 13 days post sensitisation. The disease is mainly confined to the ankles and is quantified by plethysmometry. Results are expressed as change in paw volume over time.

In the p38 inhibitor assay compounds of the invention have IC$_{50}$ values of around 30 μM and below. The more active compounds have IC$_{50}$ values of around 500 nM and below. The compounds of the invention are clearly potent inhibitors of p38 kinase, especially p38α kinase.

The invention claimed is:

1. A compound of formula (1a):

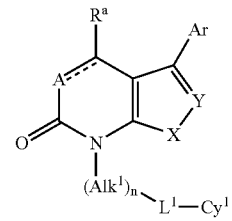

wherein:
the dashed line represents an optional bond;
A is a —N= atom or a —N(R$^b$)—, —C(R$^b$)= or —C(R$^b$)(R$^c$)— group;
R$^a$, R$^b$ and R$^c$ are each independently a hydrogen atom or an optionally substituted C$_{1-6}$alkyl group;
X is a —S— atom;
Y is a N atom or CH group or substituted C atom;
n is zero or the integer 1;
Alk$^1$ is an optionally substituted aliphatic or heteroaliphatic chain;
L$^1$ is a covalent bond or a linker atom or group;
Cy$^1$ is an optionally substituted cycloaliphatic, polycycloaliphatic, heterocycloaliphatic, polyheterocycloaliphatic, aromatic or heteroaromatic group;
Ar is an optionally substituted aromatic or heteroaromatic group;
and the salts, solvates, and N-oxides thereof.

2. A compound according to claim 1 in which Cy$^1$ is an optionally substituted cycloaliphatic, aromatic or heteroaromatic group.

3. A compound according to claim 2 in which Cy$^1$ is an optionally substituted phenyl group.

4. A compound according to claim 1 in which Ar is an optionally substituted phenyl or monocyclic five- or six-membered heteroaromatic group.

5. A compound according to claim 4 in which Ar is an optionally substituted phenyl group.

6. A compound according to claim 1 in which R$^a$ is a hydrogen atom or methyl group.

7. A compound according to claim 1 in which L$^1$ is a covalent bond or an —O— or —S— atom or an —N(R$^2$)—, —C(O)—, —C(S)—, —S(O)— or —S(O)$_2$— group; and R$^2$ is a hydrogen atom or a straight or branched alkyl group.

8. A compound according to claim 7 in which L$^1$ is a covalent bond.

9. A compound according to claim 1 in which n is zero.

10. A compound according to claim 1 in which each Y is a CH group or a substituted C atom.

11. A compound according to claim 1 in which the dashed line represents a bond and A is a —C(R$^b$)= group.

12. A compound according to claim 11 in which R$^b$ is a hydrogen atom.

13. A compound which is:
Ethyl 6-oxo-3,7-diphenyl-6,7-dihydrothieno[2,3-b]pyridine-2-carboxylate;
Ethyl 7-cyclopropylmethyl-6-oxo-3-phenyl -6,7-dihydrothieno[2,3-b]pyridine-2-carboxylate;
Ethyl 6-oxo-3-phenyl-7-(3-thienyl)-6,7-dihydrothieno[2,3-b]pyridine-2-carboxylate;

Ethyl 3-(4-fluorophenyl)-6-oxo-7-phenyl-6,7-dihydrothieno[2,3-b]pyridine-2-carboxylate;

Ethyl 3-(2-methoxyphenyl)-6-oxo-7-phenyl-6,7-dihydrothieno[2,3-b]pyridine-2-carboxylate;

Ethyl 6-oxo-7-phenyl-3-(4-tolyl)-6,7-dihydrothieno[2,3-b]pyridine-2-carboxylate;

Ethyl 3-(3-methoxyphenyl)-6-oxo-7-phenyl-6,7-dihydrothieno[2,3-b]pyridine-2-carboxylate;

6-Oxo-3,7-diphenyl-N-(2-piperidinoethyl)-6,7-dihydrothieno[2,3-b]pyridine-2-carboxamide;

6-Oxo-3,7-diphenyl-6,7-dihydrothieno[2,3-b]pyridine-2-carbonitrile;

3,7-Diphenylthieno[2,3-b]pyridin-6(7H)-one;

Ethyl 3-(2,4-difluorophenyl)-7-[4-(4-methylpiperazin-1-yl)phenyl]-6-oxo-6,7-dihydrothieno[2,3-b]pyridine-2-carboxylate;

1,4-Diphenyl-1,4-dihydro-pyrrolo[3,2-b]pyridin-5-one;

Ethyl 7-(2-chlorophenyl)-6-oxo-3-phenyl-6,7-dihydrothieno[2,3-b]pyridine-2-carboxylate;

and the salts, solvates, and N-oxides thereof.

14. A pharmaceutical composition comprising an effective amount of a compound according to claim 1 together with one or more pharmaceutically acceptable carriers, excipients or diluents.

15. A method for the treatment of rheumatoid arthritis comprising administering to a manual an effective amount of a compound of claim 1.

* * * * *